(12) United States Patent
Ismagilov et al.

(10) Patent No.: US 11,866,695 B2
(45) Date of Patent: *Jan. 9, 2024

(54) METHODS AND SYSTEMS AND RELATED COMPOSITIONS FOR MIXTURES SEPARATION WITH A SOLID MATRIX

(71) Applicant: CALIFORNIA INSTITUTE OF TECHNOLOGY, Pasadena, CA (US)

(72) Inventors: Rustem F. Ismagilov, Altadena, CA (US); Erik Jue, Pasadena, CA (US); Daan Witters, San Diego, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 17/131,449

(22) Filed: Dec. 22, 2020

(65) Prior Publication Data

US 2021/0189379 A1 Jun. 24, 2021

Related U.S. Application Data

(60) Provisional application No. 62/953,178, filed on Dec. 23, 2019.

(51) Int. Cl.
*C12N 15/10* (2006.01)
*C12Q 1/6806* (2018.01)

(52) U.S. Cl.
CPC ..... *C12N 15/1006* (2013.01); *C12N 15/1013* (2013.01); *C12Q 1/6806* (2013.01)

(58) Field of Classification Search
CPC ............ C12N 15/1006; C12N 15/1003; C12N 15/1013; C12Q 1/6806
See application file for complete search history.

(56) References Cited

U.S. PATENT DOCUMENTS

| 5,582,988 | A | 12/1996 | Backus et al. |
|---|---|---|---|
| 8,883,088 | B2 | 11/2014 | Malik et al. |
| 9,415,392 | B2 | 8/2016 | Ismagilov et al. |
| 9,518,291 | B2 | 12/2016 | Malik et al. |
| 9,561,505 | B2 | 2/2017 | Malik et al. |
| 9,803,237 | B2 | 10/2017 | Ismagilov et al. |
| 9,822,356 | B2 | 11/2017 | Ismagilov et al. |
| 10,252,264 | B2 | 4/2019 | Shen et al. |
| 11,149,265 | B2 | 10/2021 | Ismagilov et al. |
| 11,174,477 | B2 | 11/2021 | Ismagilov et al. |
| 2004/0191923 | A1 | 9/2004 | Tomasso et al. |
| 2005/0169801 | A1 | 8/2005 | Fogel et al. |
| 2006/0159586 | A1 | 7/2006 | Sasaki et al. |
| 2006/0183216 | A1 | 8/2006 | Handique et al. |
| 2008/0090287 | A1 | 4/2008 | Larsen |
| 2008/0138884 | A1 | 6/2008 | Takeshita et al. |
| 2008/0293931 | A1 | 11/2008 | Dunbar et al. |
| 2010/0028204 | A1 | 2/2010 | Lee et al. |
| 2012/0077969 | A1 | 3/2012 | Petzel et al. |
| 2012/0184725 | A1 | 7/2012 | Forman et al. |
| 2014/0039177 | A1 | 2/2014 | Nelson et al. |
| 2015/0182966 | A1 | 7/2015 | Coursey et al. |
| 2015/0184149 | A1 | 7/2015 | Jiang et al. |
| 2016/0346781 | A1 | 12/2016 | Shen et al. |
| 2017/0037394 | A1 | 2/2017 | Chua et al. |
| 2017/0095814 | A1 | 4/2017 | Boehm et al. |
| 2019/0078080 | A1 | 3/2019 | Ismagilov |
| 2019/0100747 | A1 | 4/2019 | Ismagilov et al. |
| 2022/0049242 | A1 | 2/2022 | Ismagilov et al. |
| 2022/0098573 | A1 | 3/2022 | Ismagilov et al. |

FOREIGN PATENT DOCUMENTS

| JP | 2005531750 | A | 10/2005 |
|---|---|---|---|
| JP | 2006194843 | A | 7/2006 |
| WO | 2016/105508 | A2 | 6/2016 |
| WO | 2019/135800 | A2 | 7/2019 |
| WO | 2019/135801 | A2 | 7/2019 |

OTHER PUBLICATIONS

1-Undecanol. Gestis Substance Database downloaded from //gestis. itrust.de/nxt/gateway.dll/gestis_en/000000.xml?f=templates&fn=default.htm&vid-gestiseng:sdbeng on Apr. 17, 2020. 2 Pages.
3M Fluorinert™ FC-40 Electronic Liquid. Mat Web Material Property Data. Downloaded from www.matweb.com/search/datasheettext.aspx?matguid=2072a809f9ca4d529b1d136660736f81 on Apr. 17, 2020. 2 Pages.
Abd El-Aal, A. A., et al., Comparative study of five methods for DNA extraction from whole blood samples. *International Journal of Health Science*, vol. 3, Issue 1, pp. 285-287, 2010. 4 Pages.
"Adsorption" in the Glossary. The Brownfields and Land Revitalization Technology Support Center. www.brownfieldstsc.org/glossary.cfm?q=1 Date captured: Jan. 16, 2009. (https:http://www.brownfieldstsc.org/glossary.cfm?q=1). 2 pages.
"Adsorption" in the Glossary. The Brownfields and Land Revitalization Technology Support Center, Retrieved Dec. 19, 2009. web.archive.org/web/20091219063871/http://www.brownfieldstsc.org/glossary.cfm. 2 pages.
Alaeddini, R., Forensic implications of PCR inhibition—A review. Forensic science international: Genetics 6, 297-305, doi: 10.1016/j.fsigen.2011.08.006, pp. 297-305, 2012. 11 Pages.

(Continued)

*Primary Examiner* — Jezia Riley
(74) *Attorney, Agent, or Firm* — Steinfl + Bruno LLP

(57) ABSTRACT

Methods and systems and related compositions for separating through a solid matrix a mixture comprising a nucleic acid in a concentration of 1 μM or less, together with a target compound having a water solubility equal to or greater than 0.001 g per 100 mL, which can be used for managing fluid flow, biochemical reactions and purification of the nucleic acid or other target analytes. The method comprises contacting the solid matrix with a target compound removing agent having a water solubility equal to or less than 0.05 g per 100 mL at 25° C. at 1 atm pressure with water having a solubility in the removing agent of less than 10 g per 100 mL at 25° C. at 1 atm pressure, the contacting performed to remove the target compound from the solid matrix.

15 Claims, 17 Drawing Sheets

(56) References Cited

OTHER PUBLICATIONS

Ali, N., et al., Current Nucleic Acid Extraction Methods and Their Implications to Point-of-Care Diagnostics. *BioMed research international*, 2017, 9306564, doi: 10.1155/2017 /9306564, 2017. 13 Pages.

Arkles, B., et al., Silicone Fluids: Stable, Inert Media. *Gelest, Inc*, 2013. 34 Pages.

Barton, Allan FM, et al., Alcohols with Water in Solubility Data Series vol. 15. Pergamon Press, 1984, 457 Pages.

Bergallo, M. et al. Evaluation of six methods for extraction and purification of viral DNA from urine and serum samples. *The new microbiologica*, 29, 111-119, 2006. 10 pages.

Berry, S. M., et al., One-step purification of nucleic acid for gene expression analysis via Immiscible Filtration Assisted by Surface Tension (IFAST). Lab on a chip 11, 1747-1753, doi: 10.1039/c1 lc00004g, 2011, 7 pages.

Bessetti, J., et al., "An Introduction to -PCR Inhibitors," Profiles in DNA by Promega Corporation, Mar. 2007. Retrieved from www.promega.es/-/media/files/resources/profiles-in-dna/1001/an-introduction-to-pcr-inhibitors.pdf?la=es-es. 2 Pages.

Biava, M. et al. Evaluation of a rapid and sensitive RT-qPCR assay for the detection of Ebola Virus. *J. Virol. Methods*, 252, 70-74, doi: 10.1016/j.jviromet.2017.11.009, 2018. 7 Pages.

Boesenberg-Smith, K.A., et al., Assessment of DNA yield and purity: an overlooked detail of PCR troubleshooting. *Clin. Microbiol. News*. 34, No. 1, 1-6, Jan. 1, 2012. 6 Pages.

Bustin, S. A., et al. Quantitative real-time RT-PCR—a perspective. J. Mol. Endocrinol. 34, 597-601, doi:10.1677/jme.1.01755, 2005. 5 pages.

Butler, J.A.V., et al., "The free energy of the normal aliphatic alcohols in aqueous solution. Part I. The partial vapour pressures of aqueous solutions of methyl, n-propyl, and n-butyl alcohols. Part II. The solubilities of some normal aliphatic alcohols in water. Part III. The theory of binary solutions, and its application to aqueous-alcoholic solutions," J. Chem. Soc., 1933, 674-686. doi.org/10.1039/JR9330000674. 14 Pages.

Chacon-Coretes, D., et al., Methods for extracting genomic DNA from whole blood samples: current perspectives. *Journal of Biorepository Science for Applied Medicine*, 2014, 2, 1-9, 9 pages.

Craw, P. et al., Isothermal nucleic acid amplification technologies for point-of-care diagnostics: a critical review. *Lab on a chip*, 12, 2469-2486, doi:10.1039/c2lc40100b, 2012. 18 Pages.

Crini, Chapter 1—"Sorption processes and pollution: conventional and non-conventional sorbents for pollutant removal", Presses universitaires de Franche-Comte, 2010, p. 34-37, ISBN 9782848673042.

Crotchfelt, K. A., et al., Detection of Neisseria gonorrhoeae and Chlamydia trachomatis in genitourinary specimens from men and women by a coamplification PCR assay. J. Clin. Microbial. 35, 6, 1536-1540, 1997, 5 pages.

Day, E., et al., Digital PCR strategies in the development and analysis of molecular biomarkers for personalized medicine. Methods 59, 101-107, 2013, 7 pages.

Demeke, T., et al., Influence of DNA extraction methods, PCR inhibitors and quantification methods on real-time PCR assay of biotechnology-derived traits. Anal. Bioanal. Chem. 396, 1977-1990, doi: 10.1007 /s00216-009-3150-9, 2010. 14 pages.

Francois, P., et al. Robustness of a loop-mediated isothermal amplification reaction for diagnostic applications. FEMS Immunol. Med. Microbial. 62, 41-48, doi:10.1111/j.1574-695X.2011.00785.x, 2011, 8 pages.

Gielis, E. M. et al., Cell-Free DNA: An Upcoming Biomarker in Transplantation. Am. J. Transplant. 15, 2541-2551, doi:10.1111/ajt.13387, 2015. 11 Pages.

Goldberg, C. S., et al., Environmental DNA as a new method for early detection of New Zealand mudsnails (*Potamopyrgus antipodarum*). Freshwater Science 32 (3), 792-800, Jun. 18, 2013, 9 Pages.

Goto, M., et al., Colorimetric detection of loop-mediated isothermal amplification reaction by using hydroxy naphthol blue. Bio Techniques 46 (3), 167-172, doi:10.2144/000113072, 2009, 4 pages.

Hu, Q., et al., A comparison of four methods for PCR inhibitor removal. Forensic science international: Genetics 16, 94-97, doi:10.1016/j.fsigen.2014.12.001, 2015. 6 pages.

Huggett, J.F., et al., Differential susceptibility of PCR reactions to inhibitors: an important and unrecognized phenomenon. BMC Res. Notes 1, 70,doi:10.1186/1756-0500-1-70, Aug. 28, 2008, 9 pages.

International Preliminary Report on Patentability (Chapter I) for International Application No. PCT/US2018/051201 filed on Sep. 14, 2018 on behalf of California Institute of Technology dated Mar. 26, 2020. 8 pages.

International Preliminary Report on Patentability for International Application No. PCT/US2018/050919 filed on Sep. 13, 2018 on behalf of California Institute of Technology dated Mar. 26, 2020. 8 pages.

International Preliminary Report on Patentability for International Application No. PCT/US2018/050919 filed Sep. 13, 2018 on behalf of California Institute of Technology. dated Mar. 17, 2020. 7 Pages.

International Search Report for International Application No. PCT/US2018/050919 filed Sep. 13, 2018 on behalf of California Institute of Technology. dated Aug. 2, 2019. 4 pages.

International Search Report for International Application No. PCT/US2018/051201 filed Sep. 14, 2018 on behalf of California Institute of Technology. dated Aug. 1, 2019. 4 pages.

Invitrogen/Ambion nuclease-free water (noDEPC-treated): downloaded from www.thermofisher.com/order/catalog/product/AM9932#/AM9932 on Feb. 2, 2021. 4 pages.

Jue, E., et al., "Two-phase wash to solve the ubiquitous contaminant-carryover problem in commercial nucleic-acid extraction kits", Scientific Reports, (2020) 10:1940. 16 pages.

Kamau, E., et al., Multiplex qPCR for detection and absolute quantification of malaria. PLoS One, vol. 8, Issue 8, e71539, doi: 10.1371/journal.pone.0071539, Aug. 2013, 9 pages.

Kaneko, H., et al., Tolerance of loop-mediated isothermal amplification to a culture medium and biological substances. *J. Biochem. Biophys. Methods*,70, 499-501, doi:10.1016/j.jbbm.2006.08.008, 2007, 5 Pages.

Klein, D., Quantification using real-time PCR technology: applications and limitations. Trends Mol. Med. vol. 8, No. 6, 257-260, published online: May 8, 2002, 4 pages.

Kogovsek, P., et al., Rapid loop-mediated isothermal amplification assays for grapevine yellows phytoplasmas on crude leaf-vein homogenate has the same performance as qPCR. Eur. J. Plant Pathol. 148, 75-84, 2017, 10 pages.

Kuehnelt, D.M., et al., Quantitative PCR of bacteriophage lambda DNA using a second-generation thermocycler. PCR Methods Appl. 3, 369-371, 1994, 4 pages.

Lee, et all, "Centrifugation-free extraction of circulating nucleic acids using immiscible liquid under vacuum pressure", Scientific Reports, (2018), 8:5467, pp. 1-11.

Lee, S. R., et al., Rapid one step detection of pathogenic bacteria in urine with sexually transmitted disease (STD) and prostatitis patient by multiplex PCR assay (mPCR). J. Microbial. 45, n. 5, 453-459, 2007. 7 Pages.

Mahony, J., et al. Urine specimens from pregnant and nonpregnant women inhibitory to amplification of Chlamydia trachomatis nucleic acid by PCR, ligase chain reaction, and transcription-mediated amplification: identification of urinary substances associated with inhibition and removal of inhibitory activity. J. Clin. Microbiol. 36, n. 11, 3122-3126, 1998. 5 pages.

Mason, W. J., et al., Multiplex PCR protocol for the diagnosis of staphylococcal infection. J. Clin. Microbial. 39, n. 9, 3332-3338, doi: 10.1128/jcm.39.9.33323338.2001, 2001. 7 Pages.

Matsuda, K., et al., Sensitive quantitative detection of commensal bacteria by rRNA-targeted reverse transcription-PCR. Appl. Environ. Microbial. 73, n.1, 32-39, doi:10.1128/aem.01224-06, Jan. 2007. 8 pages.

Nixon, G. et al. Comparative study of sensitivity, linearity, and resistance to inhibition of digital and nondigital polymerase chain reaction and loop mediated isothermal amplification assays for quantification of human cytomegalovirus. Anal. Chem. 86, 4387-4394, doi:10.1021/ac500208w, 2014. 8 Pages.

(56) References Cited

OTHER PUBLICATIONS

N-Octanol. Gestis Substance Database downloaded from gestis. dguv.de/data?name=037840&lang=en downloaded on Feb. 3, 2021. 14 Pages.
Nolan, T., et al., Spud: a quantitative PCR assay for the detection of inhibitors in nucleic acid preparations. Anal. Biochem. 351, 308-310, doi: 10.1016/j.ab.2006.01.051, 2006. 3 Pages.
Non-Final Office Action for U.S. Appl. No. 16/130,810, filed Sep. 13, 2018, on behalf of California Institute of Technology. dated Feb. 2, 2021. 25 pages.
Non-Final Office Action for U.S. Appl. No. 16/132,235, filed Sep. 14, 2018 on behalf of California Institute of Technology. dated Jan. 12, 2021. 22 pages.
Notomi, T. et al., Loop-mediated isothermal amplification of DNA. Nucleic Acids Res. vol. 28, No. 12, E63, doi: 10.1093/nar/28.12. e63, 2000, 7 pages.
Opel, K. L., et al., A study of PCR inhibition mechanisms using real time PCR. J. Forensic Sci. 55, 25-33, doi:10.1111/j.1556-4029.2009. 01245.x, 2009, 10 pages.
Peist, R., et al., PCR inhibitors in plant DNA preparations. Qiagen news 3, 7-9, 2001, 4 pages.
Price, C. W., et al., Nucleic acid extraction techniques and application to the microchip. Lab on a chip 9, 2484-2494, doi:10.1039/b907652m, 2009. 11 Pages.
Priye, A., et al., A smartphone-based diagnostic platform for rapid detection of Zika, chikungunya, and dengue viruses. Sci. Rep. 7, 44778, doi:10.1038/srep44778, 2017. 11 pages.
Qiu, J., et al., Development of a Real-Time Polymerase Chain Reaction Method to Measure Ligation Efficiency. Journal of Experimental Microbiology and Immunology, 2015, .7 pages.
Radstrom, P., et al., Strategies for overcoming PCR inhibition. CSH protocols 2008, vol. 3, issue 3, pdb.top20, doi: 10.1101/pdb.top20, 2008, 12 pages.
Restriction Requirement for U.S. Appl. No. 16/130,810, filed Sep. 13, 2018 on behalf of California Institute of Technology dated Nov. 27, 2020. 5 pages.
Restriction Requirement for U.S. Appl. No. 16/132,235, filed Sep. 14, 2018 on behalf of California Institute of Technology dated Aug. 11, 2020. 8 pages.
Rossen, L., et al., Inhibition of PCR by components of food samples, microbial diagnostic assays and DNA-extraction solutions. Int. J. Food Microbiol. 17, 37-45, doi:10.1016/0168-1605(92)90017-w, 1992, 11 pages.
Rudi, K., et al., Different length (DL) qPCR for quantification of cell killing by UV-induced DNA damage. Int. J. Env. Res. Public Health 7, 3376-3381, doi: 10.3390/ijerph7093376, 2010, 6 pages.
Schoepp, N.G., et al., Rapid pathogen-specific phenotypic antibiotic susceptibility testing using digital LAMP quantification in clinical samples. Sci. Transl. Med. 9, eaal3693, doi:10.1126/scitranslmed. aal369 , Oct. 4, 2017. 13 pages.
Schrader, C., et al., PCR inhibitors—occurrence, properties and removal. J. Appl. Microbiol. 113, 1014-1026, doi:10.1111/j.1365-2672.2012.05384.x, 2012. .13 pages.
Simbolo, M., et al. DNA qualification workflow for next generation sequencing of histopathological samples. PLoS One, vol. 8, issue 6, e62692, doi:10.1371/journal.pone.0062692, Jun. 6, 2013. 8 pages.
Sr, K., PCR Technique with its Application. Research & Reviews: Journal of Microbiology and Biotechnology, vol. 4, issue 1, 1-12, Feb.-Mar. 2015. 13 pages.
Sriworarat, C., et al., Development of loop-mediated isothermal amplification (LAMP) for simple detection of Leishmania infection. Parasites & vectors 8, 591, doi: 10.1186/s13071-015-1202-x, 2015, 8 pages.
Sur, K., et al., Immiscible phase nucleic acid purification eliminates PCR inhibitors with a single pass of paramagnetic particles through a hydrophobic liquid. The Journal of molecular diagnostics, vol. 12, No. 5, 620-628, doi: 10.2353/jmoldx.2010.090190, 2010, 9 Pages.
Tanner, N. A., et al., Loop-mediated isothermal amplification for detection of nucleic acids. Curr. Protoc. Mol. Biol. 105, Unit 15.14., doi:10.1002/0471142727.mb1514s105, 2014, 14 pages.

Tebbe, C. C., et al., Interference of humic acids and DNA extracted directly from soil in detection and transformation of recombinant DNA from bacteria and a yeast. Appl. Environ. Microbiol. vol. 59, No. 8, 2657-2665, 1993, 9 pages.
Valones, M. A. et al., Principles and applications of polymerase chain reaction in medical diagnostic fields: a review. Braz. J. Microbiol. 40, 1-11, doi:10.1590/s1517-83822009000100001, 2009, 11 pages.
Wilson, I. G. Inhibition and facilitation of nucleic acid amplification. Appl. Environ. Microbiol. 63, No. 10, pp. 3741-3751, 1997, 11 pages.
Witters, et al., "Autonomous and portable device for rapid sample-to-answer molecular diagnostics at the point-of-care", 2017, California Institute of Technology Pasadena CA, SlipChip Corp, Menlo Park, USA. 1 page.
Written Opinion for International Application No. PCT/US2018/050919 filed Sep. 13, 2018 on behalf of California Institute of Technology. dated Aug. 2, 2019. 6 pages.
Written Opinion for International Application No. PCT/US2018/051201 filed Sep. 14, 2018 on behalf of California Institute of Technology. dated Aug. 1, 2019. 6 pages.
Yager, P., et al., Point-of-care diagnostics for global health. Annu. Rev. Biomed. Eng. 10, 107-144, doi:10.1146/annurev.bioeng.10. 061807.160524, 2008. 40 pages.
Yamakazi, W., et al., Development of a loop-mediated isothermal amplification assay for sensitive and rapid detection of Vibrio parahaemolyticus. BMC Microbial. 8, 163, doi: 10.1186/1471-2180-8-163, Sep. 30, 2008, 7 pages.
2-Bromothiazole, TCI, accessed on May 25, 2021 at www.tcichemicals.com/US/en/p/B1280, 5 pages.
5 reasons why pandemics like Covid-19 are becoming more likely, "Gavi: The Vaccine Alliance". Apr. 28, 2020. Downloaded on Nov. 5, 2021. Available online from www.gavi.org/vaccineswork/5-reasons-why-pandemics-like-covid-19-are-becoming-more-likely. 5 Pages.
Cephid, Molecular Diagnostics. Home page + Mission Page. Downloaded on Nov. 5, 2021. Available online from www.cepheid.com/en_US/personas/laboratory-professionals. 22 Pages.
Corrected Notice of Allowability for U.S. Appl. No. 16/132,235, filed Sep. 14, 2018, on behalf of California Institute of Technology. dated Sep. 15, 2021. 3 Pages.
Ex Parte Quayle for U.S. Appl. No. 16/132,235, filed Sep. 14, 2018 on behalf of California Institute of Technology. Mail Date: Jun. 23, 2021. 6 Pages.
Fitzpatrick et al., "Practical Method for Extraction of PCR-Quality DNA from Environmental Soil Samples", *Applied and Environmental Microbiology*, Jul. 2010, vol. 76, No. 13, p. 4571-4573.
Gill, V., "Coronavirus: This is not the last pandemic," BBC News, Jun. 6, 2020. Downloaded on Nov. 5, 2021. Available online from www.bbc.com/news/science-environment-52775386. 10 Pages.
Hilsenrath, J., "Global Viral Outbreaks Like Coronavirus, Once Rare, Will Become More Common; Urbanization, globalization and increased human consumption of animal proteins are driving a rise in epidemics" Wall Street Journal. Mar. 6, 2020. 6 pages. Available online from www.wsj.com/articles/viral-outbreaks-once-rare-become-part-of-the-global-landscape-11583455309. 6 pages.
Notice of Allowance for U.S. Appl. No. 16/130,810, filed Sep. 13, 2018, on behalf of California Institute of Technology. dated Jun. 11, 2021. 7 Pages.
Notice of Allowance for U.S. Appl. No. 16/132,235, filed Sep. 14, 2018, on behalf of California Institute of Technology. dated Jul. 14, 2021. 5 pages.
N-Phenacylthiazolium bromide in cymitquimica.com, accessed on May 25, 2021 at cymitquimica.com/products/10-080244/5304-34-7/n-phenacylthiazolium-bromide/. 7 pages.
Pimagedine, Wikepedia, accessed on May 25, 2021 at en.wikipedia.org/wiki/Pimagedine. 4 pages.
Pyridoxamine, Dihydrochloride, Millipore Sigma, accessed on May 25, 2021 at www.emdmillipore.com/US/en/product/Pyridoxamine-

(56) References Cited

OTHER PUBLICATIONS

Dihydrochloride-CAS-524-36-7-Calbiochem,EMD_BIO-545068, 3 pages.

Thiamine Hydrochloride, *fisherscientific*, accessed on May 25, 2021 at www.fishersci.com/shop/products/thiamine-hydrochloride-98-5-101-5-acros-organics-3/AC148990100, 3 pages.

Thiamine Pyrophosphate Chloride, *fisherscientific*, accessed on May 25, 2021 at www.fishersci.com/shop/products/thiamine-pyrophosphate-chloride-tci-america-2/T01835G, 2 pages.

World Health Organization Coronavirus Dashboard, Global Information as of Nov. 4, 2021. Downloaded on Nov. 5, 2021. Available online from covid19.who.int/. 1 Page.

Heo et al., A valveless rotary microfluidic device for multiplex point mutation identification based on ligation-rolling circle amplification, Nov. 14, 2015, Biosensors and Bioelectronics, 78, pp. 140-146.

Lai, et al., Calibration Curves for Real-Time PCR. Molecular Diagnostics and Genetics, Clinical Chemistry, 51:7, 1132-1136 (2005).

Non-Final Office Action for U.S. Appl. No. 17/511,235, filed Oct. 26, 2021 on behalf of California Institute of Technology dated Jan. 9, 2023. 9 pages.

Non-Final Office Action issued for U.S. Appl. No. 17/473,832, filed Sep. 13, 2021 on behalf California Institute of Technology. dated Mar. 22, 2023. 13 pages.

Sedlak, R.H. et al., A multiplexed droplet digital PCR assay performs better than qPCR on inhibition prone samples. Diagnostic Microbiology and Infectious Disease, vol. 80, Issue 4, Dec. 2014, pp. 285-286. 3 pages.

Tang, Yi-Wei, et al. Molecular diagnostics of infectious diseases. Clinical Chemistry, 43:11, pp. 2021-2038. (1997).

Wiktionary, definition of "rxn". Downloaded through the Wayback Machine, dated Oct. 2, 2015. 1 page.

Corrected Notice of Allowability for U.S. Appl. No. 17/511,235, filed Oct. 26, 2021 on behalf of California Institute of Technology dated Jul. 24, 2023. 3 pages.

Definition of "kit" by Merriam Webster dictionary. Downloaded from web.archive.org with a date of Aug. 17, 2017. 12 pages.

Notice of Allowance for U.S. Appl. No. 17/511,235, filed Oct. 26, 2021 on behalf of California Institute of Technology dated Apr. 13, 2023. 8 pages.

Notice of Allowance issued for U.S. Appl. No. 17/473,832, filed Sep. 13, 2021 on behalf California Institute of Technology. dated Jun. 28, 2023. 10 pages.

Zymo Research, Quick-DNA/RNA Viral 96 Kit. Downloaded Mar. 15, 2023. 72 pages. Website: www.zymoresearch.com/products/quick-dna-rna-viral-96-kit.

METHODS AND SYSTEMS AND RELATED COMPOSITIONS FOR MIXTURES SEPARATION WITH A SOLID MATRIX

CROSS REFERENCE TO RELATED APPLICATION

The present application claims priority of U.S. Provisional Application No. 62/953,178, entitled "Methods and Device for Purification and Detection of Analytes," filed on Dec. 23, 2019 and may be related to U.S. Provisional Application No. 62/558,679, entitled "Methods and Device for Purification and Detection of Analytes", filed on Sep. 14, 2017, to U.S. application Ser. No. 16/132,235 entitled "Methods And Systems And Related Compositions For Mixtures Separation With A Solid Matrix" filed on Sep. 14, 2018, to PCT International Application PCT/US18/51201 filed on Sep. 14, 2018 and entitled "Methods And Systems And Related Compositions For Mixtures Separation With A Solid Matrix," and to U.S. application Ser. No. 16/130,810 filed on Sep. 13, 2018 and entitled "Purification and Detection of Analytes" and PCT International Application PCT/US18/50919 filed on Sep. 13, 2018 and entitled "Purification and Detection of Analytes" the entire disclosures of each of which are herein incorporated by reference in its entirety.

STATEMENT OF GOVERNMENT GRANT

This invention was made with government support under Defense Threat Reduction Agency (DTRA) award MCDC-18-01-01-007, and under number W15QKN-16-9-1002 between the MCDC, and the government. The government has certain rights in the invention.

FIELD

The present disclosure generally relates to biochemistry and molecular biology, and more specifically to methods and systems and related compositions for separation of mixtures with a solid matrix.

BACKGROUND

In the biochemistry and molecular biology fields, several processes and reactions involve separation of mixtures of one or more analytes alone or in combination with additional compounds, wherein the separation is performed with a solid matrix.

In particular, in the above fields several processes and reactions involve separation of mixtures where nucleic acid is comprised typically as an analyte, together with additional compounds.

However, despite the advancement of the technology, performing an efficient and effective matrix separation of mixtures comprising nucleic acids through a solid matrix, remains challenging in particular when the separation is directed to provide the nucleic acid as a substrate for further biochemical reactions.

SUMMARY

Provided herein, are methods and systems and related compositions that can be used to separate a solution comprising a nucleic acid together with an additional compound, which in several embodiments allow purification of nucleic acid and separate a solution comprising a nucleic acid together with an additional compound while minimizing rehydration of the separated nucleic acid, minimizing nucleic acid loss during separation, and allow effective separation of nucleic acid from samples including nucleic acids at a low concentration and/or from related solutions at low dilutions.

According to a first aspect, a method and a system are described to selectively remove from a solid matrix a target compound absorbed to the solid matrix and having a water solubility equal to or greater than 0.001 g per 100 mL at 25° C. at 1 atm pressure, the solid matrix further retaining a nucleic acid.

The method comprises: contacting the solid matrix with a target compound removing agent having a water solubility equal to or less than 0.05 g per 100 mL at 25° C. at 1 atm pressure, preferably equal to or less than 0.03 g per 100 mL at 25° C. at 1 atm pressure with water having a solubility in the removing agent of less than 10 g per 100 mL at 25° C. at 1 atm pressure. In the method the contacting is performed for a time and under condition to remove the target compound from the solid matrix.

The system comprises a target compound removing agent having a water solubility equal to or less than 0.05 g per 100 mL at 25° C. at 1 atm pressure, preferably equal to or less than 0.03 g per 100 mL at 25° C. at 1 atm pressure with water having a solubility in the removing agent of less than 10 g per 100 mL at 25° C. at 1 atm pressure; and a solid matrix configured to absorb a nucleic acid for simultaneous combined or sequential use in the method to selectively remove from a solid matrix a target compound herein described.

According to a second aspect, a method and a system are described to selectively capture a nucleic acid in a solid matrix.

The method comprises: contacting the solid matrix with a solution comprising the nucleic acid at a concentration of 1 μM or less, together with a target compound having a water solubility equal to or greater than 0.001 g per 100 mL at 25° C. at 1 atm pressure; and contacting the solid matrix with a target compound removing agent having a water solubility equal to or less than 0.05 g per 100 mL at 25° C. at 1 atm pressure, preferably equal to or less than 0.03 g per 100 mL at 25° C. at 1 atm pressure with water having a solubility in the removing agent of less than 10 g per 100 mL at 25° C. at 1 atm pressure.

In the method, contacting the solid matrix with a solution comprising the nucleic acid is performed for a time and under condition to allow absorbance of the nucleic acids to the solid matrix. The contacting the solid matrix with a target compound removing agent is performed for a time and under condition to remove the target compound from the solid matrix thus capturing the nucleic acid in the solid matrix.

The system comprises a target compound removing agent having a water solubility equal to or less than 0.05 g per 100 mL at 25° C. at 1 atm pressure, preferably equal to or less than 0.03 g per 100 mL at 25° C. at 1 atm pressure with water having a solubility in the removing agent of less than 10 g per 100 mL at 25° C. at 1 atm pressure; and a solid matrix configured to absorb a nucleic acid for simultaneous combined or sequential use in the method to selectively capture a nucleic acid in a solid matrix of the present disclosure.

According to a third aspect, a method and a system are described to separate a nucleic acid from a mixture further comprising an additional target compound.

The method comprises capturing the nucleic acid in a solid matrix by performing any one of the methods to capture a nucleic acid herein described; and eluting the captured nucleic acid from the solid matrix.

The system comprises a target compound removing agent having a water solubility equal to or less than 0.05 g per 100 mL at 25° C. at 1 atm pressure, preferably equal to or less than 0.03 g per 100 mL at 25° C. at 1 atm pressure with water having a solubility in the removing agent of less than 10 g per 100 mL at 25° C. at 1 atm pressure; and a nucleic acid removing agent for simultaneous combined or sequential use in the method to separate a nucleic acid from a mixture herein described.

According to a fourth aspect, a method and a system are described to perform a biochemical reaction of a nucleic acid.

The method comprises capturing the nucleic acid in a solid matrix by performing any one of the methods to capture a nucleic acid herein described; eluting the captured nucleic acid from the solid matrix; and contacting the eluted nucleic acid with a suitable reagent to perform the biochemical reaction.

The system comprises a target compound removing agent having a water solubility equal to or less than 0.05 g per 100 mL at 25° C. at 1 atm pressure, preferably equal to or less than 0.03 g per 100 mL at 25° C. at 1 atm pressure with water having a solubility in the removing agent of less than 10 g per 100 mL at 25° C. at 1 atm pressure; and at least one of a solid matrix configured to absorb a nucleic acid and a reagent to perform the biochemical reaction, for simultaneous combined or sequential use in the method to perform a biochemical reaction of a nucleic acid.

Methods and systems herein described and related compositions, in several embodiments can be used to perform an effective and selective solid matrix separation of a nucleic acid from a sample further including target compounds such as impurities retained in the solid matrix, while minimizing nucleic acid loss during the separation, In particular, in several embodiments, at least 50%, at least 80%, at least 90%, at least 95%, at least 99%, or at least 99.9% of the nucleic acid is retained on the solid matrix after separation of the target compound In the methods and systems herein described and related compositions, in several embodiments can be used to perform an effective and selective solid matrix separation of a nucleic acid from a sample further including a target compound such as impurities retained in the solid matrix, while maximizing the amount of target compound removed in the separation while retaining up to 99.9% of the nucleic acid of the solid matrix. In particular, in several embodiments, at least 50%, 60%, 70%, 80%, 90%, 99%, 99.9%, 99.99% of a target compound such as an impurity is removed from the solid matrix by the target compound removing agent while retaining nucleic acid as will be understood by a skilled person.

Methods and systems herein described and related compositions, in several embodiments can be used to perform an effective and selective solid matrix separation of a nucleic acid from a sample further including target compounds such as impurities retained in the solid matrix in samples including nucleic acids at a low concentration In particular in several embodiments methods and systems herein described can separate nucleic acid at a concentration of 1 μM or less, 1 nM or less, in particular a concentration of 1 pM or less in a sample.

Methods and systems herein described and related compositions, in several embodiments can be used to perform an effective and selective solid matrix separation of a nucleic acid from a sample further including target compounds such as impurities retained in the solid matrix in samples including nucleic acids at low dilutions, wherein the nucleic acid in the sample has a concentration of 1 μM or less, 1 nM or less, in particular a concentration of 1 pM or less.

Methods and systems herein described and related compositions, in several embodiments can be integrated with existing protocols to conduct biochemical reactions to detect and/or analyze nucleic acids with high sensitivity reducing carry over of extraction buffers while minimizing nucleic acid losses as will be understood by a skilled person.

Methods and systems herein described and related compositions, in several embodiments can be used to perform nucleic acid purification which reduces and in particular minimizes presence in the separated nucleic acid of compounds capable of inhibiting a biochemical reaction of the separated nucleic acid in a wide range of samples, including samples in samples wherein the nucleic acids is known or expected to be including nucleic acids at a low concentration and/or at low concentrations.

Accordingly, methods and systems herein described and related compositions, in several embodiments can be used to perform nucleic acid amplification and/or any other biochemical reactions of a nucleic acid from a sample or other mixture where the nucleic acid is comprised together with additional compounds in a wide range of samples, including samples wherein the nucleic acids are known or expected to be including nucleic acids at a low concentration at low dilutions.

The methods and systems herein described and related compositions can be used in connection with various applications wherein separation of mixtures comprising a nucleic acid together with other compounds is desired. For example, methods and systems herein described and related compositions can be used in applications to detect and/or amplify nucleic acid from mixtures such as processed or unprocessed samples. Additional exemplary applications include separation and/or uses of the separated nucleic acid and/or target compounds in several fields including basic biology research, applied biology, bio-engineering, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein.

DETAILED DESCRIPTION

Figure 1:
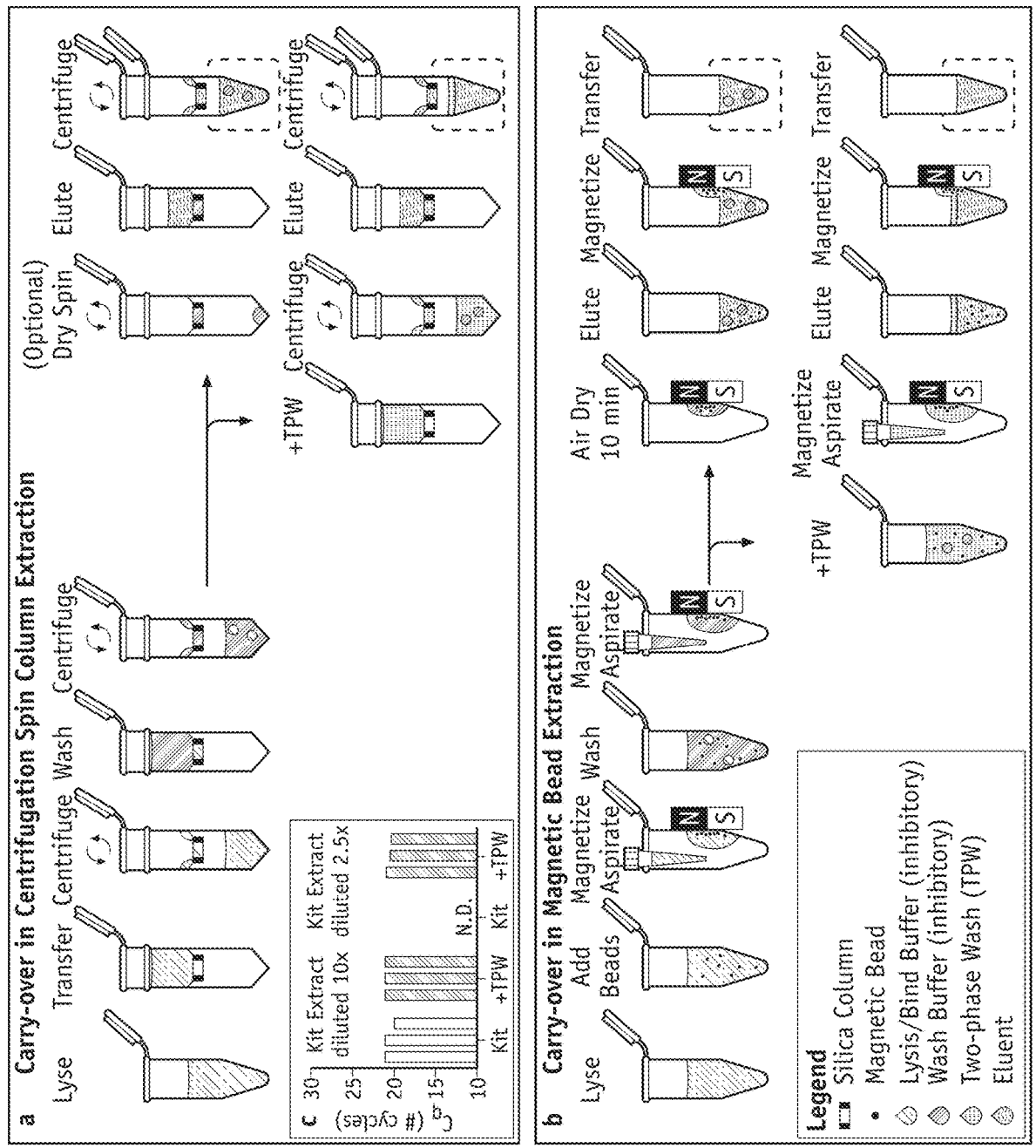
FIG. 1 shows a schematic depicting the carryover of buffers during sample preparation when nucleic acids (NA) are extracted using either (Panel a) spin column centrifugation or (Panel b) magnetic beads. Dashed red boxes highlight carryover of buffer into the eluent. Carryover buffer from the previous wash either mixes with the eluent (top dashed box in each panel) or phase separates (bottom dashed box in each panel) when the two-phase wash (TPW) is used. (Panel c) Inset graph shows a qPCR run spiked with 5×104 copies λ phage DNA and X phage primers into which was added Zymo ZR "kit extract." (When extracting from Nuclease- Free Water (not DEPC-Treated) from Invitrogen (catalog number AM9932) samples, eluent was referred to as the "kit extract," which only contains water and inhibitors originating from buffers in the extraction kits.) The graph compares the reaction inhibition in a 10× extract dilution and a 2.5×extract dilution and shows the effect of adding a TPW (+TPW) during the nucleic-acid extraction step. Inhibition is similarly observed for magnetic bead extraction kits. N.D. stands for not detected. 6 extractions (3 silica columns×2 conditions) were run and the same kit extract was used to make the high- and low-dilution conditions.

Provided herein are methods and systems and related compositions that can be used to separate a mixture comprising a nucleic acid together with a target compound which are effective in performing separation of the target compound from a mixture wherein the nucleic acid is comprised. In particular, in preferred embodiments, methods and systems and related compositions can be used to perform effective and selective separation of the target compound from a mixture wherein the nucleic acid is comprised at low concentration (a concentration of 1 M or less).

The term "separate" or "separation" as used herein indicates a process converting a source mixture of chemical substances into two or more distinct product mixtures. In particular, in embodiments herein described, the source mixture is a solution comprising the nucleic acid. In separations in the sense of the disclosure the conversion of the mixture into distinct product mixtures is performed based on differences in physical and/or chemical properties of the components of the mixture, such as shape, mass, density, size, chemical affinity and/or additional physical and/or chemical properties of the components of the solution identifiable by a skilled person.

In a separation according to the disclosure at least one of the product mixtures is typically enriched in one or more components of the starting mixture, typically the nucleic acid. In some cases, in at least one product mixture provided in outcome of a separation in accordance with the disclosure, the presence of the one or more component of the source mixture is maximized while the presence of other components of the starting mixture is minimized. In those cases, the separation can result in a complete division of the one or more components of the source mixture, typically the nucleic acid, from the other components and therefore in the related purification.

Exemplary mixtures in the sense of the disclosure comprise processed or unprocessed samples of an environment provided for use in testing, examination, or study. The environment can comprise a biological environment including living beings and, in particular, human beings.

The term "sample" as used herein indicates a limited quantity of something that is indicative of a larger quantity of that something, including but not limited to fluids from the biological environment, such as tissues, organs or other biological material from the living being such as urethra, urine, cervix, vagina, rectum, oropharynges, conjunctiva, or any body fluids, cultures, tissues, commercial recombinant proteins, synthetic compounds or portions thereof. Exemplary biological samples comprise: cheek tissue, whole blood, dried blood spots, organ tissue, plasma, urine, mucus, mucosal secretions, vaginal fluids and secretions, urethral fluids and secretions, feces, skin, hair, or tumor cells, among others identifiable by a skilled person. Biological samples can be obtained using sterile techniques or non-sterile techniques, as appropriate for the sample type, as identifiable by persons skilled in the art. Some biological samples can be obtained by contacting a swab with a surface on a human body and removing some material from said surface, examples include throat swab, urethral swab, oropharyngeal swab, cervical swab, vaginal swab, genital swab, anal swab.

Typically, a biological sample provided for use in testing, examination, or study is further processed with agents which are selected to allow and/or facilitate the intended testing examination or study. Exemplary agents comprise a buffer agent which is a chemical compound that is capable of maintain the pH value stability of an aqueous solution, or a chaotropic agent which a molecule in water solution that can disrupt the hydrogen bonding network between water molecules and can be used to disrupt membrane integrity of a cell. Additional agents used to treat a biological sample comprise a biological medium, an antibiotic, and additional agents identifiable by a skilled person in view of the intended use of the biological sample. Depending on the type of biological sample and the intended analysis, biological samples can be used freshly for sample preparation and analysis, stored at room temperature, stored under refrigeration, stored frozen, treated with a lysis solution and then stored, or fixed using fixative. For example, urine can be mixed with specimen transport and storage tube (see e.g. Aptima® Urine Specimen Transport Tube and additional commercially available containers).

In methods and systems herein described a separation of a mixture of nucleic acid and target compound in the sense of the disclosure can be performed for analytical purposes, and therefore be directed to qualitatively or quantitatively detect at least one component of the source mixture, typically the nucleic acid. A separation in the sense of the disclosure can be performed for preparative purposes, and therefore be directed to prepare fractions of the mixture components, typically the nucleic acid, that can be saved and/or used to perform additional reactions.

In particular, in several embodiments of the disclosure the separation can be performed to detect and/or purify the nucleic acid component of the source mixture while removing the target compound from the mixture.

The term "nucleic acid" "NA" or "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. Accordingly, the term "polynucleotide" includes nucleic acids of any length, and in particular DNA, RNA, and fragments thereof. A "nucleotidic oligomer" or "oligonucleotide" as used herein refers to a polynucleotide of three or more but equal to or less than 300 nucleotides.

The term "DNA" or "deoxyribonucleic acid" as used herein indicates a polynucleotide composed of deoxyribonucleotide bases or an analog thereof to form an organic polymer. The term "deoxyribonucleotide" refers to any compounds that consist of a deoxyribose (deoxyribonucleotide) sugar joined to a purine or pyrimidine base and to a phosphate group, and that are the basic structural units of a deoxyribonucleic acid, typically adenine (A), cytosine (C), guanine (G), and thymine (T). In an DNA adjacent ribose nucleotide bases are chemically attached to one another in a chain typically via phosphodiester bonds. The term "deoxyribonucleotide analog" refers to a deoxyribonucleotide in which one or more individual atoms have been replaced with a different atom with a different functional group. For example, deoxyribonucleotide analogues include chemically modified deoxyribonucleotides, such as methylation hydroxymethylation glycosylation and additional modifications identifiable by a skilled person.

The term "RNA" or "ribonucleic acid" as used herein indicates a polynucleotide composed of ribonucleotide bases or an analog thereof linked to form an organic polymer. The term "ribonucleotide" refers to any compounds that consist of a ribose (ribonucleotide) sugar joined to a purine or pyrimidine base and to a phosphate group, and that are the basic structural units of a ribonucleic acid, typically adenine (A), cytosine (C), guanine (G), and uracil (U). In an RNA adjacent ribose nucleotide bases are chemically attached to one another in a chain typically via phosphodiester bonds.

In embodiments herein described separation can be performed of a mixture comprising a target compound and a nucleic acid at low concentrations. The wording "low concentrations" as used herein in connection with the amount of nucleic acid in a mixture to be separated indicates a concentration of 1 µM or less.

Examples of a solution with low concentrations of nucleic acids include single-cell sample, cell-free DNA, circulating tumor cell sample, pathogen diagnostics sample, SNP detection sample, or the like as will be understood by a person skill in the art. Additional examples of low concentration of target nucleic acids comprise sewage, pooled diagnostic samples, low volume patient samples (few µL), partially degraded samples (e.g. forensics, paleontology, poor storage conditions) and additional samples usually containing a low concentration of nucleic acid.

Exemplary mixtures comprising 1 uM or less nucleic acid, comprise collected samples containing 1-10 copies, 10-100 copies, 100-1000 copies, 1000-10,000 copies, 10,000-100,000 copies, 1E5-1E6 ($1\times10^5$ to $1\times10^6$) copies, 1E6-1E7 ($1\times10^6$ to $1\times10^7$) copies, 1E7-1E8 ($1\times10^7$ to $1\times10^8$) copies, 1E8-1E9 ($1\times10^8$ to $1\times10^9$) copies.

In some embodiments, wherein the mixture comprises NA at low concentration the nucleic acid retained in the matrix in an amount resulting from contacting the matrix with a mixture wherein nucleic acid is comprised in an amount of 1 uM or less. In those embodiments, the solid matrix can retain a nucleic acid min an amount of 100 ppm, 10 ppm, 1 ppm, 0.1 ppm, 0.01 ppm, 0.001 ppm, 0.0001 ppm, 0.00001 ppm relative to weight of the solid matrix.

The term "target compound" as used herein indicates a substance other than a nucleic acid formed by two or more chemical elements chemically bonded together. Typically, chemical bonds holding elements in a target compound in the sense of the disclosure comprise covalent bonds and noncovalent bonds. The term 'bond", "bind", "binding", as used herein indicates an attractive interaction between two elements which results in a stable association of the element in which the elements are in close proximity to each other. If each element is comprised in a molecule the result of binding is typically formation of a molecular complex. Attractive interactions in the sense of the present disclosure refer to non-covalent binding. Non-covalent bonding includes ionic bonds, hydrophobic interactions, electrostatic interactions, hydrogen bonds, and dipole-dipole bonds. Electrostatic interactions include association between two oppositely charged entities.

A target compound in the sense of the disclosure can comprise any inorganic or organic compound, wherein the term inorganic compound indicates a chemical compound that lacks C—H bonds, while the term "organic compound" indicates any chemical compound that contains carbon.

Accordingly, target inorganic compounds in the sense of the disclosure typically comprise inorganic salts composed of a metal ion (cation) and a non-metal ion (anion). Exemplary inorganic salts comprise binary salts such as calcium fluoride (CaF2), ternary salts wherein a metal ion combines with a polyatomic anion PAA, such as NaCl, MgCl2, KCl, KNO2, KNO3, MgSO4, or other inorganic salts identifiable by a skilled person.

A target organic compound in the sense of the disclosure typically comprises aliphatic or aromatic compounds and/or organic molecules comprising aliphatic and/or aromatic groups.

As used herein, the term "aliphatic" refers to an alkyl, alkenyl or alkynyl compound or group which can be a substituted unsubstituted and/or heteroatom containing, linear, branched or cyclic and can further be heteroatom containing. As used herein the term "alkyl" as used herein refers to a linear, branched, or cyclic, saturated hydrocarbon group formed by a carbon chain. As used herein the term "carbon chain" indicates a linear or branched line of connected carbon atoms. An alkyl carbon chain typically although not necessarily containing 1 to about 18 carbon atoms. As used herein the term "alkenyl" indicates a linear, branched, or cyclic hydrocarbon group that contains at least one carbon-carbon double bond. As used herein the term "alkynyl" indicates a linear, branched, or cyclic hydrocarbon group that contains at least one carbon-carbon triple bond.

As used herein, the term "aromatic" refers to a chemical compound or group containing a conjugated planar ring system with delocalized pi electron clouds instead of discrete alternating single and double bonds, such as an aryl or aralkyl compound which can be substituted or unsubstituted and/or heteroatom containing as will be understood by a skilled person. The term "aryl" as used herein, and unless otherwise specified, refers to an aromatic compound containing a single aromatic ring or multiple aromatic rings that are fused together, directly linked, or indirectly linked (such that the different aromatic rings are bound to a common group such as a methylene or ethylene moiety). Preferred aryl groups contain 5 to 12 carbon atoms, and particularly preferred aryl groups contain 5 to 6 carbon atoms. Exemplary aryl groups contain one aromatic ring or two fused or linked aromatic rings, e.g., phenyl, naphthyl, biphenyl, diphenylether, diphenylamine, benzophenone, and the like.

Unless otherwise indicated, the term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents. As used herein, a "substituent" is an atom or group of atoms substituted in place of a hydrogen atom on the main chain of a hydrocarbon, which can form a functional group.

The term "functional group" as used herein indicates specific groups of atoms within a molecular structure that are responsible for a characteristic chemical and physical property of that structure. Exemplary functional groups comprise hydroxyl, sulfhydryl, $C_1$-$C_{12}$ alkoxy, $C_2$-$C_{12}$ alkenyloxy, $C_2$-$C_{12}$ alkynyloxy, $C_5$-$C_{12}$ aryloxy, $C_6$-$C_{12}$ aralkyloxy, $C_6$-$C_{12}$ alkaryloxy, acyl (including $C_2$-$C_{12}$ alkylcarbonyl (—CO-alkyl) and $C_6$-$C_{12}$ arylcarbonyl (—CO-aryl)), acyloxy (—O-acyl, including $C_2$-$C_{12}$ alkylcarbonyloxy (—O—CO-alkyl) and $C_6$-$C_{12}$ arylcarbonyloxy (—O—CO-aryl)), $C_2$-$C_{12}$ alkoxycarbonyl (—(CO)—O-alkyl), $C_6$-$C_{12}$ aryloxycarbonyl (—(CO)—O-aryl), $C_2$-$C_{12}$ alkylcarbonato (—O—(CO)—O-alkyl), $C_6$-$C_{12}$ arylcarbonato (—O—(CO)—O-aryl), carboxy (—COOH), carboxylato (—COO$^-$), carbamoyl (—(CO)—NH$_2$), mono-($C_1$-$C_{12}$ alkyl)-substituted carbamoyl (—(CO)—NH($C_1$-$C_{12}$ alkyl)), di-($C_1$-$C_{12}$ alkyl)-substituted carbamoyl (—(CO)—N($C_1$-$C_{12}$ alkyl)$_2$), mono-($C_5$-$C_{12}$ aryl)-substituted carbamoyl (—(CO)—NH-aryl), di-($C_5$-$C_{12}$ aryl)-substituted carbamoyl (—(CO)—N($C_5$-$C_{12}$ aryl)$_2$), di-N—($C_1$-$C_6$ alkyl),N—($C_5$-$C_{12}$ aryl)-substituted carbamoyl, thiocarbamoyl (—(CS)—NH$_2$), mono-($C_1$-$C_{12}$ alkyl)-substituted thiocarbamoyl (—(CO)—NH($C_1$-$C_{12}$ alkyl)), di-($C_1$-$C_{12}$ alkyl)-substituted thiocarbamoyl (—(CO)—N($C_1$-$C_6$ alkyl)$_2$), mono-($C_5$-$C_{12}$ aryl)-substituted thiocarbamoyl (—(CO)—NH-aryl), di-($C_5$-$C_6$ aryl)-substituted thiocarbamoyl (—(CO)—N($C_5$-$C_6$ aryl)$_2$), di-N—($C_1$-$C_6$ alkyl),N—($C_5$-$C_6$ aryl)-substituted thiocarbamoyl, carbamido (—NH—(CO)—NH$_2$), cyano (—C≡N), cyanato (—O—C≡N), thiocyanato (—S—C≡N), formyl (—(CO)—H), thioformyl (—(CS)—H), amino (—NH$_2$), mono-($C_1$-$C_{12}$ alkyl)-substituted amino, di-($C_1$-$C_{12}$ alkyl)-substituted amino, mono-($C_5$-$C_{12}$ aryl)-substituted amino, di-($C_5$-$C_6$ aryl)-substituted amino, $C_2$-$C_{12}$ alkylamido (—NH—(CO)-alkyl), $C_6$-$C_{12}$ arylamido (—NH—(CO)-aryl), imino (—CR=NH where R=hydrogen, $C_1$-$C_{12}$ alkyl, $C_5$-$C_{12}$ aryl, $C_6$-$C_{12}$ alkaryl, $C_6$-$C_{12}$ aralkyl, etc.), $C_2$-$C_{12}$ alkylimino (—CR=N(alkyl), where R=hydrogen, $C_1$-$C_{12}$ alkyl, $C_5$-$C_{12}$ aryl, $C_6$-$C_{12}$ alkaryl, $C_6$-$C_2$ aralkyl, etc.), arylimino (—CR=N(aryl), where R=hydrogen, $C_1$-$C_{12}$ alkyl, $C_5$-$C_{12}$ aryl, $C_6$-$C_{12}$ alkaryl, $C_6$-$C_{12}$ aralkyl, etc.), nitro (—NO$_2$), nitroso (—NO), sulfo (—SO$_2$—OH), sulfonato (—SO$_2$—O$^-$), $C_1$-$C_{12}$ alkylsulfanyl (—S-alkyl; also termed "alkylthio"), $C_5$-$C_{12}$ arylsulfanyl (—S-aryl; also termed "arylthio"), $C_1$-$C_{12}$ alkylsulfinyl (—(SO)-alkyl), $C_5$-$C_{12}$ arylsulfinyl (—(SO)-aryl), $C_1$-$C_{12}$ alkylsulfonyl (—SO$_2$-alkyl), $C_5$-$C_{12}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O—)$_2$), phosphinato (—P(O)(O—)), phospho (—PO$_2$), phosphino (—PH$_2$), silyl (—SiR$_3$ wherein R is hydrogen or hydrocarbyl), and silyloxy (—O-silyl); and the hydrocarbyl moieties $C_1$-$C_{12}$ alkyl (preferably $C_1$-$C_{12}$ alkyl, more preferably $C_1$-$C_6$ alkyl), $C_2$-$C_{12}$ alkenyl (preferably $C_2$-$C_{12}$ alkenyl, more preferably $C_2$-$C_6$ alkenyl), $C_2$-$C_{12}$ alkynyl (preferably $C_2$-$C_{12}$ alkynyl, more preferably $C_2$-$C_6$ alkynyl), $C_5$-$C_{12}$ aryl (preferably $C_5$-$C_{12}$ aryl), $C_6$-$C_{12}$ alkaryl (preferably $C_6$-$C_{12}$ alkaryl), and $C_6$-$C_{12}$ aralkyl (preferably $C_6$-$C_{12}$ aralkyl), halo (such as F, Cl, Br, I), haloalkyl (such as $CCl_3$ or $CF_3$). Exemplary substituents also comprise one or more of the following groups: halo (such as F, Cl, Br, or I), haloalkyl (such as $CCl_3$ or $CF_3$), alkoxy, alkylthio, hydroxy, carboxy, carbonyl, epoxy, alkyloxycarbonyl, alkylcarbonyloxy, amino, carbamoyl, urea, alkylurea or thiol and additional groups identifiable by a skilled person upon reading of the present disclosure.

Accordingly, the term "substituted alkyl" refers to an alkyl moiety substituted with one or more substituent groups, Similarly, the term "substituted aryl" refers to an aryl moiety substituted with one or more substituent groups. For example, substituted alkyl comprise aralkyl and substituted aryl comprise alkaryl compound or group. The term "aralkyl" as used herein refers to an alkyl group with an aryl substituent, and the term "alkaryl" as used herein refers to an aryl group with an alkyl substituent, wherein "aryl" and "alkyl" are as defined above. In some embodiments, alkaryl and aralkyl groups contain 6 to 12 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, and the like. The terms "alkaryloxy" and "aralkyloxy" refer to substituents of the formula —OR wherein R is alkaryl or aralkyl, respectively, as defined.

As used herein the terms "heteroatom-containing" or "hetero-" indicated in connection with a group, refers to a hydrocarbon group in which one or more carbon atoms is replaced with an atom other than carbon, e.g., nitrogen, oxygen, sulfur, phosphorus or silicon. Exemplary "heteroatoms" comprise such as N, O, S, and P, and can be present in a compound by a covalent bond to each of two carbon atoms, thus interrupting the two carbon atoms. Accordingly, the term "heteroalkyl" refers to an alkyl substituent or group that is heteroatom-containing, the term "heterocyclic" refers to a cyclic substituent that is heteroatom-containing, the terms "heteroaryl" and "heteroaromatic" respectively refer to "aryl" and "aromatic" substituents or groups that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkyl ethers, secondary and tertiary alkyl amines, amides, alkyl sulfides, alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, and addition group identifiable by a skilled person.

Accordingly, the term "heteroatom-containing alkyl" and "heteroalkyl" refer to alkyl compounds or groups in which at least one carbon atom is replaced with a heteroatom, such as nitrogen, oxygen or sulfur. Similarly, the terms "heteroatom-containing aryl" and "heteroaryl" refer to aryl compounds or groups in which at least one carbon atom is replaced with a heteroatom, such as nitrogen, oxygen or sulfur.

The terms "cyclic", "cycle" and "ring" when referred to a group of atoms refer to alicyclic or aromatic groups that in some cases can be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic. Accordingly, the term "cycloalkyl" refers to a cyclic alkyl group, typically having 3 to 8, preferably 5 to 7, carbon atoms such as cyclohexyl group. "Heterocycloalkyl" refers to a saturated or partially saturated monocyclic, bicyclic, or polycyclic ring in which at least one carbon atom is replaced with a heteroatom selected from S, O, P and N, preferably from 1 to 3 heteroatoms in at least one ring.

Exemplary organic compounds or molecules comprising an aliphatic or aromatic group which can be target compounds in the sense of the disclosure comprise amino acids, mono and disaccharides, lipids such as cholesterol as well as more complex molecules such as proteins, fatty acids, phospholipids and polysaccharides as will be understood by a skilled person.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to forma polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In particular in some embodiments, a target compound can be a natural or unnatural aminoacids, derivative of natural aminoacids, oligopeptide and/or a protein. Exemplary aminoacid includes D or L-Alanine, D or L-Arginine, D or L-Asparagine, D or L-Aspartic acid, D or L-Cysteine, D or L-Glutamic acid, D or L-Glutamine, Glycine, D or L-Histidine, D or L-Isoleucine, D or L-Leucine, D or L-Lysine, D or L-Methionine, D or L-Phenylalanine, D or L-Proline, D or L-Serine, D or L-Threonine, D or L-Tryptophan, D or L-Tyrosine, and D or L-Valine.

The term saccharide as used herein indicates a biomolecule consisting of carbon (C), hydrogen (H) and oxygen (O) atoms, usually with a hydrogen-oxygen atom ratio of 2:1 with an empirical formula $Cm(H2O)n$ where m may be different from n. In some embodiments, a target compound can be a monosaccharide, disaccharide or a polysaccharide. Exemplary monosaccharides include glucose (dextrose), fructose (levulose), and galactose. Examples of disaccharides includes sucrose and lactose. Examples of polysaccharides includes cellulose and starch.

In some embodiment, the target compound can be a protein. The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. A polypeptide of at least two amino acids and up to 50 amino acids as used herein is defined as a peptide.

Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$— group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immuno precipitation, and a variety of other methods as understood by a person skilled in the art. Proteins can be provided in vitro or in vivo by several methods identifiable by a skilled person.

In some embodiment, the target compound can be a fatty acid. The term "fatty acid" as used herein refers to a carboxylic acid with a long aliphatic chain which is either saturated having no double or triple bonds or unsaturated having at least one double or triple bond. Typically having 4 or more carbon atoms and less than 30 carbon atoms and their modified derivatives. Example classes of fatty acids include ω-3, ω-6, ω-7, and ω-9. Exemplary fatty acids comprise arachidic acid, stearic acid, palmitic acid, erucic acid, oleic acid, linolenic acid, linoleic acid, and arachidonic acid. Exemplary material comprising fatty acids are lard, butter, coconut oil, sunflower oil, palm oil, cottonseed oil, soybean oil, olive oil, and corn oil.

In some embodiment, the target compound can be a phospholipid. Phospholipids are a subclass of fatty acid. Examples include docosahexaenoic acid (DHA), eicosapentaenoic acid (EPA), phosphatidic acid, phosphatidylethanolamine, phosphatidylcholine, phosphatidylserine, phosphoinositides, ceramide phosphorylcholine, ceramide phosphorylethanolamine, and ceramide phosphryllipid.

In some embodiment, the target compound can be a polysaccharide. The term "polysaccharide" as used herein indicates a polymeric carbohydrate molecule composed of long chains of monosaccharide units bound together by glycosidic linkages, and on hydrolysis give the constituent monosaccharides or oligosaccharides. Polysaccharide ranges in structure from linear to highly branched. Exemplary polysaccharide comprise starch, glycogen, cellulose, chitin, amylose, amylopectin, callose, laminarin, chrysolaminarin, xylan, arabinoxylan, mannan, fucoidan, and galactomannan.

In several embodiments herein described the target compounds can be or comprise impurities such as contaminants or remnants of previous physical or chemical reactions of the mixture which are either naturally occurring or added during synthesis of a chemical or commercial product. Impurities in the sense of the disclosure comprise any chemical substance that can be purposely, accidentally, inevitably, or incidentally added into the mixture.

For example, in some embodiment, the target compound can comprise a chaotropic agent selected from n-butanol, ethanol, guanidinium thiocyanate, guanidinium chloride, lithium perchlorate, lithium acetate, magnesium chloride, phenol, 2-propanol, sodium dodecyl sulfate, thiourea, and urea.

Similarly, in some embodiments, a target compound can comprise a buffer agent such as phosphate buffer saline, N-(2-Acetamido)-aminoethanesulfonic acid (ACES), Salt of acetic acid (Acetate), N-(2-Acetamido)-iminodiacetic acid (ADA), 2-Aminoethanesulfonic acid, Taurine (AES), Ammonia, 2-Amino-2-methyl-1-propanol (AMP), 2-Amino-2-methyl-1,3-propanediol, (Ammediol or AMPD), N-(1,1-Dimethyl-2-hydroxyethyl)-3-amino-2-hydroxypropanesulfonic acid (AMPSO), N,N-Bis-(2-hydroxyethyl)-2-aminoethanesulfonic acid (BES), Sodium Bicarbonate, N,N'-Bis(2-hydroxyethyl)-glycine (Bicine), [Bis-(2-hydroxyethyl)-imino]-tris-(hydroxymethylmethane) (BIS-Tris), 1,3-Bis[tris(hydroxymethyl)-methylamino]propane) (BIS-Tris-Propane), Boric acid, Dimethylarsinic acid (Cacodylate), 3-(Cyclohexylamino)-propanesulfonic acid (CAPS), 3-(Cyclohexylamino)-2-hydroxy-1-propanesulfonic acid (CAPSO), Sodium carbonate, Cyclohexylaminoethanesulfonic acid (CHES), Salt of citric acid (Citrate), 3-[N-Bis(hydroxyethyl)amino]-2-hydroxypropanesulfonic acid (DIPSO), Formate Salt of formic acid, Glycine, Glycylglycine, N-(2-Hydroxyethyl)-piperazine-N'-ethanesulfonic acid (HEPES), N-(2-Hydroxyethyl)-piperazine-N'-3-propanesulfonic acid (HEPPS, EPPS), N-(2-Hydroxyethyl)-piperazine-N'-2-hydroxypropanesulfonic acid (HEPPSO), Imidazole, Salt of malic acid (Malate), Maleate Salt of maleic acid, 2-(N-Morpholino)-ethanesulfonic acid (MES), 3-(N-Morpholino)-propanesulfonic acid (MOPS), 3-(N-Morpholino)-2-hydroxypropanesulfonic acid (MOPSO), Salt of phosphoric acid (Phosphate), Piperazine-N,N'-bis(2-ethanesulfonic acid) (PIPES), Piperazine-N,N'-bis(2-hydroxypropanesulfonic acid) (POPSO), Pyridine, Salt of succinic acid (Succinate), 3-{[Tris(hydroxymethyl)-methyl]-amino}-propanesulfonic acid (TAPS), 3-[N-Tris(hydroxymethyl)-methylamino]-2-hydroxypropanesulfonic acid (TAPSO), Triethanolamine (TEA), 2-[Tris(hydroxymethyl)-methylamino]-ethanesulfonic acid (TES), N-[Tris(hydroxymethyl)-methyl]-glycine (Tricine), and Tris(hydroxymethyl)-aminomethane (Tris).

In some embodiments, the target compound can comprise a constituent in a biological medium. An exemplary biological medium includes glucose, monobasic ammonium phosphate, sodium chloride, magnesium sulfate, and potassium phosphate. A further exemplary biological medium includes peptone, beef extract and agar lysogeny broth, yeast extract, blood agar, chocolate agar, and fastidious broth.

In some embodiments, a target compound can be a growth inhibitor to an organism such as gentian violet, bile salts, sodium desoxycholate to gram positive organism, potassium tellurite and sodium azide to a gram-negative organism, chloral hydrate and ethanol to a *proteus*.

In some embodiments, a target compound can be an antibiotic including but not limited to penicillin, streptomycin, cephalosporins, polymyxins rifamycins, lipiarmycins, quinolones, sulfonamides, macrolides, lincosamides tetracyclines, bactericidal aminoglycosides, cyclic lipopeptides (such as daptomycin), glycylcyclines (such as tigecycline), oxazolidinones (such as linezolid), and lipiarmycins (such as fidaxomicin), fluoroquinolones, or malachite green.

In some embodiment, a target compound can comprise any component of a lysis buffer (exemplary components comprise 2-mercaptoethanol, phenol, chaotropic salts such as guanidinium isothiocyanate, buffer salts such as Tris-HCl, ionic salts such as NaCl, detergents such as Triton X-100 or Sodium dodecyl sulfate, proteinases such as proteinase K, reducing agents such as dithiothreitol). Exemplary lysis buffers comprising target compounds in the sense of the disclosure comprise Qiagen commercial examples include: Qiagen buffer RLT, Qiagen buffer RLT plus, Qiagen buffer AL, Qiagen buffer ASL, Qiagen buffer ATL, Qiagen buffer P2, Zymo commercial examples include: Zymo DNA/RNA Lysis Buffer, Zymo RNA lysis buffer, Zymo YR lysis buffer, Zymo S/F RNA lysis buffer, and additional lysis buffers identifiable by a skilled person upon reading of the present disclosure.

In some embodiment, a target compound can comprise any component of a wash buffer (examples include ethanol, isopropanol, and salt additives). Exemplary lysis buffers comprising target compounds in the sense of the disclosure comprise Qiagen commercial examples include: Qiagen buffer PE, Qiagen buffer QC, Qiagen buffer RPE, Qiagen buffer RW1, Zymo commercial examples include: Zymo DNA wash buffer, Zymo RNA wash buffer, Zymo DNA/RNA wash buffer, and additional lysis buffers identifiable by a skilled person upon reading of the present disclosure.

In some embodiment, a target compound can comprise any components of a sample as will be understood by a skilled person. Exemplary target compounds that can be included in a sample comprise bile salts, complex polysaccharides, collagen, heme, humic acid, melanin and eumelanin, myoglobin, polysaccharides, proteinases, calcium ions, urea, hemoglobin, lactoferrin, immunoglobin G, indigo dye, and additional target compounds identifiable by a skilled person upon reading of the present disclosure.

In embodiments herein described methods and systems of the instant disclosure separation of the mixture comprising the nucleic acid and the target compound is performed with a solid matrix.

The wording "solid matrix" as used herein indicates a solid material configured to retain the nucleic acid and the target compounds through the related sorption to the solid material. In particular, a solid material forming a solid matrix in the sense of the disclosure is configured to allow adsorption, and/or ion exchange of the nucleic acid or the target compound to the solid material. Exemplary solid matrix includes silica, polymer network or gel.

In some embodiments, the solid matrix has a spherical shape of a diameter ranging from 0.01 millimeter to 1 meter.

In some embodiments, the solid matrix has a cylindrical shape of a diameter ranging from 0.01 millimeter to 1 meter and a longitudinal dimension ranging from 0.01 millimeter to 1 meter.

The term "adsorption" as used herein indicates adhesion of atoms, ions or molecules from a gas, liquid or dissolved solid to a surface [Ref.: "Glossary". The Brownfields and Land Revitalization Technology Support Center. Retrieved 2009-12-21] such as adhesion of a target compound to a surface of the solid material of the matrix. In particular, nucleic acids and/or target compound can adsorb to the matrix.

The term "ion exchange" as used herein indicates an exchange of ions between two electrolytes or between an electrolyte solution and a complex. In particular, in embodiments of the disclosure the solid material can be used as an "ion exchanger" which exchange positively charged ions (cations), negatively charged ions (anions) or both with the mixture under separation as will be understood by a skilled person.

In some embodiments, the solid material of the solid matrix herein described comprises silica, such as silica gel, including silican spherical and irregular particle shape, as well as bare and modified/bonded silica products, in various grades, particle and pore sizes identifiable by a skilled person.

In particular in some embodiments, the silica material of the solid matrix can comprises a gel particle, glass particle, glass microfiber or slurry. In some embodiments, the glass particle can comprise a powder, microbead, silicate glass, flint glass, borosilicate glass, or glass fiber filter.

Binding of the nucleic acids and/or target compounds to the silica matrix can be performed through van der Waals forces (nonpolar interactions), dipole-dipole interactions (polar interactions), and hydrogen bonding. It is believed sodium ions play a role in facilitating the interactions between silica and the negatively charged oxygen on the nucleic acid's phosphate group. Without being bound by any specific theory, it is believed phosphate-silanol and hydrophobic interactions enable binding of nucleic acids to silica. Exemplary silica includes silica membranes, silica fibers, borosilicate glass fibers, borosilicate glass, borosilicate microfiber, and silica coated magnetic particles.

In some embodiments, the solid matrix comprises a solid material configured for ion exchange. In an ion exchange solid matrix, a cationic or anionic functional group is presented on the material forming the solid matrix. In the ion exchange solid matrix the cationic or anionic functional group is capable of electrostatic interaction with an ionic species of opposite charge. For example, an anionic exchange solid matrix is capable of electrostatically interacting with an ion of opposite charged species such as a nucleic acid.

In some embodiments, the anion exchange solid matrix comprises a cationic group represented by Formula (IV):

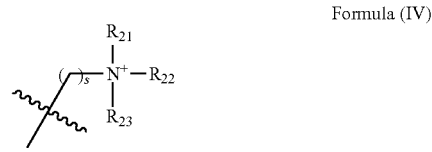

Formula (IV)

wherein
s is 1 to 6,
R21, R22, and R23 are independent selected from H, linear, branched, substituted or unsubstituted a lower alkyl group (C1-C4), a lower alkenyl group or a lower alkynyl group.

A lower alkyl group as used herein contains 1 to 4 carbon atoms (C1-C4), such as methyl, ethyl, n-propyl, isopropyl, n-butyl, isobutyl, t-butyl, and the like, as well as cycloalkyl groups such as cyclopropyl, cyclobutyl groups.

A lower alkenyl group as used herein contains 3 to 4 carbon atoms (C3-C4) and a C—C double bond, such as propenyl, butenyl, groups.

A lower alkynyl group as used herein contains 3 to 4 carbon atoms (C3-C4) and a C—C triple bond.

The anion functional group on the anion exchange resin or silica can be a tertiary or quaternary ammonium. An exemplary a tertiary ammonium can be a DEAE (diethylaminoethyl) wherein s is 2 and R21 and R22 are ethyl and R23 is a proton.

In some embodiments, the solid matrix comprises a resin, and s is 2 and R21 and R22 are ethyl groups and R23 is a proton.

Solid matrix comprising solid material configured for ion exchange can be unselective or have binding preferences for certain ions or classes of ions, depending on their chemical structure, depending on the size of the ions, their charge, or their structure. Typical examples of ions that can bind to ion exchangers are H+, OH—, singly charged inorganic ions like Na+, K+, and Cl−, doubly charged inorganic ions like Ca2+ and Mg2+, polyatomic inorganic ions like $SO_4^{2-}$ and $PO_4^{3-}$, organic bases, usually molecules containing the amine functional group —$NR_2H^+$, organic acids, often molecules containing —COO— (carboxylic acid) functional groups and ionized organic molecules such amino acids, peptides, proteins and additional compound identifiable by a skilled person.

In some embodiments, the solid matrix has a cylindrical shape of a diameter ranging from 0.1 millimeter to 1 meter and a longitudinal dimension ranging from 0.1 millimeter to 1 meter.

In some embodiments, the solid matrix has a volume of 1 nanoliter to 1 L.

In some embodiments, the solid matrix has a solid matrix volume, the removing agent has a removing agent volume, wherein the removing agent volume is 1 to 100,000 times or more of the solid matrix volume; and wherein the removing agent is eluted through the solid matrix at a flow rate of 100 nanoliters per second to 10 milliliter per second.

In some embodiments, the solid matrix can include silica in the form of gel particles, glass particles, glass fiber, glass microfibers or slurry resins, wherein the glass particles in turn can be in the form of powder, microbeads, silicate glass, flint glass, borosilicate glass, or glass fiber filters.

In some embodiments, the solid matrix the solid matrix further comprises magnetic material encoated by the silica.

In some embodiments, the solid matrix further comprises magnetic material encoated by the silica wherein magnetic material comprises iron oxide (Fe3O4).

In some embodiments, the solid matrix comprises a silica wherein the silica comprises a gel particle, glass particle, glass microfiber, glass fiber filter, slurry, magnetic beads, paramagnetic beads, superparamagnetic beads, SPRI beads or any combination thereof.

In some embodiments, a solid matrix comprising glass fiber solid matrix can take the form of a packed column, or a packed filter configured for insertion within a microfluidic device, a packed filter configured for insertion in a centrifuge tube, or silica-coated magnetic particles in suspension.

In embodiments herein described methods and systems of the instant disclosure separation of a source mixture comprising target compound and a nucleic acid with a solid matrix are directed to separate the nucleic acid from one or more target compounds having a water solubility equal to or greater than 0.001 g per 100 mL.

The wording "solubility" as used herein indicates a chemical property referring to the ability for a chemical substance, the solute, to dissolve in a solvent. Accordingly, solubility is a measure of the amount of the solute that can dissolve in a solvent at a specific temperature. Accordingly, solubility is can be measured in terms of the maximum amount of solute dissolved in a solvent at equilibrium. Solubility can be measured in various units of concentration such as molarity, molality, mole fraction, mole ratio, mass (solute) per volume(solvent) and other units identifiable by a skilled person.

In particular, solubility of a first compound in a second compound can be measured by weighing a specific mass of the first compound and adding the second compound to the weighed specific mass of the first compound, in small increments. The mass at which the second compound does not dissolve into the first compound or does not form a homogeneous solution with the first compound is used to determine the solubility of the first compound in the second compound.

In some embodiments, methods and systems herein described are directed to selectively remove one or more target compounds having a water solubility equal to or greater than 0.001 g per 100 mL at 25° C. at 1 atm pressure from a solid matrix further retaining a nucleic acid. In those embodiments, selective removal of the target compound can be performed by contacting the solid matrix with a target compound removing agent having a water solubility equal to or less than 0.05 g per 100 mL at 25° C. at 1 atm pressure with water having a solubility in the removing agent of less than 10 g per 100 mL at 25° C. at 1 atm pressure, the contacting performed to remove the target compound from the solid matrix. In particular, in methods herein described the contacting the solid matrix with a target compound removing agent comprises eluting the target compound from the solid matrix by washing the solid matrix with the target compound removing agent.

The wording "removing agent" as used herein indicates an organic compound having physico chemical properties allowing an interaction with a reference compound in the solid matrix in the sense of the disclosure, which results in the removal of the reference compound from the solid matrix. Accordingly a removing agent can be a target compound removing agent for removing a target compound from a solid matrix. A removing agent can be a nucleic acid removing agent for removing a nucleic acid from a solid matrix. A nucleic acid removing agent is also term eluent as described herein.

In particular a removing agent capable of removing a target compound in the sense of the disclosure having a water solubility equal to or greater than 0.001 g per 100 mL at 25° C. at 1 atm pressure typically refers to organic solvent comprising at least one organic compound which contains at least 9 carbons and has a water solubility equal to or less than 0.05 g per 100 mL at 25° C. at 1 atm pressure with water having a solubility in the removing agent of less than 10 g per 100 mL at 25° C. at 25° C. at 1 atm pressure.

In some embodiments, the solubility in water of the removing agent selected to remove a target compound is equal to or less than 0.01 g per 100 mL at 25° C. at 1 atm pressure, equal to or less than 0.001 g per 100 mL at 25° C. at 1 atm pressure, equal to or less than 0.0001 g per 100 mL at 25° C. at 1 atm pressure, equal to or less than 0.00001 g per 100 mL at 25° C. at 1 atm pressure, equal to or less than 0.000001 g per 100 mL, at 25° C.

A skilled person will be able to identify a suitable removing agent based on the physico chemical properties of the target compound to be removed and the related attachment to the solid matrix.

In some embodiment, the target compound removing agent has a water solubility equal to or less than 0.015 g per 100 mL at 25° C. at 1 atm pressure, equal to or less than 0.0015 g per 100 mL at 25° C. at 1 atm pressure, equal to or less than 0.00015 g per 100 mL at 25° C. at 1 atm pressure, equal to or less than 0.000015 g per 100 mL at 25° C. at 1 atm pressure.

In preferred embodiments, a target compound removing agent to be used in methods and systems of the disclosure comprises removing agents having a water solubility from 0.0001 mg/100 mL to 0.02 g/100 mL per 100 mL of water at 25° C. at 1 atm pressure and more preferably from 0.0002 g/100 mL to 0.002 g/100 mL per 100 mL of water at 25° C. at 1 atm pressure.

Accordingly, in some embodiments, in the method of selectively removing one or more target compounds, the target compound removing agent can comprises a compound further having a solubility in ethanol at 25° C. at 1 atm pressure of at least 1 wt %, at least 5 wt %, at least 10 wt %, at least 20 wt %, at least 50 wt %, or at least 90 wt %.

In some embodiments, in the method of selectively removing one or more target compounds, the target compound removing agent can comprises a compound further having a solubility of equal to or less than 0.05 wt % in water at 25° C. at 1 atm pressure and a solubility in ethanol at 25° C. at 1 atm pressure of at least 1 wt %, at least 5 wt %, at least 10 wt %, at least 20 wt %, at least 50 wt %, or at least 90 wt %.

In some embodiments, the method comprises: contacting the solid matrix with a target compound removing agent having a water solubility less than 0.05 g per 100 mL at 20° C. at 1 atm pressure, preferably equal to or less than 0.03 g per 100 mL at 25° C. at 1 atm pressure with water having a solubility in the removing agent of less than 5 g per 100 mL.

In preferred embodiments, the target compound removing agent further has a solubility in ethanol at 25° C. at 1 atm pressure of at least 1 wt %, at least 5 wt %, at least 10 wt %, at least 20 wt %, at least 50 wt %, or at least 90 wt %. In those embodiments the target removing agent can have a solubility of equal to or less than 0.05 wt % in water at 25° C. at 1 atm pressure and a solubility in ethanol at 25° C. at 1 atm pressure of at least 1 wt %, at least 5 wt %, at least 10 wt %, at least 20 wt %, at least 50 wt %, or at least 90 wt %.

In some embodiments, the removing agent is selected from a group of pH neutral target removing agents encompassing compounds with water solubility, and such that upon contact with pure (pH=7) water in up to 1:1 mass ratio, they do not change the pH of the water by more than 1 unit, more than 0.5 units, more than 0.2 units, more than 0.1 units.

Accordingly as used herein, a removing agent is defined as being "pH neutral" when upon contact with pure (pH=7) water in up to 1:1 mass ratio, they do not change the pH of the water by more than 2 units, 1 unit, more than 0.5 units, more than 0.2 units, more than 0.1 units. In some embodiments, a pH neutral removing agent has a water solubility equal to or less than 10 g per 100 mL. A pH neutral target compound removing agent is expected to minimize an increase of solubility of nucleic acid on solid matrix due to protonation or deprotonation of the nucleic acid and thus increase the recovery of the nucleic acid. Therefore, in the method to selectively remove a target compound by contacting the solid matrix with a pH neutral target compound removing agent, the solid matrix retains at least 10%, 20%, 30%, 50%, 75%, 90%, 95%, 98%, 99%, 99.5%, 99.8%, 99.9%, or 99.99% of the nucleic acid.

In some embodiments, the target compound removing agent allows selective removal of target compounds in lysis buffers, wash buffers, as well as PCR reaction inhibitors present in samples including inhibitors in saliva, mucous, blood, urine, feces, sewage, foods, humic acids, mucous, and the like as will be understood by a person skilled in the art.

In some embodiments, the target compound removing agent allows selective removal of target compounds selected target compound comprises a buffer agent, an antibiotic, a saccharide, an amino acid, a peptide, a protein or a salt, lysis buffer agent, wash buffer agent, wash buffer agent containing 60-80% ethanol, 100% ethanol, phenols, humic acids, urea, proteases, calcium ions, potassium ions, chloride ions, sodium ions, sodium deocycholate, sodium dodecyl sulfate, sarkosyl, isopropanol, bile salts, collagen, heme, melanin, eumelanin, myoglobin, lactoferrin, hemoglobin, immunoglobin G, indigo dye, tannic acid, antivirals, heparin, hormones, lipids, urate, algae, glycogen, pectin, xylans, fulmic acids, metal ions, bone dust, peat extract, ethylenediaminetetraacetic acid, cell debris, or detergents or any combination thereof.

In some embodiments, the target compound removing agent allows selective removal of target compounds comprising a chaotropic agent selected from the group consisting of n-butanol, ethanol, guanidinium thiocyanate, guanidinium chloride, lithium perchlorate, lithium acetate, magnesium chloride, phenol, 2-propanol, sodium dodecyl sulfate, thiourea, and urea.

In some embodiments, the target compound removing agent is selected to inhibit a target enzyme catalyzing the target biochemical reaction of the nucleic acid by a rate of less than 5%.

In some embodiments, ethanol has a solubility in the target removing agent at 25° C. at 1 atm pressure of at least 1 g per 100 mL, 3 g per 100 mL, 10 g per 100 mL, 30 g per 100 mL, 50 g per 100 mL, 70 g per 100 mL, or 90 g per 100 mL of the solution and therefore the target removing agent can remove ethanol from a solid matrix.

Exemplary pH neutral removing agents includes any target removing agent comprises a compound of formula (XI)

$$C_{m'}·H_{(2m'+2-2d-n)}(OH)_n \qquad (XI)$$

wherein
m' is the number of carbon atoms on the main ranging from 9 to 34,
d is the degree of unsaturation ranging from 0 to 4,
n is 1, 2 or 3.

In particular, exemplary pH neutral target compound removing agent includes 1-undecanol and/or 2-dodecanol.

In some embodiments, a pH neutral removing agent has a water solubility equal to or less than 10 g per 100 mL at 25° C. at 1 atm pressure. In particular, pH neutral removing agent has a water solubility equal to or less than 4.0 g per 100 mL at 25° C. at 1 atm pressure as exemplified in Table 7.

In some embodiment, the pH neutral target compound removing agent comprises substituted or unsubstituted linear or branched pH neutral alcohols having at least 9 carbon atoms. Preferably, the pH neutral removing agent includes 1-nonanol, 1-decanol, 1-undecanol, 1-dodecanol, and 2-dodecanol. In particularly, 1-decanol, and 2-dodecanol.

Preferably, the pH neutral removing agent has a water solubility of 0.0001 to 0.01 g per 100 mL at 25° C. at 1 atm pressure as exemplified in Example 16 (see in particular Table 7).

Therefore, in the method to selectively remove a target compound by contacting the solid matrix with a pH neutral target compound removing agent, the solid matrix retains at least 10%, 20%, 30%, 50%, 75%, 90%, 95%, 98%, 99%, 99.5%, 99.8%, 99.9%, or 99.99% of the nucleic acid.

In some of embodiments of the method to selectively remove a target compound by contacting the solid matrix with a pH neutral target compound removing agent, the pH neutral target compound removing agent allows selective removal of lysis buffers, wash buffers, and PCR reaction inhibitors present in samples including inhibitors in saliva, mucous, blood, urine, feces, sewage, foods, humic acids, mucous, and the like as will be understood by a person skilled in the art.

In some embodiment, the removing agent is selected from the group consisting of caprylic acid, capric acid, lauric acid, myristic acid, palmitic acid, or stearic acid, cis oleic acid, trans oleic acid, or a combination thereof. Particularly, the carboxylic acid group of the removing agent is expected to increase hydrogen bonding interaction or electrostatic charge interaction with the target compound and allow effective removal of target compound containing an amine group, mercapto group, hydroxyl group, amide group, carboxylic acid group or any polar group capable of hydrogen bonding interaction or electrostatic charge interaction with a carboxylic acid. Accordingly, it is expected that some of these embodiments will have an increased hydrogen bonding and improved removal of certain target compound such as beta-mercaptoethanol as compared to the efficiency of pH neutral alcohols.

In some embodiment, the removing agent is selected from the group consisting of myristoleic acid, palmitoleic acid, sapienic acid, oleic acids, elaidic acid, vaccenic acid, linoleic acid, linoelaidic acid, and α-linolenic acid, or a combination thereof. Particularly, the carboxylic acid group of the removing agent may increase hydrogen bonding interaction or electrostatic charge interaction with the target compound and allows effective removal of target compound containing an amine group, mercapto group, hydroxyl group, amide group, carboxylic acid group or any polar group capable of hydrogen bonding interaction or electrostatic charge interaction with a carboxylic acid. It is expected that some of these embodiments will have an increased hydrogen bonding and improved removal of certain target compound as compared to the efficiency of pH neutral alcohols.

In some embodiment, the removing agent is selected from the group consisting of palm oil, coconut oil, canola oil, soybean oil, sunflower oil, rapeseed oil, peanut oil, cotton seed oil, palm kernel oil, and olive oil, or a combination thereof.

In some embodiment, in the method to selectively remove a target compound by contacting the solid matrix with a pH neutral target compound removing agent, the solid matrix retains at least 10%, 20%, 30%, 50%, 75%, 90%, 95%, 98%, 99%, 99.5%, 99.8%, 99.9%, or 99.99% of the nucleic acid, wherein the pH neutral target compound removing agent is selected from the group consisting of palm oil, coconut oil, canola oil, soybean oil, sunflower oil, rapeseed oil, peanut oil, cotton seed oil, palm kernel oil, and olive oil, or a combination thereof.

In some embodiment, the target compound removing agent is an organic compound of Formula (X):

$$C_mH_{(2m+2-2d-i-j-k)}Q_i^a Q_j^b Q_k^c \qquad \text{Formula (X)}$$

wherein
m is the number of carbon atoms on the main ranging from 2 to 34,
d is the degree of unsaturation ranging from 0 to 4, wherein m is equal to or larger than 2 d,
$Q^a$, $Q^b$ and $Q^c$ are each independently a functional group selected from the group consisting of hydroxyl, thiol, fluoro, chloro, bromo, iodo, cyano (—C≡N), nitro (—NO2), nitroso (—NO), sulfinyl (R'S(O)—), sulfonyl (R'S(O2)-), carbonyl (R'—CO—), carbonyloxy (R'—CO2-), oxycarbonyl (—CO2R'), oxy (R'—O—), amido (R'—CO—NR"—), carbamoyl (—CO—NR'R"), imido (R'CO—N(R"CO)—), carbamido (NR'R"CONR'"—), carbonato (R'OCO2-),
wherein R', R" and R'" are each independently a hydrogen (H) or a C1-C12 alkyl, C2-C12 alkenyl, C2-C12 alkynyl, C7-C12 aralkyl, or C7-C12 alkaryl group,
i, j, and k are the numbers of $Q^a$, $Q^b$ and $Q^c$ respectively, wherein i, j, and k are each 0, 1 or 2 and at least one of i, j and k is 1 or 2.

In some embodiments, R', R" and R'" of Formula (X) as described herein are each independently a hydrogen, an intermediate alkyl group, an intermediate alkenyl group, or a intermediate alkynyl group.

An intermediate alkyl group as used herein contains 5 to 8 carbon atoms (C5-C8), such as amyl, pentyl, hexyl, hepty and the like, as well as cycloalkyl groups such as cyclohexyl group.

An intermediate alkenyl group as used herein contains 5 to 8 carbon atoms (C5-C8) and at least one C—C double bond.

An intermediate alkynyl group as used herein contains 5 to 8 carbon atoms (C5-C8) and at least one C—C triple bond. As used herein, the portion of $C_mH_{(2m+2-2d-i-j-k)}$ in Formula (X) is the hydrophobic backbone of the removing agent and $Q^a$, $Q^b$ and $Q^c$ in Formula (X) are the polar group of the removing agent. In general, the more carbon atoms (m) in the hydrophobic backbone, the less solubility of the target compound removing agent in water.

The wording "degree of unsaturation", d, as used herein refers to the number of carbon-carbon double bonds or its equivalents. Therefore, a double bond corresponds to d of 1, a triple bond corresponds to d of 2, a cyclic ring corresponds to d of 1. A benzene ring corresponds to to d of 4.

In general, the degree of unsaturation (d) is proportional to the rigidity of the molecule of the target removing agent and may also increase the polarity of the target removing agent and solubility of the target compound removing agent in water.

The polar groups of the target compound removing agent $Q^a$, $Q^b$ and $Q^c$ confers hydrophilic property to the target compound removing agent. Thus, the more $Q^a$, $Q^b$ and $Q^c$ are present on the hydrophobic backbone, the more water solubility of the target compound removing agent.

In the target compound removing agent wherein R', R" and R'" are present in the polar group, the more carbon atoms in R', R" and R'", the less solubility of the target compound removing agent in water.

Therefore, the solubility of the target compound removing agent in water is a result of a combination of number of carbons in the backbone, degree of unsaturation, number and nature of polar groups. For example, a C12 alcohol would have a lower water solubility than a C11 alcohol, which has a lower water solubility than a C10 alcohol.

In some embodiment, in the method to selectively remove a target compound the target compound removing agent of Formula (X) is a linear or branched or C9-C34 alkyl, C9-C34 alkenyl, C9-C34 alkynyl, C9-C34 aralkyl, or C9-C34 alkaryl group substituted with $Q_i^a Q_j^b Q_k^c$ wherein i, j, and k are the numbers of $Q^a$, $Q^b$ and $Q^c$ respectively, wherein i, j, and k are each 0, 1 or 2 and at least one of i, j and k is 1 or 2.

In some embodiment, in the method to selectively remove a target compound the target compound removing agent of Formula (X) is a linear or branched or C9-C18 alkyl, C9-C18 alkenyl, C9-C18 alkynyl, C9-C18 aralkyl, or C9-C18 alkaryl group substituted with $Q_i^a Q_j^b Q_k^c$, wherein i, j, and k are the numbers of $Q^a$, $Q^b$ and $Q^c$ respectively, wherein i, j, and k are each 0, 1 or 2 and at least one of i, j and k is 1 or 2.

In some embodiment, in the method to selectively remove a target compound the target removing agent comprises a compound of formula (XI)

  (XI)

$$C_{m'}H_{(2m'+2-2d-n)}(OH)_n$$

wherein
m' is the number of carbon atoms on the main ranging from 9 to 34,
d is the degree of unsaturation ranging from 0 to 4,
n is 1, 2 or 3.

In general, the higher the number of carbons m' in the hydrophobic backbone ($C_{m'}H_{(2m'+2-2d-n)}$), the less the water solubility with the same number of hydroxyl group (n). The more polar hydroxyl group (1, 2 or 3), the higher the water solubility.

In some embodiment, in the method to selectively remove a target compound the compound of Formula (XI) is a linear or branched or C9-C34 alkyl, C9-C34 alkenyl, C9-C34 alkynyl, C9-C34 aralkyl, or C9-C34 alkaryl group substituted with (OH)n, wherein n is 1, 2 or 3. It should be understood that trialcohol (n=3), dialcohol (n=2) and monalcohol (n=1) has sequentially decreasing water solubility due to the decreasing number of polar group OH for the same hydrophobic backbone and that 1, 10-decanediol (10 carbons) has similar solubility to 1-hexanol (6 carbons).

In some embodiments, when n=2, the compound of Formula (XI) is a linear or branched or C13-C34 alkyl, C13-C34 alkenyl, C13-C34 alkynyl, C13-C34 aralkyl, or C13-C34 alkaryl group substituted with two OH.

In some embodiments, when n=3, the compound of Formula (XI) is a linear or branched or C17-C34 alkyl, C17-C34 alkenyl, C17-C34 alkynyl, C17-C34 aralkyl, or C17-C34 alkaryl group substituted with three OH.

In some embodiment, in the method to selectively remove a target compound the compound of Formula (XI) is a linear or branched or C9-C12 alkyl, C9-C12 alkenyl, C9-C12 alkynyl, C9-C12 aralkyl, or C9-C12 alkaryl group substituted with OH.

In some embodiment, in the method to selectively remove a target compound wherein the compound of Formula (XI) is a linear or branched or C9-C12 alkyl, C9-C12 alkenyl, C9-C12 alkynyl, C9-C12 aralkyl, or C9-C12 alkaryl group substituted with OH, the target compound has a water solubility equal to or greater than 0.01 g per 100 mL, 0.1 g per 100 mL, 1 g per 100 mL, or 10 g per 100 mL, at 25° C. at 1 atm pressure. In those embodiment use of C9-C12 alcohols are expected to result an increased removal of target compound with relatively higher solubility.

In particular, C9-C12 alcohols are expected to be effective inhibitors for removing ethanol (fully-miscible) and inhibitors such as 2-mercaptoethanol, phenol, chaotropic salts such guanidinium isothiocyanate, and additional reaction inhibiting target compounds buffer salts such as Tris-HCl, ionic salts such as NaCl, detergents such as Triton X-100 or Sodium dodecyl sulfate, proteinases such as proteinase K, reducing agents such as dithiothreitol and additional reaction inhibiting target compounds identifiable by a skilled person upon reading of the present disclosure, such as the target compounds comprised in Qiagen buffer RLT, Qiagen buffer RLT plus, Qiagen buffer AL, Qiagen buffer ASL, Qiagen buffer ATL, Qiagen buffer P2, Zymo DNA/RNA Lysis Buffer, Zymo RNA lysis buffer, Zymo YR lysis buffer, Zymo S/F RNA lysis buffer Qiagen buffer PE, Qiagen buffer QC, Qiagen buffer RPE, Qiagen buffer RW1 Zymo DNA wash buffer, Zymo RNA wash buffer, Zymo DNA/RNA wash buffer and additional commercial buffers identifiable by a skilled person In some embodiments, C9-C12 alcohols or higher alcohols are expected to be particularly effective in separating reaction inhibiting target compounds comprising in samples such as bile salts, complex polysaccharides, collagen, heme, humic acid, melanin and eumelanin, myoglobin, polysaccharides, proteinases, calcium ions, urea, hemoglobin, lactoferrin, immunoglobin G, indigo dye, and additional target compounds identifiable by a skilled person upon reading of the present disclosure.

Additionally, in some embodiments, as C9-C12 alcohols, higher alcohols or compounds with a comparable solubility have low solubility (e.g. <0.1 g/100 g) in water they do not inhibit PCR or LAMP. Additionally, ethanol is soluble in C9-C12 alcohols those alcohols are preferred for removing ethanol (wash buffer).

In some of the preferred embodiments the target removing agent can be or comprise a high chain alcohol. As used herein, the term "high chain alcohols" or "long chain alcohol" interchangeably refer to an aliphatic monoalcohol having at least 9 to 34 carbons, preferably 9 to 16 carbon atoms, or a dialcohol having at least 12 to 34 carbon atoms, preferably 17 to 34 carbon atoms, or a trialcohol having between 14 to 34 carbon atoms, preferably 20 to 34 carbon atoms, inclusive of any linear or branched isomers of alcohol.

In some of the preferred embodiments, the target compound removing agent can comprise a combination of high chain alcohol herein described.

In some of the preferred embodiments, the target compound removing agent can comprise a high chain alcohol.

In some of the preferred embodiments, the target removing agent can comprise a high chain with a degree of saturation d ranging from 0 to 4.

In some embodiments, in the method to selectively remove a target compound, the target compound removing agent comprises at least one of an aliphatic monoalcohol having 9 to 34 carbons, silicone oil, FC-40 or any combination thereof. Preferably, the target compound removing agent comprises at least one high chain alcohol, more preferably a 1-undecanol or 2-dodecanol.

In some embodiments, in the method to selectively remove a target compound, the target compound removing agent comprises 1-undecanol and/or 2-dodecanol.

In some embodiments, in the method to selectively remove a target compound, the target compound removing agent comprises silicone oil, and/or FC-40.

In some embodiments, the removing agent is a silicone oil.

In some embodiment, the silicone oil comprises a compound having a linear or cyclic backbone represented by Formula (II):

  Formula (II)

$$E_1-[SiR_{14}R_{15}O]_h-E_2$$

wherein
R14 and R15 are independently linear, or branched, substituted or unsubstituted, alkyl, alkenyl, alkynyl, an aryl, alkylaryl containing h number of carbons, wherein h is at least 1 and equal to or less than 20;
E1 is selected from the group comprising null for cyclic backbone, H, OH, a lower alkyl group of C1-C4; E2 is selected from the group comprising null for cyclic backbone, H, a lower alkyl, alkenyl or alkynyl group of C1-C4; and
h is at least 1, 10, 30, 50 or 100.

In some embodiment, a silicone oil of Formula (II) can be decamethylcyclopentasiloxane having of Formula of $[(CH_3)_2SiO]_5$, wherein the silicone oil of Formula (II) has a cyclic backbone, and wherein E1 and E2 are null, and R14 and R15 are methyl groups, and h is 5.

In some embodiment, the removing agent is a silicone oil represented by Formula (III):

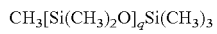 Formula (III)

wherein q is at least 1, 10, 30, 50 or 100. In some embodiments, the removing agent can be a silicone oil of Dow Corning Corporation 200® fluid from Dow Corning Corporation. As indicated above skilled person will be able to identify a suitable removing agent based on the physico chemical properties of the target compound to be removed and the related attachment to the solid matrix.

Exemplary target compounds and corresponding removing agent comprise a wash buffer containing 70% ethanol which can be removed with 5-nonanol, 2-decanol, 2-dodecanol, silicone oil, FC-40, FC-70, and a lysed sample containing chaotropic lysis agents that can be removed with 5-nonanol, 2-decanol, 2-dodecanol).

In some embodiments, a target compound comprising a wash buffer containing 100% ethanol can be removed with a removing agent selected from the group comprising 5-nonanol, 2-decanol, 2-dodecanol, silicone oil, FC-40, and FC-70 or any combination thereof.

In some embodiments, a target compound comprising a wash buffer containing 100% ethanol as can be removed with a removing agent selected from the group comprising 5-nonanol, 2-decanol, 2-dodecanol, silicone oil, FC-40, and FC-70 or any combination thereof, wherein the wash buffer containing 100% ethanol as a target compound is removed from a solid matrix selected from the group comprising Zymo-Spin™ IIC-XL Columns, Zymo-Spin I, Zymo-SpinIB, Zymo-Spin IC, Zymo-Spin IC-XL, Zymo-Spin II, Zymo-Spin IIC, Zymo-Spin IIN, Zymo-Spin V, Zymo-Spin VI, Zymo-Spin IIICG, Zymo-Spin IC-S, Zymo-Spin VI-P, Zymo-Spin V-E, Zymo-Spin III, QIAprep 2.0 Spin Miniprep Column, QIAamp Mini Spin Columns, MinElute Spin Columns, DNeasy Mini Spin Columns, RNeasy Mini Spin Columns, RNeasy MinElute Spin Columns, borosilicate Glass Fiber Grade A, borosilicate Glass Fiber Grade B, borosilicate Glass Fiber Grade C, borosilicate Glass Fiber Grade D, borosilicate Glass Fiber Grade E, borosilicate Glass Fiber Grade F, borosilicate Glass Fiber Grade 934-AH, borosilicate Glass Fiber Grade TSS, borosilicate Glass Fiber Grade VSS, and borosilicate glass capillaries.

In some embodiments, the target compound removing agent is selected to be hydrophilic enough to wet the solid matrix and solubilize target compounds such as salts, or ethanol or other contaminants, but hydrophobic enough to separate from water.

In some embodiments, the target compound removing agent is selected to physically displace a target compound originating from the sample, or from sample processing with agents (e.g. lysis buffer, wash buffer).

In some embodiments, the target compound removing agent is selected to be capable of solubilizing and removing a target compound originating from the sample.

In some embodiments, the target compound is selected to physically displace a target compound originating from the sample, or from processing the sample with agents such as silicone oil or FC-40 to displace lysis buffer or wash buffer containing ethanol.

In some embodiments, the target compound removing agent is selected to be capable of solubilizing and removing a target compound originating from the sample such as 2-decanol, 2-dodecanol, and wash buffer containing ethanol.

In some embodiments, the solid matrix has a solid matrix volume, the removing agent has a removing agent volume, the removing agent volume is 1 to 10 times or more the solid matrix volume; and the removing agent is eluted through the solid matrix at a flow rate of 1 microliter per second to 10 milliliter per second.

In some embodiments, the solid matrix has a solid matrix volume and the removing agent is eluted through the solid matrix under a pressure from 0.2 psi to 100 psi or from 1 psi to 10 psi.

In some embodiments, contacting the solid matrix with a target compound removing agent comprises eluting the removing agent through the solid matrix to remove at least 95%, 97%, 99%, 99.5%, 99.99%, or 99.999% of the target compound from the solid matrix.

In some embodiments, contacting the solid matrix with a target compound removing agent comprises eluting removing agent through the solid matrix to remove at least 80%, 90%, 95%, 97%, 99%, 99.5%, 99.99%, or 99.999% of the target compound from the solid matrix.

In some embodiments, contacting the solid matrix with a target compound removing agent is performed to obtain in a solid matrix retaining at least 10%, 20%, 30%, 50%, 75%, 90%, 95%, 98%, 99%, 99.5%, 99.8%, 99.9%, or 99.99% of the nucleic acid.

In some embodiments, the removing agent according to the disclosure can be used in alternative or in addition to additional removing agent such as an ethanol wash.

In some embodiments, removal of the target compound can be used in a method to capture a nucleic acid in a solid matrix. The term "capture" as used herein indicates the inhibition or prevention of chemical behavior of a compound by combination with added materials so that the captured compound is no longer available for reactions. In particular, in some embodiments of the disclosure, capturing of the nucleic acid is performed by sequestration of the nucleic acid by the solid matrix.

In those embodiments, the method comprises contacting the solid matrix with a solution comprising the nucleic acid together with a target compound having a water solubility equal to or greater than 0.001 g per 100 mL; and contacting the solid matrix with a target compound removing agent having a water solubility equal to or less than 10 g per 100 mL with water having a solubility in the removing agent of less than 30 g per 100 mL. In those embodiments, the contacting the solid matrix with a target compound removing agent is performed to remove the target compound from the solid matrix thus capturing the nucleic acid in the solid matrix.

In some of those embodiments, the captured nucleic acid is then removed from the solid matrix, by contacting the solid matrix with a nucleic acid removing agent. In particular, in methods herein described the contacting the solid matrix with a nucleic acid removing agent comprises eluting the nucleic acid from the solid matrix by washing the solid matrix with the nucleic acid removing agent.

In some of those embodiments, the nucleic acid removing agent can comprise nuclease-free water, preferably having a pH value within the range of pH 2 to 12, or within a range of pH 5 to 8. As used herein, a nuclease-free water is a substantially pure water (containing contains less than 100 ppm of dissolved or suspended material) that contains no detectable nuclease. In particular, pure water refers to a nuclease-free water that is not DEPC (diethyl pyrocarbonate) treated. In the Examples section, the specific Invitrogen/Ambion Nuclease-Free Water (not DEPC-Treated) by ThermoFisher Scientific, catalog No. AM9932 was used. Any elution buffer that does not have NAs, is non-inhibitory to PCR or LAMP, and elutes DNA/RNA from the column (e.g. DNA/RNAse-free water, Tris-EDTA (TE) buffer, Tris-EDTA-tween (TE+) buffer, commercial elution buffer such as Qiagen EB buffer) can be used in place of the Invitrogen/Ambion Nuclease-Free Water as will be understood by a skilled person upon reading of the present disclosure In some of those embodiments, a nucleic acid removing agent can comprise a Tris-EDTA Buffer, distilled water, a DNA Elution Buffer (e.g. Zymo Research, D3004-4-10), and DNase/RNase-Free Water (e.g. Zymo Research, W1001-1), or any combination thereof. In some of those embodiments, the nucleic acid removing agent or elution buffers can be heated to a temperature between 20° C. and 99° C.

In some embodiments, the nucleic acid removing agent is buffered to have a pH within the range of pH of 2 to 12, preferably have a pH value ranging from 3 to 10, from 4 to 9, from 5 to 8 or from 6 to 8. In some embodiments, the buffered nucleic acid removing agent contains Tris. In some embodiments, the buffered nucleic acid removing agent contains EDTA. In some preferred embodiments, the buffered nucleic acid removing agent is a nuclease-free water buffered with Tris-EDTA. Accordingly, in some preferred embodiments, the nucleic acid removing agents comprise at least one of nuclease-free water, or Tris EDTA buffer.

In some embodiment, in the method to selectively remove a target compound, the nucleic acid comprises more than 100 bases, more than 300 bases, more than 500 bases, more than 700 bases, or more than 1000 bases.

In some embodiment, in the method to selectively remove a target compound the nucleic acid is modified and/or comprises a secondary structure such as a stem-loops or pseudoknots structure.

In some embodiment, in the method to selectively remove a target compound the nucleic acid has a GC content of at least 50%, at least 55%, at least 60%, at least 65%, at least 70%, at least 75%, or at least 80%.

In some embodiments, the eluted nucleic acids are single-stranded DNA, double-stranded DNA, single-stranded RNA, double-stranded RNA, plasmid DNA, short fragments less than 50 base pairs, short fragments between 50 and 150 base pairs, medium fragments between 150 base pairs to 3 kilobase pairs, long fragments greater than 3 kilobase pairs, genomic DNA, chromosomal DNA, mitochondrial RNA, ribosomal RNA, messenger RNA, transfer RNA, small nuclear RNA, synthesized DNA, or synthesized RNA In some embodiments, wherein the method is directed to elute nucleic acids other than DNA the method further comprises contacting the solid matrix with a DNAase prior to performing contacting the solid matrix with a nucleic acid removing agent. In some embodiments, wherein the method is directed to elute nucleic acids other than RNA the method further comprises contacting the solid matrix with a RNAase prior to performing contacting the solid matrix with a nucleic acid removing agent.

In some of those embodiments, the captured nucleic acid eluted from the solid matrix is used to perform a biochemical reaction of interest (target biochemical reaction) In those embodiments, the eluted nucleic agent is contacted with suitable reagents to perform the target biochemical reaction of the nucleic acid.

Exemplary target biochemical reaction of the nucleic acid comprise nucleic acid amplifications such as polymerase chain reaction (PCR) or loop-mediated isothermal amplification (LAMP), strand displacement amplification, helicase-dependent amplification, nicking enzyme amplification reaction, sequencing, next-generation sequencing, nanopore sequencing, reverse transcription, quality analysis, ligation of sequencing barcodes, cloning, gel electrophoresis, cell-free extract transcription translation, plasmid generation, and CRISPR-Cas9, in-vitro transcription.

Exemplary target biochemical reaction of the nucleic acid comprise the target biochemical reaction is comprised in PCR, LAMP, strand displacement amplification, helicase-dependent amplification, nicking enzyme amplification reaction, Sequencing, next-generation sequencing, reverse transcription, quality analysis, ligation of sequencing barcodes, cloning, gel electrophoresis, cell-free extract transcription translation, plasmid generation, CRISPR-Cas9, or in-vitro transcription.

Exemplary target biochemical reaction is comprised in single-cell sequencing, or pathogen diagnostics.

In some embodiments, the target biochemical reaction is LAMP. In those embodiments, the target compound removing agent is preferably 2-decanol, 2-dodecanol (see Example 3, Example 7 and Example 8), In some embodiments, the target biochemical reaction is PCR. In those embodiments, the target compound removing agent is preferably 2-decanol, 2-dodecanol, 5 cst Silicone and Fc40 (see Example 6 and Example 8).

In some embodiments, the target biochemical reaction is a nucleic acid amplification test The term "nucleic acid amplification test" (NAAT) refers to a procedure to identify a DNA or RNA in a sample including a series of repeated chemical or biochemical reactions to make numerous copies of the DNA or RNA. The term RT-NAAT as used herein refers to "reverse-transcriptase NAAT."

In some embodiments, the target biochemical reaction is an RT-LAMP The term "RT-LAMP" refers to reverse transcription loop-mediated isothermal amplification (RT-LAMP).

In some embodiments, the target biochemical reaction is an RT-qPCR. The term "Quantitative reverse transcription PCR" (RT-qPCR) refers to a procedure in which a starting material is RNA, the RNA is first transcribed into complementary DNA (cDNA) by reverse transcriptase from total RNA or messenger RNA (mRNA), the cDNA is then used as the template for the qPCR reaction. For example, in a one-pot RT-qPCR, cDNA synthesis and qPCR are performed in a single reaction vessel in a common reaction buffer. In a two-step RT-qPCR, cDNA is synthesized in one reaction, and an aliquot of the cDNA is then used for a subsequent qPCR experiment.

In some embodiment, the target biochemical reaction of the nucleic acid is DNA or RNA sequencing.

In some embodiment, the target biochemical reaction of the nucleic acid comprises ligation of sequencing barcodes.

In some embodiments, the target biochemical reaction of the nucleic acid is the ligation of sequencing barcodes to provide a mixture of another target compound and another nucleic acid. In those embodiments the mixture of another target compound and another nucleic acid can optionally be contacted by a second removing agent to capture another nucleic acid, wherein the another nucleic acid can be optionally used in another target biochemical reaction such as DNA or RNA sequencing.

In some embodiments, the target biochemical reaction is sanger sequencing, pyrosequencing, large-scale sequencing, next-generation sequencing, whole-genome sequencing, or nanopore sequencing.

In some embodiments, the target downstream reaction is sanger sequencing, pyrosequencing, large-scale sequencing, next-generation sequencing, whole-genome sequencing, or nanopore sequencing.

In preferred embodiments, the methods and systems and compositions of the disclosure can be used to separate mixtures comprising nucleic acid in a low amount relative to the LOD of the biochemical reaction to be performed on the nucleic acid following separation from the target compound.

As used herein, the wording "limit-of-detection" or "LOD" used with respect to a method of analysis of a nucleic acid indicates the minimum nucleic acid amount allowing an accurate detection of the nucleic acid with 95% confidence (19 out of 20 samples) according to the referenced method of analysis. The limit-of-detection will depend on the specific target, primers, reaction conditions (e.g. buffers, polymerases, reverse transcriptase, thermocycling conditions) as will be understood by a skilled person.

Exemplary analysis includes qPCR, LAMP, and dPCR, the corresponding LOD are qPCR: 1 copy/reaction to 1E7 ($1 \times 10^7$) copies/reaction, LAMP: 1 copy/reaction to 1E7 copies/reaction and dPCR: 1 copy/reaction to 1E7 copies/reaction, depending on the specifics of the reaction as will be understood by a skilled person. Additional analysis methods and related LOD are identifiable to a skilled person.

In some embodiments, a low concentration of nucleic acid can be equal to or less than 1×, 10×, 100×, 1000×, 10000×, 100000× a limit-of-detection LOD of a biochemical reaction In some embodiments, the solution comprising the nucleic acid at a concentration of 1 M or less can comprise a nucleic acid at a concentration equal to or less than ×100,000, equal to or less than ×10,000, equal to or less than ×1,000, equal to or less than ×100, equal to or less than ×10, or equal to or less than 2×, or at 1× of a limit-of-detection (LOD) of biochemical analysis an analysis. In some of those embodiments the biochemical analysis is of qPCR, LAMP, or dPCR.

In most preferred embodiments of the present disclosure, methods and system of the disclosure and related compositions, can be advantageously used to separate from a mixture, a nucleic acid to be subjected to analysis, which is comprised in the mixture at a concentration close to the LOD of the analyses.

In some embodiments of the method to selectively remove a target compound by contacting the solid matrix with a pH neutral target compound removing agent, the solution comprises a nucleic acid at a concentration equal to or less than ×100,000, equal to or less than ×10,000, equal to or less than ×1,000, equal to or less than ×100, equal to or less than ×10, or equal to or less than 2×, or at 1× of a limit-of-detection (LOD) of an analysis.

In some embodiments of the method to selectively remove a target compound by contacting the solid matrix with a pH neutral target compound removing agent, the limit-of-detection (LOD) of an analysis is the limit-of-detection (LOD) of qPCR, LAMP, or dPCR.

In those embodiments, contamination of target compounds or target compound removing agent into the elution can be disruptive to downstream analyses as the target compound or target removing agent act as inhibitor of the reaction.

Therefore, in those embodiments, the target compound removing agent is selected so that the selected removing agent inhibits a target enzyme catalyzing a target biochemical reaction of the nucleic acid by a rate of less than 50% when the target compound removing agent is comprised in the target compound removing agent at a concentration equal to or higher than 10% of a saturated concentration of the target compound removing agent in the nucleic acid removing agent.

In some of those embodiments, the inhibition of the rate of the target enzyme by the selected target compound removing agent is measured when the target compound removing agent is comprised in the nucleic acid removing agent at a concentration equal to or higher than 50% of the saturated concentration of the target compound removing agent in the nucleic acid removing agent.

In some of those embodiments, the inhibition of the rate of the target enzyme by the selected target compound removing agent is measured at the saturated concentration of the target compound removing agent in the nucleic acid removing agent.

In some of those embodiments, the target compound removing agent is selected to inhibit the target enzyme by a rate of less than 25%, more preferably less than 10% even most preferably less than 5%.

In some embodiments, the half or more of a saturated concentration of the target compound removing agent in the nucleic acid removing agent is 1 g per 100 mL.

In particular, in some embodiments a target removing agent with low solubility in water does not significantly inhibit PCR or LAMP efficiency and the PCR delay is less than 10 cycles, 9 cycles, 8 cycles down to 1 cycle, or the LAMP delay is less than 1 min, 2 min, 3 min, 4 min, 5 min, 10 min or 20 min and is thus less inhibitory than ethanol.

Exemplary target compound removing agents capable of inhibiting a target enzyme catalyzing a target biochemical reaction of the nucleic acid by a rate of less than 50% at 1 g per 100 mL, comprise long-chain alcohols such as nonanol, decanol, dodecanol, or molecules such as long carboxylic acids, or mixes of the molecules mentioned above with tetradecane, silicone oil or fluorocarbon oils. Exemplary fluorocarbon oil includes Fluorinert™ FC-40 manufactured by 3M Company having Corporate headquarters at 3M Center, St. Paul, Minn. 55144-1000. Exemplary silicone oils are the compounds of Formula (II) or Formula (III) of the instant disclosure.

In those embodiments, the elution comprising the nucleic acid can be used directly for the downstream target biochemical reaction, possibly in absence of dilutions which can be performed to dilute carryover contamination. In those embodiments, sequestered nucleic acids can provide a small fraction (<25%) or a larger fraction of the final nucleic acid amplification mixture. In preferred embodiments, the nucleic acid makes up a large fraction (50%-100% such as for lyophilized reagents) of the final nucleic acid amplification mix.

In those embodiments, the method of sequestration and washing a nuclei acid on a solid-phase column can comprises eluting the nucleic acid from the solid matrix with an approach including or not including centrifugation.

In an exemplary embodiment of an approach including centrifugation, the sample containing nucleic acids is mixed with a buffer such as a lysis buffer containing chaotropic salts. The lysed sample is centrifuged through a solid-phase column, such as a silica column, and the nucleic acids bind to the silica. A wash buffer, containing one or more target compound removing agents herein described, is centrifuged through the column to remove the chaotropic salts while maintaining the bond between the nucleic acids and silica. In some cases, two or three wash steps can be performed. In some cases, an additional dry centrifugation step can be performed. Water is then centrifuged through the column (elution step), which disrupts the bond between nucleic acids and silica, resuspending the nucleic acid into the aqueous solution.

In embodiments where contacting a solid matrix with a target compound removing agent in accordance with the disclosure comprises eluting the removing agent with centrifugation or aspiration, preferred removing agents comprise 2-decanol, 2-dodecanol 5 cst Silicon, and Fc40.

In embodiments wherein contacting a solid matrix with a target compound removing agent in accordance with the disclosure comprises eluting the target compound removing agent with centrifugation or aspiration, preferred target compound removing agents comprise a monoalcohol of a higher alkyl group, a higher alkenyl group, or a higher alkynyl group.

A higher alkyl group as used herein contains at least 9 carbon atoms, preferably 9 to 18 carbon atoms (C9-C18), such as n-octyl, n-nonyl, n-decyl, dodecyl, ricinoleyl, and the like, as well as cycloalkyl groups such as cyclooctyl group.

A higher alkenyl group as used herein contains at least 9 carbon atoms, preferably 9 to 18 carbon atoms (C9-C18), and at least one C—C double bond.

A higher alkynyl group as used herein contains at least 9 carbon atoms, preferably 9 to 18 carbon atoms (C9-C18), and at least one C—C triple bond.

In other embodiments, methods and systems herein described can be used in non-centrifuge approaches to aspirate solutions such as removing agents.

In an exemplary embodiment, a non-centrifuge approach comprises a pressure-based or vacuum-based pump fluidically connected to a column comprising a solid matrix.

In embodiments where contacting a removing agent is performed using pressure-based (positive-pressure or vacuum) pumping, air pushes liquid out of a few pores but the remaining pores can stay filled with liquid.

In an exemplary embodiment, a non-centrifuge approach comprises aspiration of a liquid as illustrated in FIG. 1 and Example 18.

In embodiments where contacting a solid matrix with a target compound removing agent in accordance with the disclosure comprises eluting the removing agent without centrifugation (using pressure-based elution and in particular positive-pressure or vacuum elution), preferred removing agents comprise 2-decanol and 2-dodecanol.

In particular these embodiments the use of removing agents such as 1-nonanol and/or longer chain alcohols is especially beneficial as in centrifugation systems, contaminants can be removed more effectively when compared to pressurized systems, which are less effective in removing residual target compound. FIG. 1 depicts the carryover of buffers during sample preparation and demonstrates how the use of a TPW as an additional wash buffer improves a qPCR run compared to no TPW(1c).

In both centrifugation and pressure-based pumping embodiments, a wash with a target compound removing agent herein described can be performed alone or following contacting of the matrix with an ethanol wash or other wash. The purified nucleic acids with loop-mediated isothermal amplification (LAMP) can then be performed (see Example 3).

In embodiments where the contacting of the solid matrix with the target compound removing agent is performed by eluting the solid matrix with a wash additional to an ethanol wash or other wash, preferred target compound removing agents comprise 2-decanol, 2-dodecanol.

In embodiments where the contacting of the solid matrix with the target compound removing agent is performed by eluting the solid matrix with a wash replacing an ethanol wash or other wash, preferred target compound removing agents comprise 2-decanol, 2-dodecanol.

In some embodiments, the solid-phase column is used for the selective capture of analytes, such as nucleic acids, in a process for purifying these molecules from a sample. Those embodiments, can typically comprise applications and experiments in fundamental and applied nucleic acid (NA) research which depends on NA purity, in particular when the NAs is obtained from raw, unprocessed samples.

In those embodiments, target removing agents herein described and related method and systems can be used in applications requiring high sensitivity to complement existing purification systems and protocols which perform nucleic acids purification by solid-phase NA extractions using sequential additions of lysis and wash buffers followed by elution. In these existing methods and system the resulting eluent contains NAs and carryover of extraction buffers. Typically, these inhibitory buffers are heavily diluted by the reaction mix (e.g., 10×dilution is 1 μL eluent in 9 μL reaction mix), but in applications requiring high sensitivity (e.g., single-cell sequencing, pathogen diagnostics) it is desirable to use low dilutions (e.g., 2×) to maximize NA concentration.

Accordingly, methods and systems herein described can be used to perform purification of nucleic acid in connection with high sensitivity applications where pervasive carryover of inhibitory buffers into eluent occurs when several commercial sample-preparation kits are used following manufacturer protocols (e.g. at low eluent dilution (2-2.5×) it was observed significant reaction inhibition of polymerase chain reaction (PCR), loop-mediated isothermal amplification (LAMP), and reverse transcription (RT)).

In those embodiments, the eluting is performed at a low eluent dilution of less than 3×. In those embodiments, the eluting is performed at a low eluent dilution from 2× to 2.5×.

In those embodiments, a two-phase wash (TPW) method can be used in accordance with the present disclosure to in high sensitivity requiring applications by adding a wash buffer with low water solubility prior to the elution step. The TPW reduces carryover of extraction buffers, phase-separates from the eluent, and does not reduce NA yield (measured by digital PCR). The TPW for silica columns and magnetic beads was validated by demonstrating significant improvements in performance and reproducibility of qPCR, LAMP, and RT reactions.

In these purification protocols, the sample can be first mixed with chaotropic agents such as guanidinium thiocyanate, and this mixture is then pumped or centrifuged through the solid-phase column in order to capture nucleic acids on the column. Following this capture step, wash buffers comprising removing agent herein described can be used for removal of sample contaminants such as salts and proteins. Example samples typically comprise urine, blood, serum, plasma, and saliva.

In some embodiments of methods and systems herein described a target compound removing agent can be provided in the form selected from (a) partially miscible wash, (b) amphiphilic wash, and (c) partially miscible amphiphilic wash.

Partially miscible wash displaces previous washes and has low solubility in water of equal to or less than 10 g per 100 mL, equal to or less than 1 g per 100 mL, but equal to or higher than 0.01 microgram (g) per 100 mL.

In some embodiments, partially miscible wash includes silicone oil, fluorinated oil as removing agent. In some embodiments, partially miscible wash is used in embodiments where the target compound removing agent is used an additional wash to remove ethanol.

An amphiphilic wash as used herein are polar enough to solubilize contaminants, salts, or wash buffer. Exemplary contaminants include lysis buffers containing chaotropic salts, wash buffers containing 60-80% ethanol, 100% ethanol. In some embodiments, amphiphilic wash comprises a removing agent in the form of ketones, alcohols, or carboxylic acids of C5-C7.

In some embodiments, amphiphilic wash is used as a first wash in the NAs purification on a silica column to remove contaminants, salts.

A partially miscible amphiphilic wash indicates a wash comprising a removing agent that is polar enough to solubilize a target compound such as a contaminant but has low solubility in water of equal to or less than 0.05 g per 100 mL at 25° C. at 1 atm pressure with water having a solubility in the removing agent of less than 10 g per 100 mL at 25° C. at 1 atm pressure. The amphiphilic wash such 2-decanol can interact better with the water-soluble contaminants than FC-40.

In some embodiments, a partially miscible amphiphilic wash is used as a first wash in the NAs purification on a silica column to remove contaminants, salts.

Exemplary partially miscible amphiphilic wash includes higher alcohols such as 5-nonanol, decanol, dodecanol, ricinoleyl alcohol or any combination thereof. Exemplary partially miscible amphiphilic wash also includes castor oil, linoleic acid, oleic acid, ricinoleic acid, stearic acid, palmitic acid, plant oils, vegetable oils, mineral oils or any combination thereof. Exemplary partially miscible amphiphilic washes further include one or more higher carboxylic acids. In some embodiments, a partially miscible amphiphilic wash can include any combination of nonanol, 5-nonanol, decanol, dodecanol, ricinoleyl alcohol, castor oil, linoleic acid, oleic acid, ricinoleic acid, stearic acid, palmitic acid, plant oils, vegetable oils, mineral oils or one or more higher carboxylic acids.

In some embodiments, a target compound removing agent can be selected from the group consisting of palm oil, coconut oil, canola oil, soybean oil, sunflower oil, rapeseed oil, peanut oil, cotton seed oil, palm kernel oil and olive oil.

In some embodiments, one or more removing agent can be used for additional or replacement wash step in a solid-phase extraction (SPE) process wherein the solid matrix can include silica in the form of gel particles, glass particles, glass microfibers or slurry resins, wherein the glass particles in turn may be in the form of powder, microbeads, silicate glass, flint glass, borosilicate glass, or glass fiber filters.

In some embodiments, one or more target compound removing agents can be used for an additional or replacement wash step in a solid-phase extraction (SPE) process wherein the solid-phase can include diatomaceous earth, magnetic beads with complementary hybrids, anion exchange resins, or cellulose matrices.

In some embodiments, a target compound removing agent can be used for an additional or replacement wash step in a solid-phase extraction (SPE), wherein the solid-phase extraction (SPE) comprises normal phase SPE, reversed phase SPE, ion exchange SPE, or anion exchange SPE for targeted elution of a specific analyte or purification of a sample.

In some embodiments, a target compound removing agent can be used for an additional or replacement wash step in a solid-phase extraction (SPE) of a sample, wherein the sample includes urine, blood, serum, plasma, saliva, sputum, stool, cerebrospinal fluid (CSF), or resuspended swabs (nasal, throat, eye, ear, rectal, wounds, or vaginal, urethral).

In some embodiments, a target compound removing agent can be used for an additional or replacement wash step in a solid-phase extraction (SPE) of a sample, wherein the sample includes a cell culture.

In some embodiments, a target compound removing agent can be used for an additional or replacement wash step in a solid-phase extraction (SPE) of a sample, wherein the sample comprises an environmental sample including water, air, soil, or swab.

In some embodiments, a target compound removing agent can be used for an additional or replacement wash step in a solid-phase extraction (SPE) of a sample in food quality control, wherein the sample comprises grains, meat, seafood, plants, or fruits.

In some embodiments, a target compound removing agent can be used for an additional or replacement wash step in a solid-phase extraction (SPE) of a sample in water quality control, wherein the sample comprises water supply, tap water, agriculture water, beverages, milk, or juice.

In some embodiments, a target compound removing agent can be used for an additional or replacement wash step in a solid-phase extraction (SPE) of a sample of pharmaceutical.

In some embodiments, a target compound removing agent can be used for an additional or a replacement wash step in a solid-phase extraction (SPE) of a sample in biohazardous warfare testing.

In preferred embodiments the target compound to be removed comprises one or more non-nucleic acid compounds of mixtures such as processed or unprocessed: i) biological samples (e.g. urine, blood, serum, plasma, saliva), ii) environmental samples, ii) food samples, iv) cell cultures, v) water mixtures and vi) pharmaceutical mixtures. In particular in some of these preferred embodiments the mixture are processed with a buffer agent, such as a lysis buffer possibly containing chaotropic salts, and/or a wash buffer in particular when containing compounds such as ethanol (e.g. wash buffer containing over 60% ethanol), as well as additional buffer agents identifiably by a skilled person upon reading of the present disclosure.

In those preferred embodiments, preferred removing agents comprise agent having a water solubility equal to or less than 0.05 g per 100 mL at 25° C. at 1 atm pressure with water having a solubility in the removing agent of less than 10 g per 100 mL at 25° C. at 1 atm pressure. In those embodiments, more preferred target compound removing agents comprise a removing agent of the compound of a linear or branched or C9-C12 alkyl, C9-C12 alkenyl, C9-C12 alkynyl, C9-C12 aralkyl, or C9-C12 alkaryl group substituted with OH or mixture thereof as will be understood by a skilled person upon reading of the present disclosure.

Typically, in those preferred embodiments the separation method is directed to separate the nucleic acid for preparation and/or analytical purposes.

In embodiments herein described, any one of the methods of the present disclosure can be performed with a corresponding system comprising a target compound removing agent having a water solubility equal to or less than 0.05 g per 100 mL at 25° C. at 1 atm pressure with water having a solubility in the removing agent of less than 10 g per 100 mL at 25° C. at 1 atm pressure; and at least one of a solid matrix configured to absorb a nucleic acid and a reagent to perform the biochemical reaction. In the system herein described the target compound removing agents, solid matrix and reagents are included in the system for simultaneous combined or sequential use in any one of the methods of the present disclosure. In some embodiments, the system can further comprise a nucleic acid removing agent as will be understood by skilled person.

In some embodiments, addition of the TPW to existing protocols is known or expected to improve NA extraction purity and performance of downstream assays in a variety of applications. In particular, in some embodiments, performance of TPW is know or expected to improve NA purity for a range of commercial extractions kits and a range of nucleic-acid targets.

Accordingly, the indications concerning protocols and methods, systems as described herein ca are not exhaustive and a person of skill in the art would understand every possible kit, every possible sample type, every possible NA reaction, and every possible nucleic-acid target of variances based on the present disclosure. In those embodiments, a TPW method according to the present disclosure provides is inexpensive and easy to incorporate into both silica-column (one additional spin) and magnetic-bead extractions (one additional aspiration), and therefore a person skill in the art, including researchers and commercial suppliers can test TPW in other suitable workflows and protocols based on the present disclosure. In particular, in some embodiments the TPW extraction is expected to be used in combination with lyophilized reagents, which requires no dilution, and is highly desirable for point-of-care diagnostics.

In some embodiments, the TPW is expected to enable the field to develop new methods of sample preparation, such as pressure- or vacuum-based NA extractions, that are simpler, quicker, and more portable than current protocols.

In some embodiments, in addition to reducing extraction buffer carryover, it is contemplated that the TPW according to the present disclosure could also reduce carryover of some compounds originating from the sample by removing them from the solid phase. For example, long-chain alcohols are expected to remove nonpolar compounds better than traditional wash buffers (ethanol or isopropanol). This hypothesis remains to be tested in future work. Furthermore, it is expected that improved eluent purity from the added TPW according to the present disclosure will enable high-sensitivity analyses that were previously difficult or impossible because high dilution of eluent has been the de facto standard. Improved eluent purity would be especially valuable for more challenging reactions, including long amplicons (DNA and RNA), targets with high GC content, and highly structured or chemically modified RNA targets (e.g. rRNA, tRNA). By enabling the use of lower dilutions, methods and systems of the disclosure would enhance performance of NA analysis in applications where sensitivity and reproducibility are critical, including single-cell sequencing, cell-free circulating DNA analyses and SNP detection, and molecular diagnostics.

The systems herein disclosed can be provided in the form of kits of parts. In kit of parts for performing any one of the methods herein described, the target compound removing agent, solid matrix, reagents to perform the target biochemical reaction and nucleic acid removing agent can be included in the kit alone or in the presence of one or more the reagents for the related detection and/or amplification such as probes for detection and/or amplification of an RNAs and/or corresponding cDNAs.

In particular, in some embodiment, a system comprises at least two of a target removing agent having a water solubility equal to or less than 10 g per 100 mL with water having a solubility in the removing agent of less than 30 g per 100 mL; the solid matrix configured to retain a nucleic acid. In some embodiment, the system can further comprise a nucleic acid removing agent.

In some embodiment, a system of the disclosure can contain a nucleic acid removing agent selected from nuclease-free water, distilled water, Tris EDTA buffer, Tris Buffer, DNA Elution Buffer (Zymo Research, D3004-4-10), DNase/RNase-Free Water (Zymo Research, W1001-1), Buffer EB (Qiagen, Cat No./ID: 19086).

The system comprises a target compound removing agent having a water solubility equal to or less than 0.05 g per 100 mL at 25° C. at 1 atm pressure, preferably equal to or less than 0.03 g per 100 mL at 25° C. at 1 atm pressure with water having a solubility in the removing agent of less than 10 g per 100 mL at 25° C. at 1 atm pressure; and a solid matrix configured to absorb a nucleic acid.

The system can comprise any of the target removing agents that can be used in the method of the present disclosure according to the first aspect. Preferably the system comprises a target removing agent further having a solubility in ethanol at 25° C. at 1 atm pressure of at least 1 wt %, at least 5 wt %, at least 10 wt %, at least 20 wt %, at least 50 wt %, or at least 90 wt %. In those embodiments the target removing agent can have a solubility of equal to or less than 0.05 wt % in water at 25° C. at 1 atm pressure and a solubility in ethanol at 25° C. at 1 atm pressure of at least 1 wt %, at least 5 wt %, at least 10 wt %, at least 20 wt %, at least 50 wt %, or at least 90 wt %.

Preferably the target removing agents can comprise a compound of Formula X, a compound of Formula XI, a long chain alcohol or a combination thereof. In an exemplary embodiment, the target removing agent can comprise at least one high chain alcohol, more preferably a 1-undecanol or 2-dodecanol or a combination thereof.

In the system the target removing agent and the solid matrix can be formulated and comprised for simultaneous, combined or sequential use in any one of the methods according to the present disclosure with the modifications and adjustments which will be understood by a skilled person upon reading of the present disclosure.

In some embodiments, in the system the target removing agent, the solid matrix further comprise a reagent to perform a target biochemical reaction.

In some embodiments, in the system, the target biochemical reaction is selected from the group comprising PCR, LAMP, strand displacement amplification, helicase-dependent amplification, nicking enzyme amplification reaction, Sequencing, next-generation sequencing, reverse transcription, quality analysis, ligation of sequencing barcodes, cloning, gel electrophoresis, cell-free extract transcription translation, plasmid generation, CRISPR-Cas9, and in-vitro transcription.

In embodiments, in the system, the target biochemical reaction is a two-step RT-qPCR, RT-LAMP, or other RT-NAAT combination.

In a kit of parts, the target compound removing agent, for example in a blister pack, solid matrix the reagents to perform biochemical reaction of interest such as LAMP or PCR the reagents for the related detection and additional reagents identifiable by a skilled person are comprised in the kit independently possibly included in a composition together with suitable vehicle carrier or auxiliary agents. For example, one or more removing agents can be included in one or more compositions together with reagents for detection of nucleic acid also in one or more suitable compositions.

Additional components can include labeled polynucleotides, labeled antibodies, labels, microfluidic chip, reference standards, and additional components identifiable by a skilled person upon reading of the present disclosure.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (i.e. wash buffers and the like).

Low toxicity, reactivity, health hazard to humans of removing agent allows broad use of removing agents herein descried in nucleic acid detection and/or amplification kits of the present disclosure.

Further details concerning the identification of the suitable carrier agent or auxiliary agent of the compositions, and generally manufacturing and packaging of the kit, can be identified by the person skilled in the art upon reading of the present disclosure.

In some embodiments, the method and systems of the disclosure can be used with a device such as the device described in U.S. application Ser. No. 16/130,810 filed on Sep. 13, 2018 and entitled "Purification and Detection of Analytes", incorporated herein by reference in its entirety. In those embodiments, a target compound removing agent can be stored in the system in foil or blister packs, which break at high pressures, or are pierceable by piercers on a pumping lid. For example, the pumping lid can have a sharp point which, when the lid is pushed down, will pierce the blister pack and release the target compound removing agent. The target compound removing agent within the blister is therefore free to exit the blister and enter the device's chamber. For example, the blister can be located within the chamber. In other embodiments, instead of a blister which envelops the target compound removing agent entirely, the target compound removing agent can be contained within the chamber, with a foil on the top of the chamber. In this case, the foil is pierced in a similar manner of the blister embodiment. The foil can also be on the bottom of the chamber, or both the top and bottom. The blister pack is essentially a foil which completely surrounds the target compound removing agent.

In some embodiments, the target compound removing agent can be collected in a storage or waste chamber after contacting the solid matrix.

In some embodiments, an amplification module containing at least one reaction well is provided. The eluted nucleic acids, for example, or other target analytes, can be inserted in parallel in each reaction well, enabling the parallel analysis of the same sample, with different reagents.

Embodiments of the methods and systems described herein can be performed with additional portable devices to accomplish the process of sequestration and washing of nucleic acid on solid matrix in a solid-phase column, and optionally additional target biochemical reaction with the nucleic acid so separated. In some embodiments, the portable device is a hand-held device.

Further details concerning the identification of the embodiments of methods and systems of the disclosure and related compositions, that can be performed in combination with such devices can be identified by the person skilled in the art upon reading of the present disclosure.

EXAMPLES

The methods and system herein disclosed are further illustrated in the following examples, which are provided by way of illustration and are not intended to be limiting.

The following material and methods were used in performing the experiments reported in the following examples.
NA Stocks and Primers Lambda (λ) phage DNA (linear double-stranded 500 pg/mL, N3011 L, New England Biolabs (NEB)) was purchased from NEB and the stock was quantified at $1.1 \times 10^{10}$ cp/µL using digital PCR (dPCR). *Escherichia coli* DNA was extracted from an NEB 5-alpha strain using Epicentre QuickExtract DNA Extraction Buffer (Lucigen Corporation, Middleton, Wis., USA) and the stock was quantified at $1.4 \times 10^7$ cp/µL using dPCR. *Neisseria gonorrhoeae* live infectious stock (Z017, Zeptometrix, Buffalo, N.Y., USA) was resuspended to $5 \times 10^7$ cfu/mL in pre-warmed (37° C.) Hardy Diagnostics FB Broth (K31, Hardy Diagnostics, Santa Maria, Calif., USA) and diluted an additional 10-fold in urine to $5 \times 10^6$ cfu/mL. Urine from healthy human donors (>18 years of age) was acquired and used in accordance with approved Caltech Institutional Review Board (IRB) protocol 15-0566. Informed consent was obtained from all participants. Urine sample donations were never tied to personal identifiers and all research was performed in accordance with the approved IRB protocol and relevant institutional biosafety regulations. Urine samples were stored at room temperature and used within 1 h of collection. Spiked urine (125 µL) was mixed with DNA/RNA Shield (125 µL) and lysis buffer (500 µL) for a total lysed sample volume of 750 µL. Both DNA and RNA were extracted simultaneously with a ZR Viral DNA/RNA Kit, and *N. gonorrhoeae* 16 S RNA was found to be in over 200-fold excess of 16S DNA as verified by dPCR with or without an RT step. All NA stocks were diluted at least 100-fold into all reactions, thereby eliminating the effects of any inhibitors that could be present in the NA stock. Lambda LAMP primers [42], Lambda PCR primers [43], *E. coli* 23S rRNA gene LAMP primers [44], *E. coli* 23S rRNA gene PCR primers[45], and *N. gonorrhoeae* 16S rRNA gene PCR primers[46] have been previously published and were supplied by Integrated DNA Technologies using standard desalting purification.
LAMP Mix:

LAMP reactions contained the following concentrations of reagents: 1× Isothermal Amplification Buffer (20 mM Tris-HCl pH 8.8, 10 mM $(NH_4)_2SO_4$, 50 mM KCl, 5 mM $MgSO_4$, 0.1% Tween-20, B0537S, NEB, Ipswich, Mass., USA), an additional 2 mM $MgSO_4$ (B1003S, NEB), 1.4 mM deoxynucleotide mix (N0447L or N0446S, NEB), 2 pM Invitrogen Syto-9 (S34854, Thermo Fisher Scientific), 2 pM Invitrogen bovine serum albumin (15561020, Thermo Fisher Scientific), 320 U/mL WarmStart Bst 2.0 (M0538L, NEB), and were supplemented with nuclease-free water (not DEPC-Treated, 4387936, Thermo Fisher Scientific) up to 10 µL. LAMP primers (Integrated DNA Technologies (IDT), Coralville, Iowa, USA) were designed, ordered, and added at NEB's recommended concentrations of 1.6 pM FIP/BIP, 0.2µM F3/B3, and 0.4 pM LoopF/B.

Each 96-well plate was sealed and briefly spun. Heating and real-time imaging were performed on the Bio-Rad CFX-96 Touch Real-Time PCR Detection System (1855195, Bio-Rad). Each 96-well plate was cooled to 12° C. for 2 min, held at 68° C. for 47 min with 35-second fluorescence read intervals, and a melt-curve analysis was performed. For the *E. coli* DNA dilution experiment, the 68° C. step was held for 105 min. Time-to-positive (TTP) was determined when the software's automated baseline corrected fluorescence reached 1000 RFU.

dPCR Mix

Droplet digital PCR (dPCR) experiments were performed on a Bio-Rad QX200 Droplet Digital PCR System (1864001, Bio-Rad). dPCR mixes were made with 1× QX200 dPCR EvaGreen Supermix (1864034, Bio-Rad), 200 nM forward primer, and 200 nM reverse primer. Eluent was diluted 10× in separate tubes and an additional 10× into the reaction mix. All samples were made to 50 µL and duplicates were run by adding 22 µL to two sample wells in the DG8 Cartridge for droplet generator (1864008, Bio-Rad). Droplet generation, droplet transfer, and foil sealing followed manufacturer's instructions. Thermocycling took place on a C1000 Touch Thermal Cycler (Bio-Rad) with a pre-melt at 95° C. for 3 min, 40 cycles of 95° C. for 30 s, 60° C. for 30 s, and 68° C. for 30 s, and a stabilization at 4° C. for 5 min, 90° C. for 5 min, and a hold at 12° C. until droplet analysis. A temperature ramp rate of 2C/s was used for temperature transitions. Droplets were read according to manufacturer instructions. Analysis thresholds were manually set at the valley between negative and positive droplets. Final concentrations were determined using the merge setting on the QuantaSoft analysis software. No template controls (NTC) were always run and showed negligible normalized counts (<0.1%).

gPCR Mix qPCR reactions contained 1× Bio-Rad SsoFast Supermix (1725201, Bio-Rad), PCR primers (IDT) at 0.5 pM each, and were supplemented with nuclease-free water up to 10 µL. Each 96-well plate (thin-wall clear well, HSP9641, Bio-Rad) was sealed (Microseal B, MSB1001, Bio-Rad) and briefly spun in a Mini Plate Spinner Centrifuge (14-100-141, Fisher Scientific). Heating and real-time imaging were performed on the Bio-Rad CFX-96 Touch Real-Time PCR Detection System by heating to 95° C. for 5 min, cycling 40 times between 95° C. for 15 s, 60° C. for 15 s, and 72° C. for 20 s, and taking a melt-curve analysis. For the *E. coli* DNA dilution experiment, qPCR was run for 60 cycles. Fluorescence readings were taken at the end of each extension step. Quantification cycle (Cq) was determined when the software's automated baseline corrected fluorescence reached 200 RFU.

Kit Extractions

Three different silica-column kits were tested, including: Zymo ZR Viral DNA/RNA Kit (outdated protocol, D7021), Zymo Quick-DNA/RNA Kit (updated protocol, D7021), and the QIAquick PCR Purification Kit (28104, Qiagen). For all silica-column kits, fresh collection tubes were used after each spin and centrifugation speeds were set to 16,000×g. Centrifugation was performed on either an Eppendorf 5415D centrifuge (Eppendorf, Hauppauge, N.Y., USA) or a Thermo Fisher Scientific AccuSpin Micro 17R centrifuge (13-100-676). It was noted that the QIAquick protocol calls for 17,900×g, but instead was run at 16,000×g which was the max speed for the Eppendorf 5415D. For both Zymo kits, 750 µL lysed sample was prepared by mixing 125 µL sample with 125 µL Zymo 2×DNA/RNA Shield and 500 µL Viral DNA/RNA Buffer. For the Zymo ZR Viral DNA/RNA kit, 750 µL lysed sample was centrifuge for 1 min, 500 µL Zymo Viral Wash Buffer was centrifuged for 2 min, and 50 µL nuclease-free water was centrifuged for 30 s into a clean 1.5 mL tube. Optionally, either a dry spin or 300 µL TPW was centrifuged for 2 min in between the Viral Wash Buffer and elution steps. For the Zymo Quick-Viral DNA/RNA kit, 750 µL lysed sample was centrifuged for 1 min, 500 µL Zymo Viral Wash Buffer was centrifuged for 30 s, an additional 500 µL Zymo Viral Wash Buffer was centrifuged for 30 s, 500 µL 200 proof ethanol was centrifuged for 1 min, and 50 µL nuclease-free water was centrifuged for 30 s into a clean 1.5 mL tube. Optionally, either a dry spin or 300 µL TPW was centrifuged for 1 min in between the ethanol and elution steps. For the QIAquick PCR Purification Kit, 125 µL sample was mixed with 625 µL Buffer PB without indicator. 750 µL lysed sample was centrifuged for 30 s, followed by 750 µL Buffer PE for 30 s, a dry spin for 1 min, and 50 µL nuclease-free water for 1 min. Optionally, the dry spin was skipped or the dry spin was replaced with a 300 µL TPW and centrifuged for 1 min.

The Zymo Quick-DNA/RNA Viral MagBead (R2140) was tested. For the Zymo MagBead kit, 200 µL sample was mixed with 200 µL Zymo 2×DNA/RNA Shield, 4 µL Proteinase K, and 800 µL Zymo Viral DNA/RNA Buffer. 1204 µL was added to each tube, mixed with 20 µL MagBinding Beads, and placed on an UltraRocker Rocking Platform (1660709EDU, Bio-Rad, Hercules, Calif., USA) for 10 min at max speed. Tubes were transferred to a DynaMag-2 magnetic rack (12321D, Thermo Fisher Scientific) and manufacturer instructions was followed for the remainder of the protocol. Optionally, the 10 min dry step was skipped, or the dry step was instead replaced with the addition of 500 µL TPW. In the modified protocol for the Zymo MagBead kit, at least one additional minute was waited and a second aspiration was performed after each aspiration step in the manufacturer's protocol.

For studying kit buffer inhibitors, LAMP and qPCR reactions were spiked to 5×104 cp/rxn λ phage DNA (NEB) and supplemented with half-log dilutions of either Koptec 200-proof ethanol (V1001, Decon Labs, King of Prussia, Pa., USA), Viral RNA Wash Buffer 1× (R1034-2-48, Zymo Research, Tustin, Calif., USA), Buffer PE (19065, Qiagen, Germantown, Md., USA), Zymo DNA/RNA Shield 1× (R1200-125), Zymo Viral DNA/RNA Buffer (D7020-1-100), or Qiagen Buffer PB (19066) to the appropriate final concentration. For selecting the optimal TPW, LAMP and qPCR reactions were spiked with 1 µL of 5×104 cp/µL λ phage DNA, diluted to 10 µL, and an additional 1 µL was added of either nuclease-free water, 200 proof ethanol, isopropanol (BP2618-500, Thermo Fisher Scientific, Waltham, Mass., USA), 1-butanol (3000-04, Mallinckrodt Chemicals), isopentanol (2992-04, Mallinckrodt Chemicals), 1-hexanol (H13303-100 mL, MilliporeSigma, St. Louis, Mo., USA), 1-heptanol (H2805-250 mL, MilliporeSigma), 1-octanol (SHBH2844V, MilliporeSigma), 1-nonanol (131210-100 mL, MilliporeSigma), 1-decanol (2397563-50 g, MilliporeSigma), 1-undecanol (MKCG3271, MilliporeSigma), 2-dodecanol (D221503-5G, MilliporeSigma), 5 cSt silicone oil (317667-250 mL, MilliporeSigma), or Fluorinert FC-40 (ZF-0002-1308-0, 3M, St. Paul, Minn., USA).

RT Mix

The RT reaction contained 1× Isothermal Amplification Buffer, 0.5 mM dNTP Mix, 0.2 µM primers, 1 U/µL Riboguard RNase Inhibitor (RG90910K, Lucigen, Middleton, Wis., USA), and 0.15 U/µL WarmStart Rtx (M0380L, NEB). The extracted N. Gonorrhoeae RNA was diluted 10×in a separate tube and an additional 10× by adding 2.5 µL into the 25 µL reaction mix (100× dilution total). Kit extracts were spiked in the reaction mix by adding either 2.5 µL (10×) or 12.5 µL (2×). Water was added to a total reaction volume of 25 µL. Temperature was set to anneal for 5 min at 25° C., incubate for 10 min at 55° C., and inactivate for 10 min at 80° C. in a C1000 Touch Thermal Cycler (1851196, Bio-Rad).

Statistical Analysis Methods

Confidence intervals were calculated assuming the populations to be normally distributed and using a t statistic. For buffer inhibition experiments, statistical analysis was performed by a 1-tailed unequal variance t-test (N=9) comparing the water condition (control) to each buffer concentration ($H_1$: the mean is delayed). For the subsequent experiments, a 2-tailed unequal variance t-test ($H_1$: the means are different) was used. Non-detects were assigned the maximum possible $C_q$ measurement of 40 cycles or a TTP of 46.7 min to indicate the lack of amplification. Although this approach introduces some bias into the analysis, it is believed this is the best representation for handling non-detects (other alternatives include excluding the non-detects or assigning non-detect values to the average of those that amplified).

There are many potential sources of experimental variation (e.g. column-to-column, day-to-day generation of master mix, buffer dilutions, and pipetting errors), and these were controlled by running triplicates for different variables (buffer/MM dilutions, columns, technical qPCR/LAMP assays). A priori, it would have been assumed that independent variable are differences in buffer dilutions or differences among columns, and it was expected that the present technical replicates would display a narrow distribution. Instead, it was observed that there are large variations among technical replicates (e.g. 2 out of 3 amplify). Because large variations appear at the level of the technical replicate, each technical replicate was treated as an independent sample in the present statistical analysis.

Familywise error rate across the reported statistical analyses was not controlled (e.g. Bonferroni correction). All data have been made publicly available and, to strengthen the findings of this study, it was contemplated that a person skill in the art will perform further replication and validation, as there are numerous different potential applications and variables to examine (e.g. sample matrices, extraction kits, sequencing, etc.).

Example 1: Nucleic Acids Applications Integrated with TPW

Various high sensitivity applications using nucleic acids are known and/or expected to benefit by an integration with a TPW in accordance with the present disclosure, including polymerase chain reaction and additional amplification methods . . . .

Polymerase chain reaction (PCR) is a widely used tool in molecular biology for generating many nucleic acid (NA) copies from a starting DNA template. PCR may also be combined with reverse transcription (RT) to amplify many DNA copies from a starting RNA template. The amplified NAs then serve different purposes, such as detection, quantification, library preparation for sequencing, or generating constructs for cloning [1,2].

NA amplification is crucial in highly sensitive applications (few DNA copies) such as single-cells analyses or the detection of SNPs, cell-free circulating DNA, or pathogens [3-5]. Isothermal amplifications are an attractive alternative to PCR that eliminate the stringent temperature cycling requirements [6].

Specifically, loop-mediated isothermal amplification (LAMP) is faster than PCR and is especially promising for diagnostic devices in point-of-care settings [7,8]. PCR, RT, and LAMP typically require purified NAs as starting template; however, extracting purified NAs from raw, unprocessed samples is challenging [9]. Though commonly overlooked, the efficient and effective extraction of pure NAs is of paramount importance [10].

A primary function of NA extractions is to eliminate inhibitors. If inhibitors are transferred into the eluent, they can delay or completely inactivate downstream applications such as PCR and LAMP [11,12]. Inhibitors have also been implicated in failed RT, molecular cloning, and sequencing experiments [13-15].

It is contemplated two potential sources of inhibitors: (1) those present in the raw, unprocessed sample and (2) those introduced during the NA extraction [16]. There have been numerous studies demonstrating the adverse effects of inhibitors in challenging sample matrices, such as humic acids, food particles, cellular debris, urine, blood, and stool [11,12,17-25]. To remove these inhibitors, solid-phase extractions are an effective choice because they have been found to yield higher purity compared with other extraction methods [19,20,26-29].

The two most common solid-phase extraction methods use either spin columns or magnetic beads [28,30]. In both methods, the sample is first mixed with a lysis/binding buffer, the lysed sample contacts the solid phase allowing NAs to bind, the solid phase is cleansed with one or more wash buffers, and the NAs are eluted with water. Typically, the lysis/binding buffer contains a chaotropic salt (e.g., guanidinium isothiocyanate) whereas the wash buffer contains a high concentration of ethanol (or isopropanol). Any carryover of these extraction buffers (lysis buffer or wash buffer) into the eluent could be greatly inhibitory to downstream analyses.

The purified eluent contains NAs and any carried-over extraction buffers at their highest concentration. To run a downstream reaction, a volume of eluent is mixed with a volume of reaction mix. For research applications, it is standard to dilute the eluent 10× (e.g., 1 µL eluent and 9 µL reaction mix) [31,32], 25×(e.g., 1 µL eluent and 24 µL reaction mix) [33], or more [34,35]. At these high eluent dilutions, concentrations of inhibitors present in the eluent are reduced and thus their potential negative effects on the reaction are mitigated. However, the dilution of inhibitors equally dilutes the NAs, which may be detrimental when the original sample has low NA concentrations [3] and/or when high sensitivity is desired. For example, single nucleotide polymorphisms [5], cell-free circulating DNA [4], and single-cell analyses all require maximizing the concentration of NA loaded into the amplification mix.

Maximizing NA concentration is also important for infectious disease diagnostics and monitoring the water supply, food supply, and environment [32,36-38]. For these applications, a higher NA concentration could be achieved with a lower dilution (e.g., a 2.5×dilution would be 4 μL eluent and 6 μL reaction mix). The theoretical maximum NA concentration could be attained by eliminating the dilution altogether, which is only possible by adding eluent directly to a dried reaction mix (e.g., 10 μL eluent and dry reaction mix to make ~10 μL reaction). This can be achieved with lyophilization, wherein reagents are freeze-dried to a powder, or other approaches for generating dry reaction mixes. The use of dry reagents has additional benefits: simple assay protocols, lenient reagent-storage conditions, and long reagent shelf-life, all of which are desirable characteristics for the development of point-of-care devices. However, in using low dilutions or no dilution, extraction buffers in the eluent are used at higher concentrations which may have adverse effects on downstream reactions.

Few studies have directly investigated inhibition resulting from solid-phase extraction kit buffers [39,40].

The carryover of kit buffers, the extraction protocols can be modified to include an additional two-phase wash (TPW) according to the disclosure that integrates with the existing manufacturer protocols [41].

In particular, it has been shown and is expected that a TPW according to embodiments herein described to reduce inhibition arising from buffer carryover in commercial extraction kits from well-known suppliers, in particular concern when using low eluent dilutions (<2.5×) for both commercial silica-column and magnetic-bead extractions (following manufacturer protocols).

Example 2: TPW in Combination with Centrifugation Spin Column Extraction and in Magnetic Beads —Preparation Reduced the Presence and Prevalence of Inhibitors in Buffers It was contemplated that the issue of extraction buffer carryover in commercial NA extraction kits could be addressed by the addition of a TPW. The TPW is composed of an immiscible compound that phase separates with water, which was added it in between the wash step and the final elution (FIGS. 1a bottom, 1b bottom). The TPW has a water solubility equal to or less than 0.05 g per 100 mL at 25° C. at 1 atm pressure with water having a solubility in the removing agent of less than 10 g per 100 mL at 25° C. at 1 atm pressure.

It was further contemplated to develop a TPW that would be simple, inexpensive, and that would integrate easily with existing protocols. The TPW greatly reduce buffer carryover and improve downstream assay performance. In the present study (FIG. 1 Panel c), incorporating the TPW recovered qPCR (2.5×dilution of kit extract) and provided the expected Cq of ~20 cycles. This was a drastic performance improvement compared with the complete reaction inhibition that was observed when the same dilution was run using the manufacturer protocol.

It was therefore evaluated how the buffers from solid-phase silica-column centrifugation and magnetic-bead extraction kits are carried over into the eluent and inhibit downstream amplification reactions. Using kits from leading manufacturers, it was repeatedly observed that as expected, a high (10×) dilution of eluent showed little to no inhibition of qPCR or LAMP reactions. However, carried-over extraction buffers caused delays or completely inhibited amplification and reverse transcription at low (2-2.5×) dilutions of eluent. Reaction inhibition was observed using two different silica-column centrifugation kits (3 protocols: Zymo ZR, Zymo Quick, Qiagen QIAquick) and a magnetic-bead kit (Zymo MagBead) when using the manufacturer protocols.

In view of the above, the protocols for standard commercial kits were modified to be performed in combination with TPW according with a centrifugation sample-preparation protocol schematically shown in FIG. 1 Panel a, and a non-centrifugation (magnetic beads) sample-preparation protocol schematically illustrated in FIG. 1 Panel b.

To eliminate the confounding effects of NAs or inhibitors originating from the sample, NA extractions was performed on pure water samples (see Example 9, Figure Panel 9). When extracting from pure water samples, it was referred to the eluent as the "kit extract," which only contains water and inhibitors originating from buffers in the extraction kits.

A centrifugation-based NA (nucleic acid) extraction was tested using a Zymo ZR Viral DNA/RNA Kit and followed the manufacturer's protocol.

Next, the kit extract was mixed into a qPCR reaction spiked with λ phage DNA at either a 10× dilution (1 μL kit extract, 0.5 μL template DNA, 5.5 μL reaction mix) or 2.5×dilution (4 μL kit extract, 0.5 μL template, 5.5 μL reaction mix).

Heavily diluted purified λ phage DNA was used to ensure no inhibition originated from the template. The 10× and 2.5×dilution reactions contain different volumes of kit extract, but each had a final volume of 10 μL and contained the same concentration of λ phage template, X phage primers, and qPCR components.

qPCR was run on a thermocycler for 40 cycles while readings at the end of each cycle was taken. If the kit extracts have no inhibitory effect, it would be expected that the same quantification cycle (Cq) for both reactions would result. Given the amount of input DNA (5×10⁴ copies), the amplification should have occurred at ~20 cycles.

Using the centrifugation sample-preparation protocol (FIG. 1 Panel a) and a 2.5×dilution of kit extract, amplification in qPCR was completely inhibited (FIG. 1 Panel c). In contrast, using the 10× dilution, all three kit extracts (three separate columns) amplified at ~20 cycles. The only variable that differed between the two conditions was that the 2.5×dilution (4 μL kit extract) contained four times the concentration of buffer compared with the 10× dilution (1 μL kit extract). This result led to a conclusion that carryover of inhibitory buffers is inhibiting the qPCR reaction.

It was understood that carryover results from residual buffer trapped in the column that is picked up during elution. Although centrifugation moves most of the extraction buffers to the waste tube for removal, some lysis/binding buffer and/or wash buffers may remain stuck in the column after each centrifugation step (FIG. 1 Panel a).

A possible explanation which is not intended to be limiting is these effects could occur due to physical entrapment, surface tension, or physicochemical interactions with either the silica column or the walls of the tube. Furthermore, it is possible for some of the inhibitory components contained in the buffer to become unevenly trapped on the column. During the elution step, water could mix with these trapped buffers/inhibitors and carry them into the final eluent. It was emphasized that for a standard elution volume of 50 μL water, even low volumes of carryover may correspond to a sufficiently inhibitory percentage of buffer in the eluent. For example, 500 nL buffer carryover corresponds to 1% buffer in the eluent and 2.5 μL corresponds to 5% buffer in the eluent.

Buffer carryover also occurred when using magnetic-bead extraction. In these protocols, magnetic beads that bind to NAs in the appropriate buffer conditions are added to the sample. Extraction buffers are then added (lysis and multiple washes) by sequential rounds of buffer addition, magnetization to pull the magnetic beads to the side of the tube, and aspiration of each buffer. (FIG. 1 Panel b).

For the elution step, water is added which releases the NAs from the magnetic beads, the magnetic beads are drawn to the sides of the tube, and the eluent is transferred to a clean tube. During this process, however, some buffer components may stick to the magnetic beads or adhere to the walls of the tube. Thus, although most of the buffers are removed during aspiration, a low concentration of extraction buffers transfer into the eluent when using the standard manufacturer protocols.

An explicit examination of the extent of buffer carryover was performed for magnetic-bead extractions using low and high dilutions of eluent according to the schematic approach shown in FIG. 1 Panel b according with the experiments reported in detail in Example 8.

Example 3: Effects of Buffer Inhibition on Amplification

Having established that buffer carryover is a problem as shown by the exemplary experiments of Example 2, it was next aimed to better understand the effects of inhibition on amplification in qPCR and LAMP. Extraction buffers from a Zymo viral DNA/RNA kit and a Qiagen PCR purification kit were selected.

These two commercial kits in particular were chosen because they both utilize minimal protocols (lysis, wash, elute) with no added steps (e.g. bacterial pellet spins, proteinase K, lysozyme, DNase/RNase, filtration, etc.). Specifically, an experiment was conducted to identify the concentration at which each buffer inhibits qPCR and LAMP. First, buffers were added at half-log dilutions (from 10% down to 0.032%) into λ phage spiked qPCR or LAMP reactions (1 µL diluted buffer, 1 µL template, 8 µL reaction mix).

Experiments are designed to see whether qPCR and LAMP were affected differently by inhibitors. It is contemplated that there would be differences between the two amplification methods because qPCR amplification is temperature-gated whereas LAMP amplifies continuously. Previous literature on this topic shows "mixed results;" many studies have shown that LAMP is more robust than PCR in the presence of inhibitors [47-50] whereas others have shown that inhibition of PCR and LAMP depends on which inhibitor was used [40].

Figure 2:
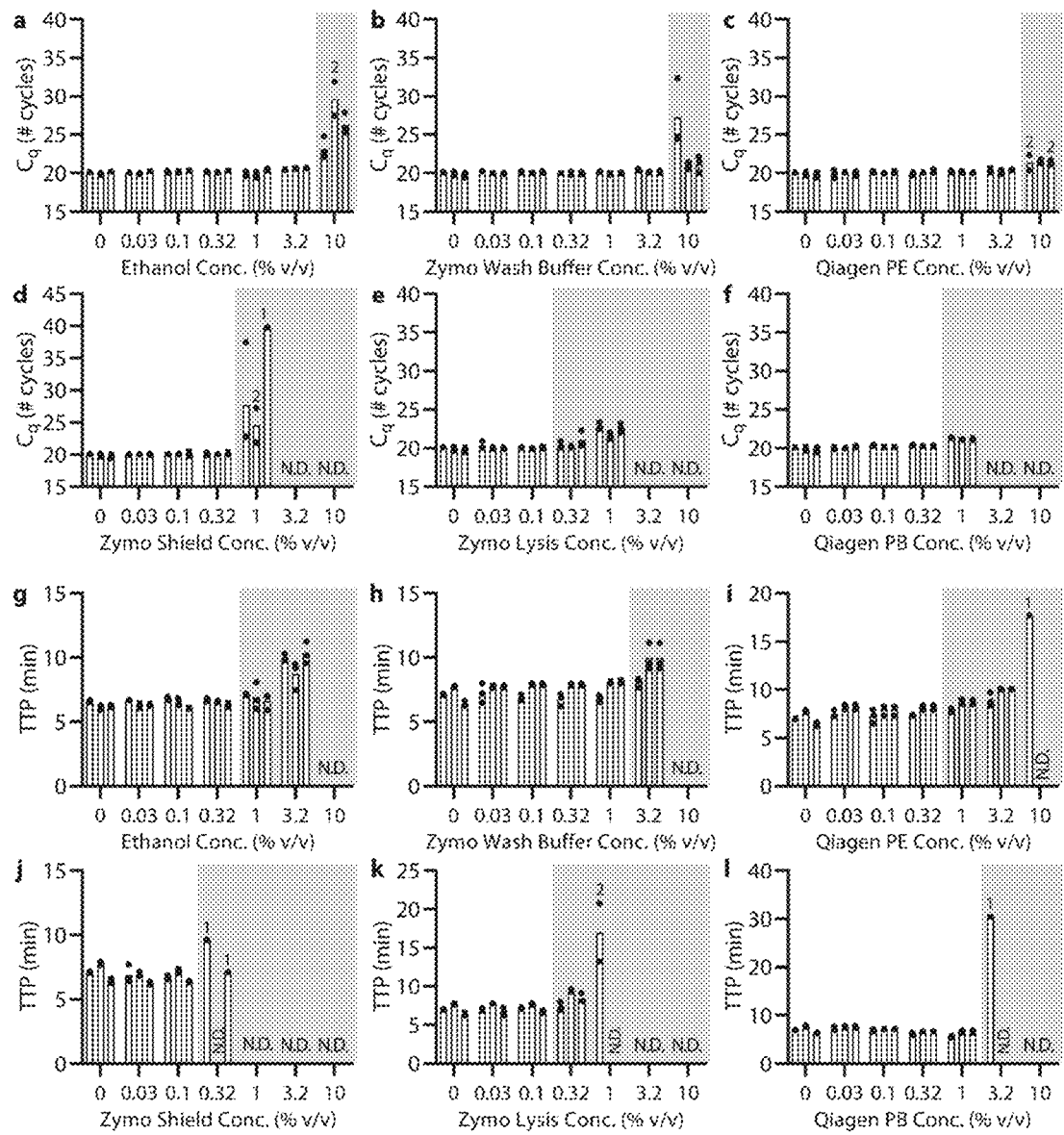
FIG. 2 shows in panels (Panels a-f) qPCR and (Panels g-l) LAMP experiments that demonstrate reaction inhibition from NA extraction kit buffers. Quantification cycles (Cq) for qPCR or time to positive (TTP) for LAMP spiked with $5\times10^4$ copies λ phage DNA and primers with increasing concentrations of extraction kit buffers. For ethanol dilutions (Panels a, g), three separate amplification mixes were each combined with an independent ethanol dilution series. All remaining buffer dilutions (Panels b-f, h-l) shared the same set of three amplification mixes (same 0% condition), and each amplification mix was combined with an independent dilution series of each buffer. Each bar is the average of qPCR or LAMP technical triplicates (black circles). Where shown, numbers above a bar indicate the number of samples that amplified out of technical triplicates. Gray shading indicates when inhibition (>0.5 cycles or >0.5 min) was observed according to changes in Cq or TTP. Samples marked N.D. were not detected within either 40 cycles or 40 min.

The results are reported in FIG. 2 and in particular in FIG. 2 panels (a-f) report the quantification cycles (Cq) detected in the qPCR experiments and in FIG. 2 Panels (g-l) report the time to positive (TTP) results of the LAMP experiments LAMP.

It was found that all extraction buffers were inhibitory to both types of reactions, but at different concentrations (FIG. 2). As a control, for each kit, the protocol was run with 0% buffer and it was found that amplification with qPCR yielded a Cq of ~20.0±0.3 cycles and amplification with LAMP had a TTP of 7.1±0.6 min. As a general trend, it was found that wash buffers (ethanol, Zymo Viral Wash Buffer, and Qiagen Buffer PE; FIG. 2 Panels a-c,g-l) were less inhibitory than lysis buffers (Zymo DNA/RNA Shield, Zymo DNA/RNA Viral Buffer, and Qiagen Buffer PB; FIG. 2 Panels d-f,j-l). For qPCR, a statistically significant (P<0.05) Cq delay of at least 0.5 cycles was observed for wash buffer concentrations starting at 10% (Figure Panels 2a-c, Table 1) and for lysis buffers starting between 0.32-1% (FIG. 2 Panels d-f, Table 1). For LAMP, a statistically significant (P<0.05) TTP delay of at least 0.5 min was observed for wash buffer concentrations starting at 1-3.2% (FIG. 2 Panels g-i, Table 2) and for lysis buffers starting at 0.32-3.2% (FIG. 2 Panels j-l, Table 2). These results imply that the extent of inhibition on qPCR and LAMP reactions is inhibitor-dependent, which may help explain the "mixed results" in the literature.

Next, the presence of inhibitors at very low concentrations was observed using melting temperature (Tm), as compared with Cq, TTP, or endpoint fluorescence (FIGS. 9-12). Interestingly, it was observed that the presence of extraction buffers raised or lowered the Tm of the DNA product even at very low concentrations (1%-3.2% for ethanol buffers, 0.32%-1% for lysis buffers). Detecting a change in the Tm of an NA product is expected to be a useful tool for diagnosing the presence or absence of extraction buffers in a reaction.

Example 4: Inhibition in Samples with Low NA Concentrations

The effects of buffer-related inhibition in samples containing low NA concentrations were tested.

For applications requiring high sensitivity (e.g., single-cell sequencing, cell-free circulating DNA, SNP genotyping, and diagnostics), amplification reactions are often run at or near the limit-of-detection (LOD). Samples starting with low NA concentrations thus require the polymerase to replicate more DNA than in samples that start with a high NA concentration. Therefore, it was hypothesized that the inhibition effect resulting from buffer carryover would be stronger for these low NA samples (and detected as delayed Cq or TTP).

Additionally, it has been recorded that PCR reactions with different primers and targets can respond differentially to inhibitors 11. To ensure the inhibitory effects that was observed with λ phage DNA were not specific to just the set of DNA and primers that were used, this experiment was run using *Escherichia coli* DNA and *E. coli* primers.

With qPCR, it was found that the cycle delay as a result of buffer inhibitors was higher at lower NA concentrations (Figure Panels 3a,b). The experiment started with a medium concentration of target ($5 \times 10^4$ *E. coli* 23S copies) and 4-fold dilutions down to 0.05 copies with either control (no inhibition) or in the presence of 1% Zymo Viral DNA/RNA Buffer were test. 1% lysis buffer was chosen because it had been found 1% lysis buffer to be weakly inhibitory and it was suspected inhibition may worsen with decreasing DNA concentration.

Figure 15:
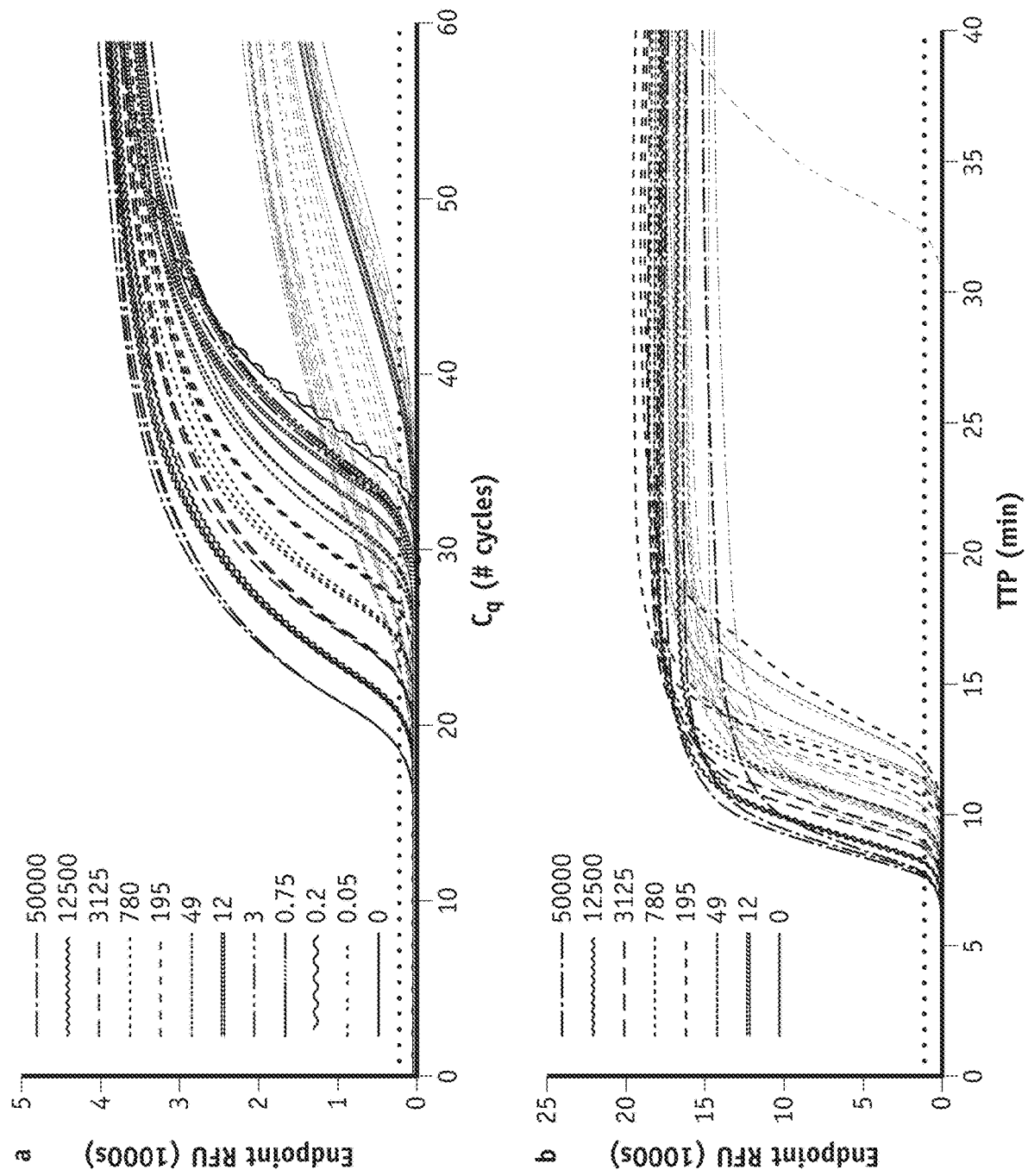
FIG. 15 shows in top panel (Panel a) qPCR and bottom panel (Panel b) LAMP amplification curves with (dashed lines) or without (solid lines) Zymo Viral DNA/RNA Buffer for 4-fold dilutions of *E. coli* 23S rRNA gene copies. For qPCR 1% lysis buffer was used and for LAMP 0.32% lysis buffer was used. Time-to-positive (TTP) threshold of 200 RFU for qPCR or 1000 RFU for LAMP is drawn as a dotted black line. Legend indicates the number of *E. coli* 23S rRNA gene copies/rxn. The qPCR amplification curves correspond to the experiment in FIG. 3 of the main text.

The control reactions matched set expectations; it was found that $5 \times 10^4$ copies yielded a Cq of 19.55±0.04, the cycle increased by ~2 for every 4-fold dilution, and the target down to 3 copies was detected. Compared with the 1% lysis buffer condition, it was found that the reaction for the highest concentration ($5 \times 10^4$ copies) was greatly impaired by 4.65±0.13 (95% CI: 4.33-4.97) cycles (Figure Panel 3b). The delay worsened and variance increased as the NA concentration was decreased. At 3 copies/rxn, there was an 8.45±0.94 (95% CI: 6.11-10.79) cycle delay and all three triplicates amplified, but it is needed to increase the number of cycles in this experiment in order to detect the delayed Cq. Results of the experiment showed that the presence of lysis buffer caused a decrease in the amplification efficiency with each cycle. This conclusion was also supported by the shallower amplification curves (FIG. 15).

Figure 3:
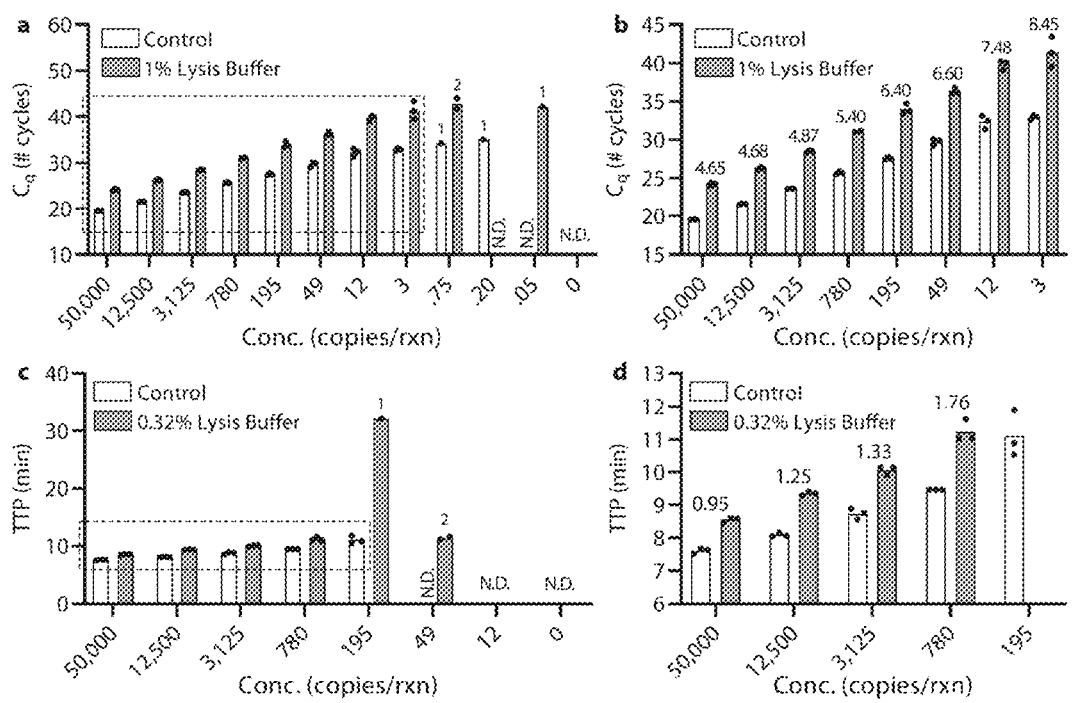
FIG. 3 shows in panels (Panels a-b) qPCR and (Panels c-d) LAMP experiments targeting $E.$ $coli$ 23S rRNA gene, which shows increased impact of reaction inhibition at low NA concentrations. (Panel a) qPCR and (Panel c) LAMP spiked with 4-fold dilution series of $E.$ $coli$ 23S rRNA gene copies and comparing with and without Zymo Viral DNA/RNA Buffer. Each bar represents the average of technical qPCR or LAMP triplicates (black circles). Numbers above a bar indicate the number of samples which amplified if not all triplicates were detected. Dashed boxes indicate axes for zoomed-in graphs of (Panel b) qPCR and (Panel d) LAMP. Numbers above each pair of bars indicate the difference in either Cq or TTP between the control and the reaction with added lysis buffer. Samples marked N.D. were not detected within either 60 cycles or 40 min.

With LAMP, it was also found that the delay as a result of buffer inhibitors was higher at lower NA concentrations (FIG. 3 Panels c,d). Because LAMP was more sensitive to inhibitors than qPCR, the control was compared to 0.32% lysis buffer. The control reaction TTP was 7.61±0.08 min at 5×10⁴ copies and the TTP increased with increasing dilutions up to 11.1±0.7 min at 195 copies. LAMP failed to amplify at higher concentrations of DNA than when using qPCR (amplification for 3 or fewer copies was stochastic). The addition of 0.32% lysis buffer caused a 0.95±0.06 (95% CI: 0.80-1.10) min delay in TTP at the highest concentration (5×10⁴ copies/rxn), which increased as the *E. coli* DNA concentration was lowered to a 1.76±0.19 (95% CI: 1.29-2.23) min delay at the lowest detectable concentration (780 copies/rxn). At lower concentrations, amplification was stochastic. LAMP was unable to detect down to 195 copies/rxn in the presence of lysis buffer, indicating a loss in analytical sensitivity that was not observed with qPCR. Another difference between LAMP and qPCR is that although the LAMP TTP was delayed, the amplification rate and endpoint fluorescence in LAMP were not strongly affected (FIG. 15).

Example 5: Identifying an Effective TPW

Next, a suitable wash buffer was identified that would reduce the carryover of extraction buffer and integrate easily into existing protocols.

The ideal wash buffer would be added after the final ethanol wash but prior to the elution and it would have the following properties: (1a) it would be non-inhibitory or (1b) it would not transfer to downstream assays such as qPCR or LAMP, (2) it would remove previous washes from the column by an appropriate combination of solid-liquid and liquid-liquid interfacial properties and solubility of inhibitory components, and (3) it would not prematurely elute NAs from the column. Criterion 1a was investigated directly by performing qPCR and LAMP reactions. Reactions were spiked with λ phage DNA, diluted up to 10 µL, and an additional 1 µL of different wash buffer candidates was added to a total of 11 µL. As additional wash candidates, increasing chain lengths of primary alcohols (or secondary alcohols if the primary form was unavailable), 5 centistokes (cSt) silicone oil, and FC-40 fluorocarbon oil (FIG. 4 Panels a,b) were tested. As an experimental control, a "No Additive" condition was tested, which was a 10 µL reaction with optimized reaction conditions and no inhibitors. To control for the effects of a 1 µL dilution on the reaction, a "Water" condition which was an 11 µL reaction with no inhibitors was also tested.

Figure 4:
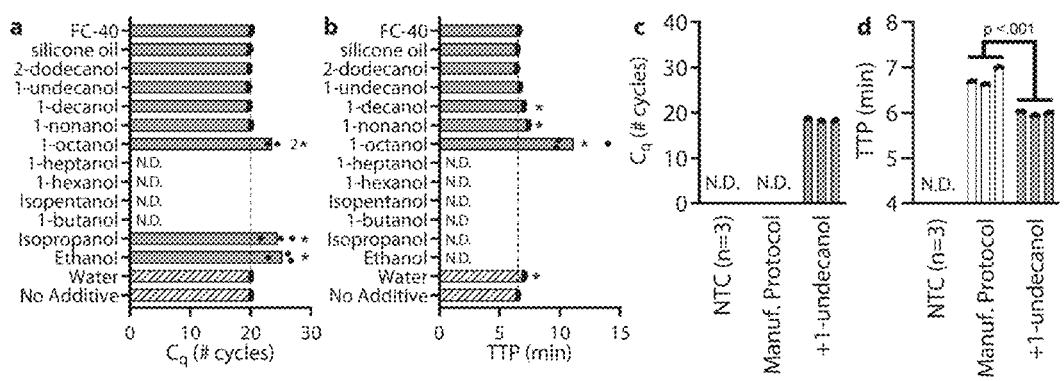
FIG. 4 shows identification of the most effective TPW in (Panel a) qPCR and (Panel b) LAMP reactions and subsequent validation of 1-undecanol as a candidate TPW with (Panel c) qPCR and (Panel d) LAMP at low eluent dilutions. TPW candidates for (Panel a) qPCR and (Panel b) LAMP reactions were spiked with $5\times10^4$ copies λ phage DNA and primers, made to 10 μL, and 1 μL of each wash candidate was added to yield 11 μL total. The number 2 next to the 1-octanol bar indicates that only two of the three replicates amplified. The dashed lines show the Cq or TTP of the uninhibited 10 μL "No Additive" control. (c) qPCR with 2.2×diluted eluent and (Panel d) LAMP with 2×diluted eluent on a λ phage DNA sample extracted with a Zymo Quick-Viral DNA/RNA kit. Protocol was performed according to manufacturer instructions as provided or with an additional TPW (+1-undecanol) between the ethanol wash and elution steps. Each bar represents the average of technical triplicates (black circles). 6 extractions (3 silica columns×2 conditions) were run and the same eluent for both the qPCR and LAMP analyses was used. Samples marked N.D. were not detected within either 40 cycles or 40 min. NTC, no-template control. (Panels a,b) It was shown whether TPW candidates fell within the 99% CI of the "No Additive" control (qPCR: 20.01-20.17, LAMP: 6.25-6.83) with outliers indicated with a *. (Panel d) It was shown whether the average TTP was statistically different between the manufacturer protocol and the +1-undecanol condition using a t-test.

The "No Additive" control case showed a qPCR Cq of 20.09±0.01 cycles (95% CI: 20.07-20.12) and a LAMP TTP of 6.54±0.05 min (95% CI: 6.42-6.66). It was noted that 1 µL in 11 µL is a large fraction of the reaction mix (~9%), so buffer carry-over concentrations were overestimated compared to normal operating conditions. The "Water" control showed no delay for qPCR and a 0.55 min delay for LAMP due to the dilution of LAMP reactants. For both qPCR and LAMP reactions, it was found that long-chain alcohols with >9 chain lengths, silicone oil, and FC-40 were non-inhibitory for qPCR (within 1 cycle) and LAMP (within 1 min) compared to the "No Additive" condition (FIG. 4 Panels a,b). Octanol showed delays for qPCR (3.54 cycle difference) and LAMP (4.63 min difference), and only 2 out of 3 replicates amplified for qPCR. All alcohols with <8 chain lengths either had delayed amplification or the reaction was completely inhibited. Because long-chain alcohols, silicone oil, and FC-40 showed little to no inhibition of qPCR and LAMP, these candidates fulfilled criterion 1a.

These non-inhibitory wash candidates (long-chain alcohols, silicone oil, and FC-40), which were referred to as TPW, have low solubility in water (Table 7) and resulted in phase separation (Table 8).

Next, criterion 1b (ensuring that the TPW does not transfer to qPCR and LAMP) was evaluated as well as criterion 2 (the ability of the TPW to remove previous washes from the column) by running a NA extraction with or without TPW and adding the resulting eluent into qPCR and LAMP (FIG. 4 Panels c,d). Of our TPW candidates, 1-undecanol was selected for further evaluation because (i) it was non-inhibitory for qPCR and LAMP reactions and (ii) as an alcohol, 1-undecanol may function similarly to ethanol- or isopropanol-based washes. In these experiments (testing criteria 1*b* and 2), a commercially purified λ phage DNA sample was first diluted to 2.5×10⁶ copies and ran an NA extraction using the Zymo Quick-DNA/RNA Viral Kit. The experimental procedure either followed the manufacturer protocol or added an additional 300 µL 1-undecanol wash in between the Viral Wash Buffer and elution step. Using the manufacturer's protocol, the resulting eluent is approximately 49 µL, but with the added TPW the resulting eluent is approximately 48 µL aqueous phase and ~1-2 µL 1-undecanol phase. To emphasize any potential inhibitory effects, a low dilution of eluent was used. For qPCR, a 2.2×dilution was achieved by adding 4.5 µL of eluent, 0.5 µL primers, and 5 µL qPCR reaction mix. For LAMP, a 2×dilution was achieved by adding 5 µL eluent, 0.5 µL primers, and 4.5 µL reaction mix. During the transfer of eluent into the reaction mix, it is noticed that the phase separation yielded by the TPW resulted in minimal transfer of the TPW into downstream reactions (criterion 1b). The ~1-2 µL TPW separates from the aqueous phase and adheres to the walls of the tube, making it is easy to use a pipette to capture just the eluent.

Overall, it was found that the addition of the 1-undecanol TPW greatly improved qPCR and LAMP performance at low dilution (FIG. 4 Panels c-d). Without the inclusion of the TPW, qPCR run at low dilution of eluent and following the manufacturer's NA extraction protocol led to failed amplification in all 9 samples. However, with the TPW, the reaction completely recovered with a Cq of 18.46±0.22 cycles. For LAMP and low dilution, it was found that the manufacturer protocol amplified in 6.78±0.17 min whereas modified TPW protocol as described herein amplified in 6.00±0.04 min (FIG. 4 Panel d). Not only was there a 0.78 min reduction in TTP ($p<0.01$), variance was also reduced. Observing improvements for both qPCR and LAMP, it was concluded there was reduced carryover of previous washes (criterion 2).

To confirm the present result that the 1-undecanol TPW with low eluent dilutions led to significant improvements in qPCR and LAMP, this experiment was repeated twice more and similar results were found. In total (FIGS. 4-5), 27 reactions (9 columns) were run following the manufacturer protocol and compared to 27 reactions (9 columns) with the added 1-undecanol wash. Each set of 3 columns showed a statistically significant ($p<0.01$) difference comparing with and without 1-undecanol wash ($p<0.01$) for qPCR and LAMP. For qPCR (triplicate) with the manufacturer protocol, it was found that 2/27 reaction wells with Cq between 18-22 cycles, 3/27 wells were delayed by 4 or more cycles, and 22/27 wells did not amplify. Of the 5 wells that amplified, the average Cq and standard deviation was 28.6±9.2 cycles. Meanwhile, adding the 1-undecanol wash resulted in 25/27 wells with Cq between 18-22 cycles, 2/27 wells with a delayed Cq, and all reactions amplified. The average Cq with the added 1-undecanol wash was 19.7±2.5 cycles. In addition to more samples amplifying, it was found that the Cq dropped and the measured variance among samples was reduced, thereby improving the accuracy, speed, and robustness of the diagnostic assay. For LAMP (triplicates), all 27 wells with TPW (10.23±0.06 min) had a faster TTP than all 27 wells following manufacturer protocols (11.36±0.27 min). Again, it was found that the 1-undecanol wash improved the speed and robustness (reduced variance) of the assay.

Figure 5:
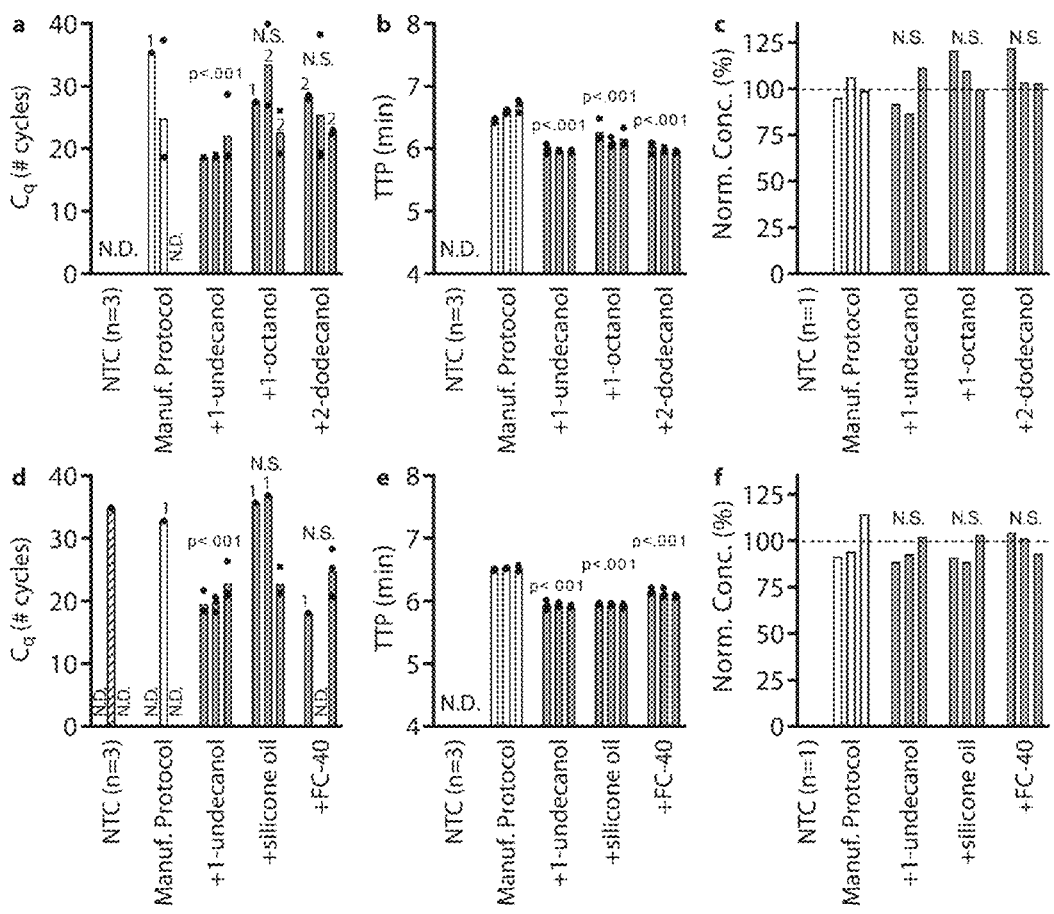
FIG. 5 shows comparison of the performance of different TPWs with eluent at 2.2×dilution in qPCR (Panels a,d), 2×dilution in LAMP (Panels b,e), and 100×dilution in digital PCR (dPCR) (Panels c,f). Samples were spiked with $2.5\times10^6$ copies λ phage DNA and extracted in 50 μL water with a Zymo Quick-Viral DNA/RNA kit. Each manufacturer's protocol (Manuf. protocol) was compared with the same protocol plus an additional TPW of either 1-undecanol, 1-octanol, 2-dodecanol, silicone oil, or FC-40. To observe inhibition, a low eluent dilution was used in qPCR and LAMP with λ phage primers. To get a highly accurate quantification of NAs (for comparing these results), each sample was run using dPCR with a high dilution of eluent (100×), which eliminates the effects of inhibitors. Each bar represents the average of qPCR or LAMP technical triplicates (black circles) or single dPCR measurements. 24 extractions (3 silica columns×8 conditions) were run and the same eluent was used to run the qPCR, LAMP, and dPCR analyses. Where shown, numbers above a bar indicate the number of samples which amplified if not all triplicates were detected. Dashed lines (Panels c and f) indicate the average NA recovery following manufacturer protocol. Samples marked N.D. were not detected within 40 cycles by qPCR or 40 min by LAMP. (Panels a-f) For each of the five TPW candidates, it was shown whether the mean value was statistically different from the manufacturer protocol by t-test. N.S. stands for not significant (P>0.05).

Next, it was investigated whether this result was specific to 1-undecanol or TPWs in general (FIG. 5 Panels a,b,d,e). For this experiment, 2-dodecanol was chosen because it is the longest chain alcohol that was tested and 1-octanol because it is the shortest chain alcohol for which both qPCR and LAMP still amplified (FIG. 4 Panels a,b). 2-dodecanol performed similarly to 1-undecanol because they are compositionally similar and both were found to be non-inhibitory for qPCR and LAMP (FIG. 4 Panels a,b). Accordingly, it was expected that 1-octanol might perform worse given its higher solubility and previously observed delays. Also silicone oil and FC-40 were chosen to evaluate nonalcoholic forms of TPW. The result of present study found that all five TPW candidates outperformed the manufacturer protocol. In qPCR reactions, 7/9 reactions amplified with 2-dodecanol wash, 5/9 for 1-octanol, 5/9 for silicone oil, and 4/9 for FC-40 whereas without the TPW (following the manufacturer protocol) amplification often failed (5/27). For LAMP, all TPWs conditions amplified with a faster TTP than manufacturer protocol. (P<0.01).

It was noted that 1-undecanol and 2-dodecanol performed best (greatest number of successfully amplified qPCR reactions and faster LAMP TTPs) because these two TPW candidates met all of set criteria (1a. non-inhibitory, 1b. low transfer to downstream assays, 2. remove previous wash, and 3. do not elute NAs). Meanwhile, it was expected that 1-octanol performs slightly worse because 1-octanol is inhibitory to qPCR and LAMP (criterion 1a). However, these inhibitory effects are minimal because 1-octanol phase-separated from the eluent and, as a result, only a small volume of 1-octanol was carried-over into the downstream reactions (criterion 1b). Lastly, it was observed that both silicone oil and FC-40 demonstrated slightly worse performance than the other TPW candidates. A potential explanation for the poor performance of silicone oil and FC-40 is that during the TPW step, the alcohols mixed with the previous ethanol-based wash whereas silicone oil and FC-40 did not (Table 8). As a result, this allows the alcohol-based TPWs to dilute and more effectively cleanse droplets of ethanol trapped in the column (criterion 2).

Next, it was evaluated whether or not the TPW meets criterion 3 (NAs are effectively eluted from the column during the TPW or lost due to premature elution or incomplete elution) (FIG. 5 Panels c,f). For this experiment, a 100× dilution was used to reduce buffer concentrations to non-inhibitory levels followed by digital PCR (dPCR); dPCR is a highly sensitive method for quantifying NAs that detects the same target (same primers) as qPCR. Although triplicates are commonly tested for qPCR and LAMP, for dPCR experiments duplicates measurements were run each with more than 15,000 individual reactions. The results from both experiments were merged and Poisson distribution was used to calculate the final concentration using Bio-Rad's QuantaSoft analysis software. All dPCR concentrations were normalized to the average concentration of the three extractions following the manufacturer protocols. It was found that the TPW did not appreciably affect the NA recovery, fulfilling the final criterion (3) as described herein for an ideal wash buffer. Furthermore, all highly diluted dPCR measurements showed similar NA recovery between manufacturer protocol and TPW conditions, whereas low dilutions resulted in stark differences for both qPCR and LAMP, further confirming that inhibitors are responsible for delays in Cq and TTP.

Example 6: TPW Validation for Different Kits with High and Low Dilution

To evaluate the generality of the approach as described herein and better understand the mechanism, three extraction kit protocols with and without the added TPW were tested. It was evaluated whether there is a difference in downstream amplification between high eluent dilution (10×) and low eluent dilution (2× or 2.5×). Zymo's kit D7021 using either the newer protocol (Zymo Quick-DNA/RNA Viral Kit) or the older protocol (Zymo ZR Viral DNA/RNA Kit) was therefore evaluated. Although both protocols use the same buffers, the Zymo Quick Kit has three wash steps (two viral wash buffers and one ethanol wash) whereas the Zymo ZR kit has one viral wash buffer step. By default, the Zymo kits do not include a "dry spin." The Qiagen QIAquick uses a different set of buffers, has one wash step, and by default includes a "dry spin." In this experiment, all kits extractions were performed on pure water (there are no NAs during the extraction, FIG. 9) to ensure that only the effects of buffer inhibitors were evaluated. The subsequent qPCR and LAMP reactions were then spiked with 5×10^4×DNA copies. As a control, water was added to qPCR or LAMP (rather than kit extract) to represent the best-case reaction without inhibitors ("No Extract").

No inhibition at 10× dilution following manufacturer protocols (FIG. 6) was observed, which confirmed that the standard 10× or more dilution into qPCR and LAMP prevents the inhibitory effects that was observed at lower dilutions. With a 10× dilution, it was noticed that the "No Dry Spin" condition using the Qiagen kit with LAMP resulted in ~1 min delay. It was noted that the Qiagen kit manufacturer protocol requires the dry spin. Without the dry spin, it was noticed the Qiagen kit extract had substantially more volume (~65 µL) than when the dry spin was included (~49 µL). This implies ~16 µL (25%) carryover of Buffer PE into the kit extract. The volume of kit extract from Zymo kits, however, was not noticeably affected by the addition of the dry spin (~49 µL with or ~49 µL without).

Figure 14:
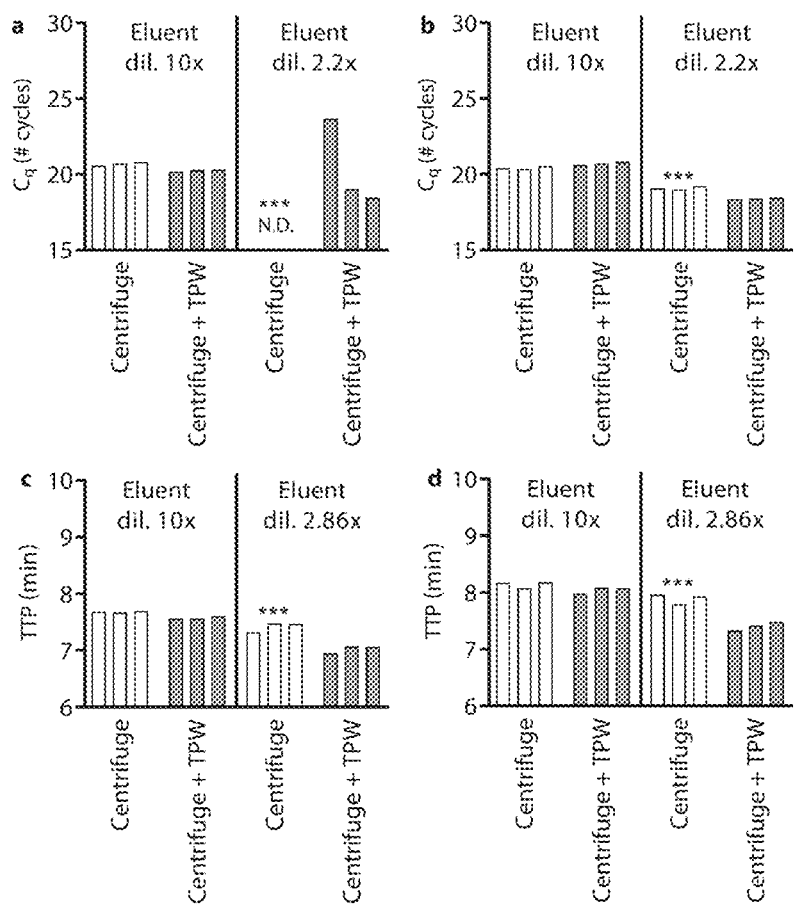
FIG. 14 shows evaluation of extraction buffer inhibition on different assays and improvements due to the addition of a TPW. The (Panel a) NEB SsoFast mix was compared to the (Panel b) NEB Luna mix and a (Panel c) manually prepared LAMP mix was compared to an (Panel d) NEB pre-made LAMP mix. Kit eluent was obtained by performing a Zymo Quick-DNA/RNA Viral Kit on 2.5×10$^5$ copies λ phage DNA and eluting with 50 μL water. The left side of each graph shows high dilution and the right side shows low dilution. Six silica-column extractions in total was run and the same kit extract was shared among the high and low dilutions of all assays. Samples marked N.D." indicate not detected within either 40 cycles (qPCR) or 40 min (LAMP). All negative controls were clean (not shown). For the low eluent dilution conditions, how many replicates following the standard centrifugation protocol fell outside of the 95% confidence interval was determined for the corresponding centrifuge +TPW condition (indicated by number of *).

Example 7: TPW Validation for Different Reaction Mixes with High and Low Dilution To understand how different reaction mixes respond to buffer carry-over, NEB's SsoFast mix was compared to NEB's Luna mix and manually prepared LAMP mix as disclosed herein to NEB's pre-made LAMP mix. Using a Zymo Quick-DNA/RNA Viral Kit for extractions, it was found that the Luna mix amplified at a 2.2×dilution of kit eluent whereas the SsoFast mix did not (FIG. 14 Panels a,b). This result implies that the Luna kit is more tolerant to the Zymo extraction buffer inhibitors than to those in the SsoFast mix. When experiments with and without the TPW were compared, it was again observed that the inclusion of the TPW improved downstream assay performance, recovering amplification for the SsoFast mix and reducing the Cq from 19.1 to 18.4 cycles for the Luna qPCR assay. The manually prepared LAMP mix performed similarly to the pre-made LAMP kit, and again the TPW improved performance at low eluent dilution (2.86×). The TTP for the home-made mix was reduced from 7.4 to 7.0 min and the TTP for the pre-made mix was reduced from 7.9 to 7.4 min (FIG. 14 Panels c,d).

Figure 6:
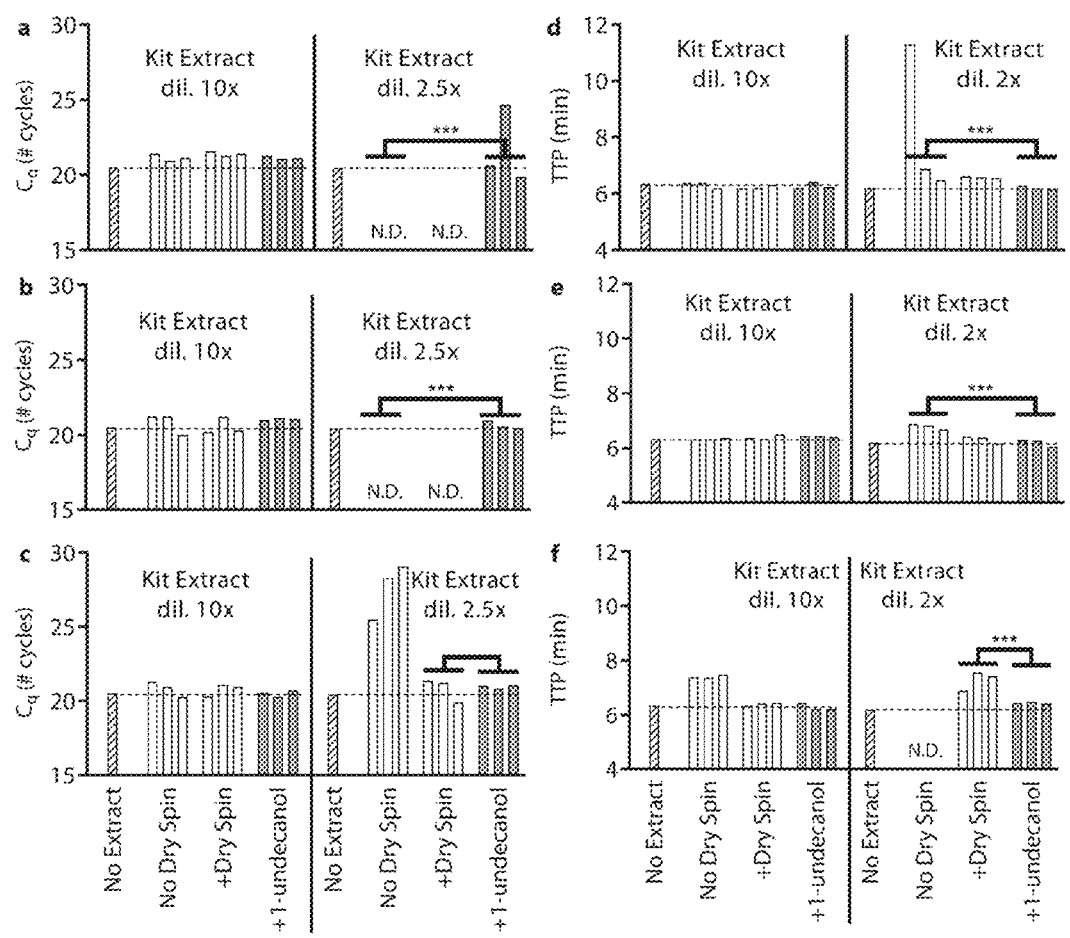
FIG. 6 shows evaluation of TPW for different silica-column NA extraction kit protocols on pure water samples using (Panels a-c) qPCR and (Panels d-f) LAMP. All reactions were spiked with $5\times10^4$ copies λ phage DNA and primers. By manufacturer protocol, the (Panels a,d) Zymo Quick-DNA/RNA Viral Kit and (Panels b,e) Zymo ZR Viral DNA/RNA Kit do not include the dry spin (+dry spin) whereas the (Panels c,f) Qiagen QIAquick PCR Purification Kit does. The left of each graph shows high dilution and the right shows low dilution. Each bar represents the result from a single qPCR or LAMP measurement. 27 silica-column extractions (3 silica columns×3 conditions×3 extraction protocols) were run and the kit extract was shared between high and low dilutions of both qPCR and LAMP. Dashed lines show the Cq or TTP for a reaction without inhibitors ("No Extract"). Samples marked N.D. were not detected within either 40 cycles or 40 min. (Panels a-f) It was shown whether the manufacturer protocol replicates "No Dry Spin for Zymo kits, "+dry spin" for Qiagen kit) fell within the 95% CI of the corresponding +1-undecanol condition for the low kit extract dilution case. The number of replicates that lie outside the 95% CI were indicated by the number of *s.

However, when 2× or 2.5×dilutions was used it was observed significant inhibition (FIG. 6). With the Zymo kits and qPCR, there was no amplification whether or not an additional dry spin was added (FIG. 6 Panels a,b), contradicting Zymo's "no buffer contamination" claim. For the Qiagen kit (FIG. 6 Panel c) and qPCR, the dry spin performs quite well, matching the No Extract control. With the Zymo kits and LAMP (FIG. 6 Panels d,e), there are delays when following the protocol (no dry spin) but this is slightly improved by adding a dry spin. With the Qiagen kit and LAMP (FIG. 6 Panel f), total reaction inhibition was observed without the dry spin and a 1.1 min delay following the manufacturer protocol. In summary, these results prove that inhibitors are carried into the elution, the additional dry step is helpful for removing wash buffers, and high dilution is the responsible for reducing concentrations to non-inhibitory levels.

The present modified protocol was used utilizing 1-undecanol TPW and found substantially improved performance, even at low dilutions of the kit extract. The 95% confidence interval (C.I.) was calculated for each 1-undecanol condition at the low dilution and counted the number of outliers when following the manufacturer protocol. For all kits and combinations, it was found that the TPW matches performance (Qiagen qPCR) or substantially improved performance (Zymo ZR and Zymo Quick qPCR, all LAMP conditions). The most drastic improvement is for the Zymo ZR kit and qPCR, which failed to amplify with the manufacturer protocol but completely recovered when the TPW was added (FIG. 1 Panel c is a subset of FIG. 6 Panel b showing "No Dry Spin" and "+1-undecanol"). Given the dramatic improvements and ease of adding the TPW, it is contemplated that TPW be included in kits of silica-column kit manufacturers.

Figure 16:
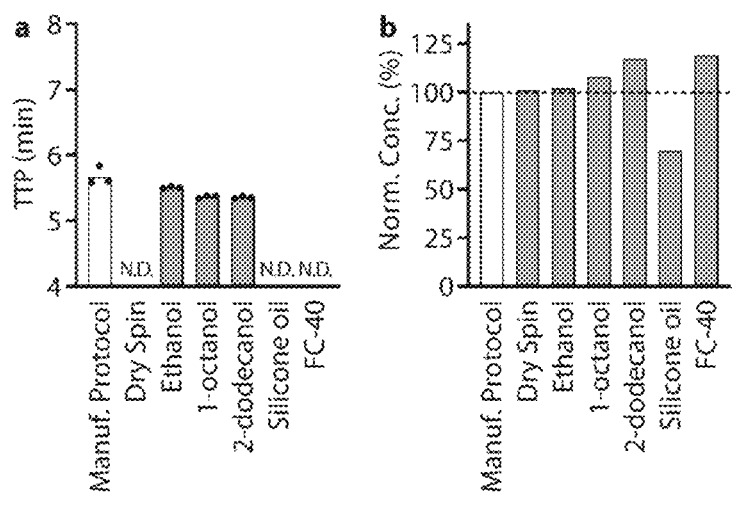
FIG. 16 shows evaluation of TPW as a potential alternative to ethanol-based viral wash buffer in a Zymo ZR kit. (a) LAMP reaction with 2×dilution of eluent and (b) dPCR reaction with 100× dilution of eluent. Bars represent the average of technical LAMP triplicates or merged duplicate dPCR measurements. 7 extractions (1 silica column×7 conditions) were run and same eluent was used LAMP and dPCR reactions. No template controls (n=3) and samples marked N.D. were not detected within 40 min.

It was evaluated whether in some cases the TPW could be considered as an alternative for ethanol-based washes (FIG. 16). As a comparison, the Zymo ZR kit which only has one wash step (viral wash buffer) was used. The viral wash-buffer step was replaced with a dry spin (control), ethanol (control), or different TPW solutions. Briefly, it was found that at least under these clean conditions, ethanol wash slightly outperforms the viral wash buffer, long-chain alcohol washes have the best performance, and non-alcohol washes (silicone oil and fluorocarbon oil) led to failed amplifications.

Example 8: TPW Validation for Magnetic-Bead Extractions

Next it was tested whether TPW would improve magnetic bead extractions. Sur et al. previously found that transferring magnetic particles through a hydrophobic liquid effectively reduced PCR inhibitors [51]. This method, termed immiscible phase filter (IPF), allowed for the replacement of multiple wash steps with a single pass through an immiscible liquid. At a 5×dilution of eluent into RT-qPCR, the IPF method showed no statistical difference in detected copies compared to commercial kits for HIV-1 spiked into plasma, *Chlamydia* and Gonorrhea spiked into urine, and proviral HIV-1 DNA integrated with peripheral blood mononuclear cells in whole blood. Another previous study conducted by Berry et al. described the IFAST (immiscible filtration assisted by surface tension) device [52], and further analyzed their method by examining surface tensions and energies associated with the aqueous phase, immiscible phase, and their device material. The IFAST device reduced total NA extraction operation time to less than 5 min while showing similar performance to commercial extraction kits with operation times between 15 to 45 min (eluent dilution unspecified).

Here with test the TPW with a commercial magnetic bead extraction kit and evaluate both high and low dilution of eluent into LAMP and qPCR. A schematic of the magnetic-bead protocol is shown in FIG. 1 Panel b. Using a Zymo Quick-DNA/RNA MagBead Extraction kit, the experiment started with 1×106 copies λ DNA and eluted with 50 µL. By default, the protocol requires a 10 min air dry step to allow residual ethanol from the wash step to evaporate. The manufacturer protocol, protocol without the air dry step, and the protocol where the air dry step was replaced with a 1-undecanol TPW. At 10× dilution into qPCR (FIG. 7 Panel a) were each tested, omitting the dry step has no effect. Adding the 1-undecanol TPW led to a 1.1 cycle delay, which corresponds to a decrease in NA extraction efficiency (FIG. 7 Panel c) rather than an inhibitory delay. At 10× dilution into LAMP (FIG. 7 Panel b), omitting the air dry step causes a 1 min delay, and including the TPW leads to a 0.7 min TTP improvement. At low dilutions, the inhibitory effects are more drastic, and the TPW clearly outperformed the kit protocol with 2 of 3 manufacturer protocol samples performing worse by qPCR and 3 of 3 manufacturer protocol non-detects.

Figure 17:
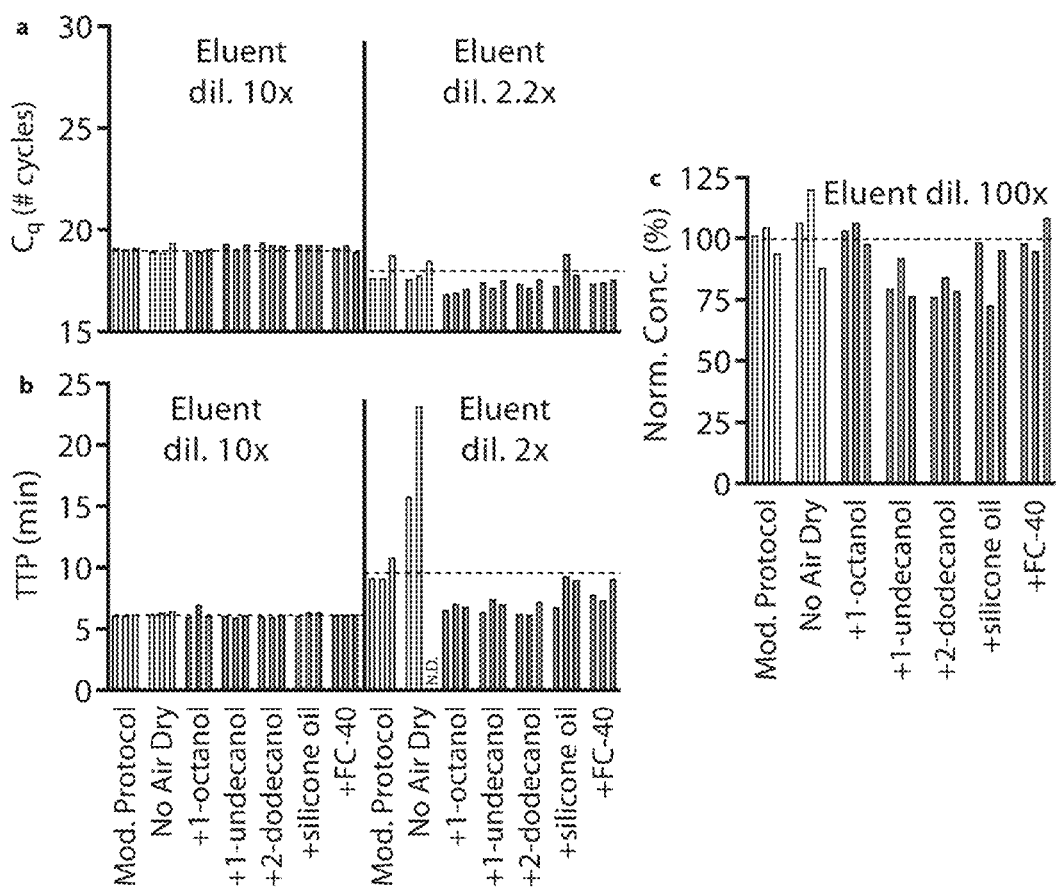
FIG. 17 shows evaluation of a modified Zymo Quick-DNA/RNA Viral MagBead Kit for reduced carryover with and without TPW by (Panel a) qPCR, (Panel b) LAMP, or (Panel c) dPCR. All conditions were performed with a modified protocol for high NA yield when combined with TPW. MagBead extractions were performed on 2.5×10$^6$λ phage DNA copies. Low and high eluent dilutions evaluated by qPCR and LAMP. A 100× eluent dilution into dPCR shows high yield with TPW. Bars represent single qPCR and LAMP reactions or merged duplicate dPCR measurements. 21 extractions (3 magnetic-bead extractions×7 conditions) were run and the same eluent was used in qPCR, LAMP, and dPCR analyses.

Further experimentation with the MagBead kit revealed that the greater the volume of 1-undecanol carryover, the lower NA recovery that was observed. In the experiment shown (FIG. 7), the three extractions had approximately 30 µL, 24 µL, and 22 µL of 1-undecanol carryover as measured by pipette. It was found that following the initial 1-undecanol aspiration, a significant volume of 1-undecanol remains stuck to the magnetic beads and walls of the tube. To improve NA yield, a modified protocol was developed in which the 1-undecanol was aspirated, wait at least 1 min, and any remaining 1-undecanol that slid down the tube due to gravity was aspirated. This modification led to high yield of NAs after TPW for 1-undecanol (FIG. 7 Panel c) and for other compounds (FIG. 17).

The inhibition due to carryover was reduced by developing a TPW protocol that improved eluent purity and led to more efficient and reproducible reactions. It was shown that the inclusion of a dry spin step, although helpful, still generated buffer carryover which inhibited qPCR and LAMP at low eluent dilutions. It was described herein that the inclusion of a TPW step greatly reduced buffer carryover, and It was disclosed herein that low solubility compounds exhibited the best performance. Using the TPW protocol improved eluent purity, leading to more efficient (reduced delays in Cq or TTP) reactions. The addition of the TPW also improved the efficiency of RT reactions.

Figure 7:
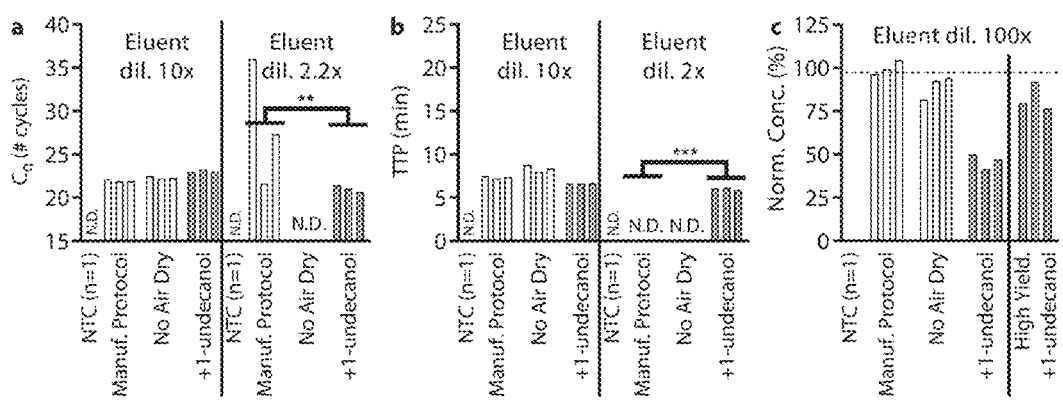
FIG. 7 shows evaluation of TPW for compatibility with Zymo Quick-DNA/RNA MagBead extraction with (Panel a) qPCR, (Panel b) LAMP, and (Panel c) dPCR. Extraction performed on $1\times10^6$ λ phage DNA copies with either a 10 min air dry (Manuf. protocol), no air dry, or with the air dry replaced by a TPW (+1-undecanol) step. The resulting eluent is spiked at either high dilution or low dilution into (Panel a) qPCR and (Panel b) LAMP or 100× dilution into (Panel c) dPCR. For dPCR (Panel c), the bars to the right of the solid black line show the results for an extraction protocol with a +1-undecanol wash using a high-yield protocol from a separate experiment (normalized to the no TPW control in that experiment). Bars represent single qPCR and LAMP or the merged result from a duplicate dPCR measurement. Dashed line in dPCR (Panel c) indicates the average NA recovery following manufacturer protocol. 9 extractions (3 magnetic-bead extractions×3 conditions) were run and the eluent was shared among qPCR, LAMP, and dPCR analyses. Samples marked N.D. were not detected within either 40 cycles for qPCR or 40 min for LAMP. (Panel a-b) It was shown whether the manufacturer protocol replicates fell within the 95% CI of the corresponding+1-undecanol condition for the low eluent dilution case. The number of replicates that lie outside the 95% CI were indicated by the number of *s.

Furthermore, TPW improved reproducibility of amplification reactions by reducing Cq and TTP variations between measurements (FIG. 7 Panel a at 2.2×dilution), and at low target concentrations leading to more repeatable detection (FIG. 7 Panel b, 2×dilution). Reproducibility is an important aspect of nucleic-acid assays in biological research and diagnostic assays. Given the high degree of sensitivity of reactions to levels of carryover (FIG. 2), especially at low target NA concentrations (FIG. 3), it is expected that slight variation in the extent of carryover can lead to high variation in the performance of a NA assay. High purity eluent from TPW was compatible with low dilutions into amplification mix, improving assay sensitivity because more NAs could be added to each reaction.

Example 9: TPW Validation for RT

Figure 8:
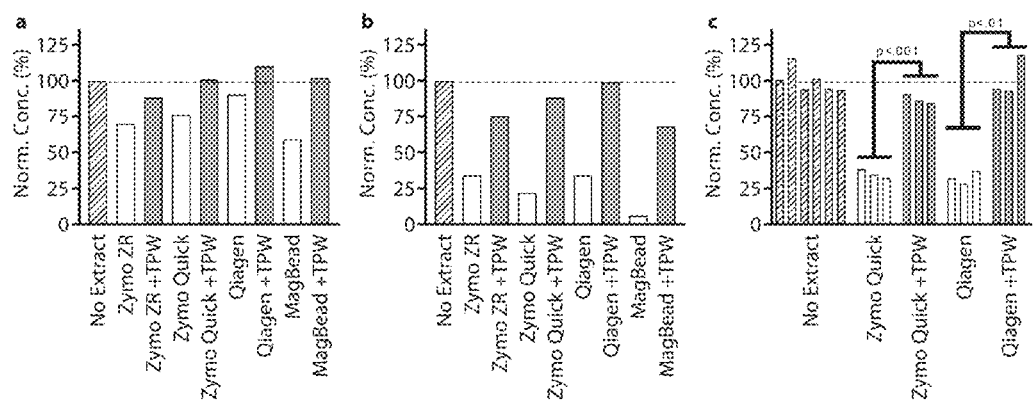
FIG. 8 shows a measurement of reverse transcription (RT) efficiency on *Neisseria gonorrhoeae* RNA using 16S rRNA gene primers with (Panel a) 10× dilution or (Panels b,c) 2× dilution of extractions from different commercial kits into RT reaction mix. NA concentration quantified by digital PCR after 100× dilution of post-transcribed RT mix. (Panel c) it was shown whether RT yield comparing with and without TPW was statistically different using a t-test.
Figure 9:
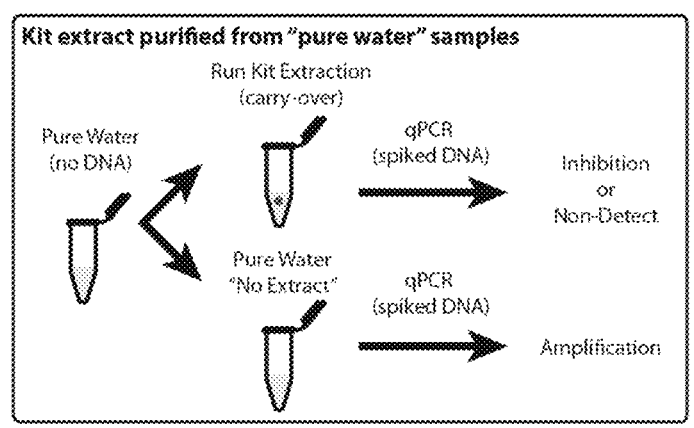
FIG. 9 shows a schematic representation of an exemplary protocol used for experiments performed on "pure water."
Figure 10:
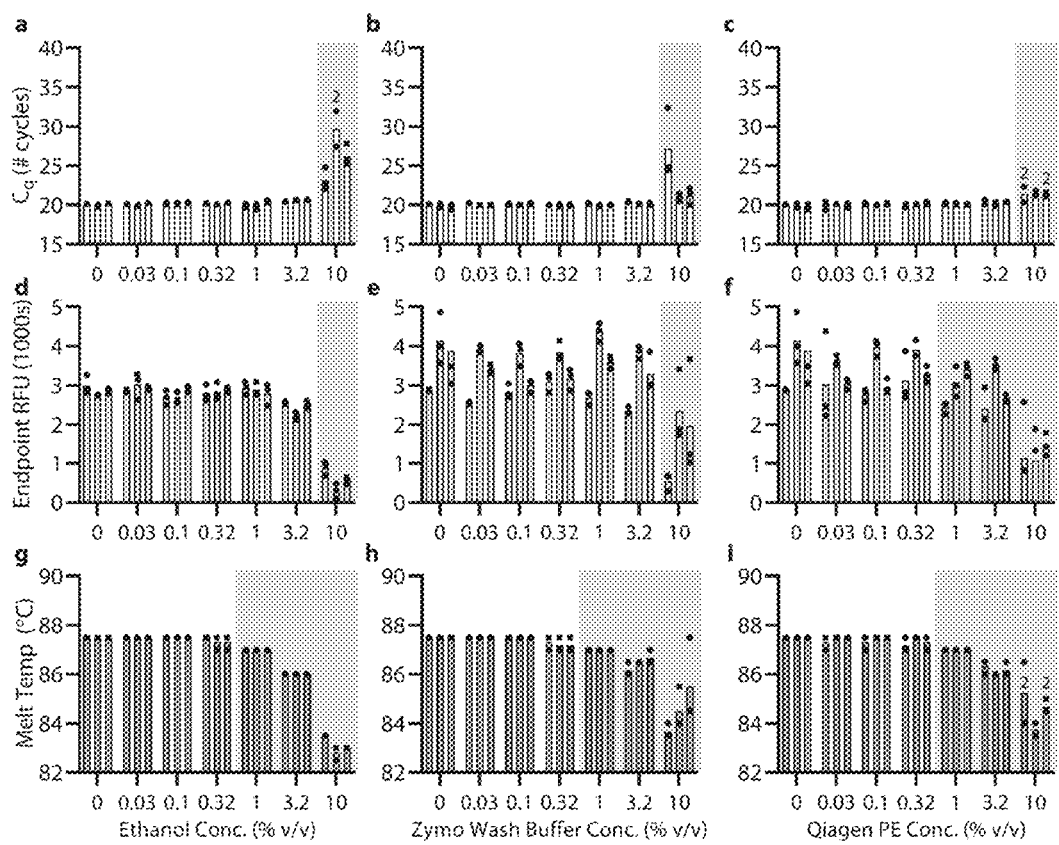
FIG. 10 shows (Panels a-c) Cq, (Panels d-f) endpoint fluorescence, and (Panels g-i) melting temperature for qPCR on 5×10$^4$λ phage DNA copies in the presence of ethanol, Zymo Viral Wash Buffer, or Qiagen PE Buffer. Gray background indicates an average Cq delay of at least 0.5 cycles, RFU decrease of at least 500 RFU, or a melting temperature change of at least 0.5° C. compared with the 0% buffer condition.
Figure 11:
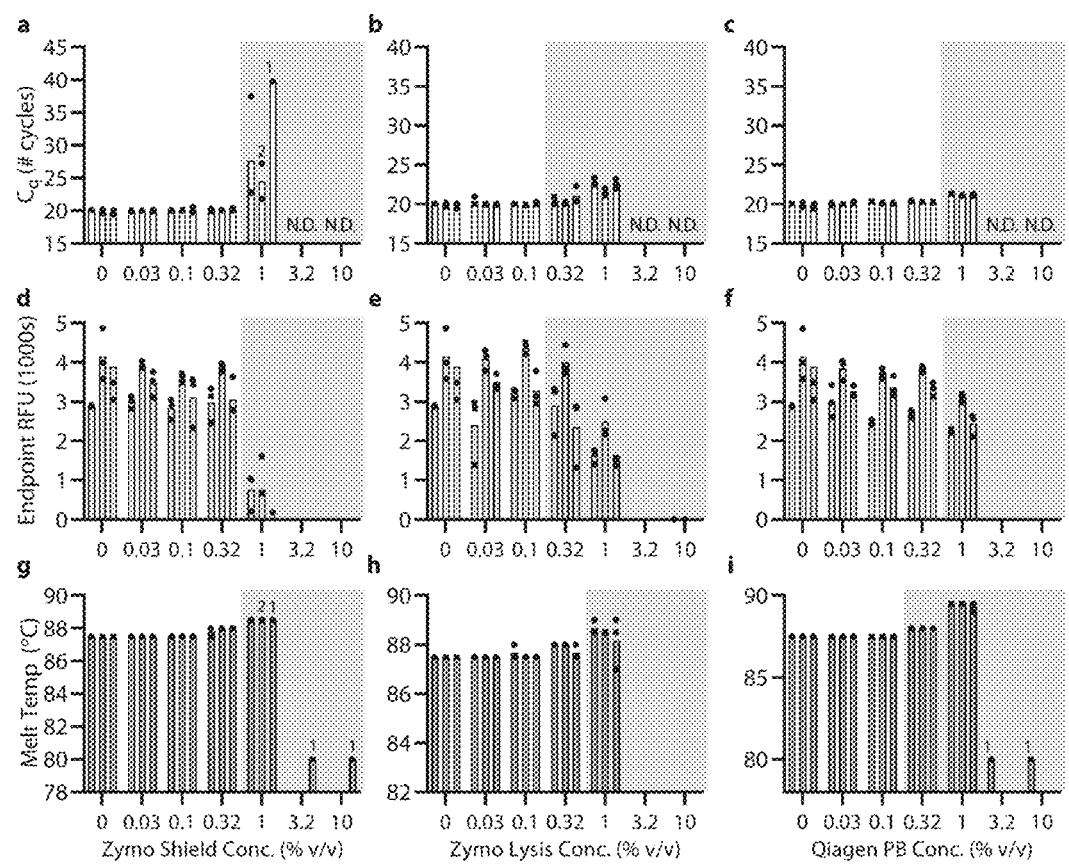
FIG. 11 shows (Panels a-c) Cq, (Panels d-f) endpoint fluorescence, and (Panels g-i) melting temperature for qPCR on 5×10$^4$λ phage DNA copies in the presence of Zymo DNA/RNA Shield, Zymo Viral DNA/RNA Buffer, or Qiagen PB Buffer. Gray background indicates an average Cq delay of at least 0.5 cycles, RFU decrease of at least 500 RFU, or melting temperature change of at least 0.5° C. compared with the 0% buffer condition.
Figure 12:
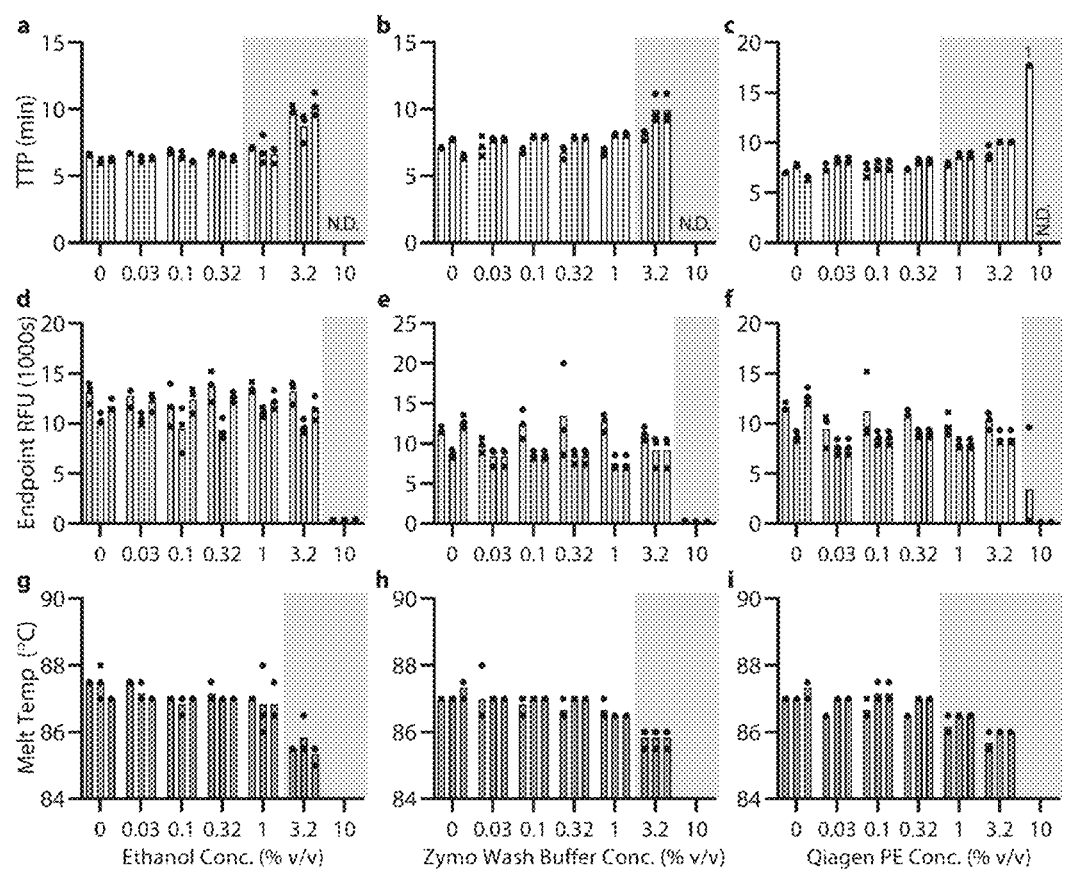
FIG. 12 shows (Panels a-c) TTP, (Panels d-f) endpoint fluorescence, and (Panels g-i) melting temperature for LAMP on 5×10$^4$λ phage DNA copies in the presence of ethanol, Zymo Viral Wash Buffer, or Qiagen PE Buffer. Gray background indicates an average TTP delay of at least 0.5 min, RFU decrease of at least 5000 RFU, or melting temperature change of at least 0.5° C. compared with the 0% buffer condition.
Figure 13:
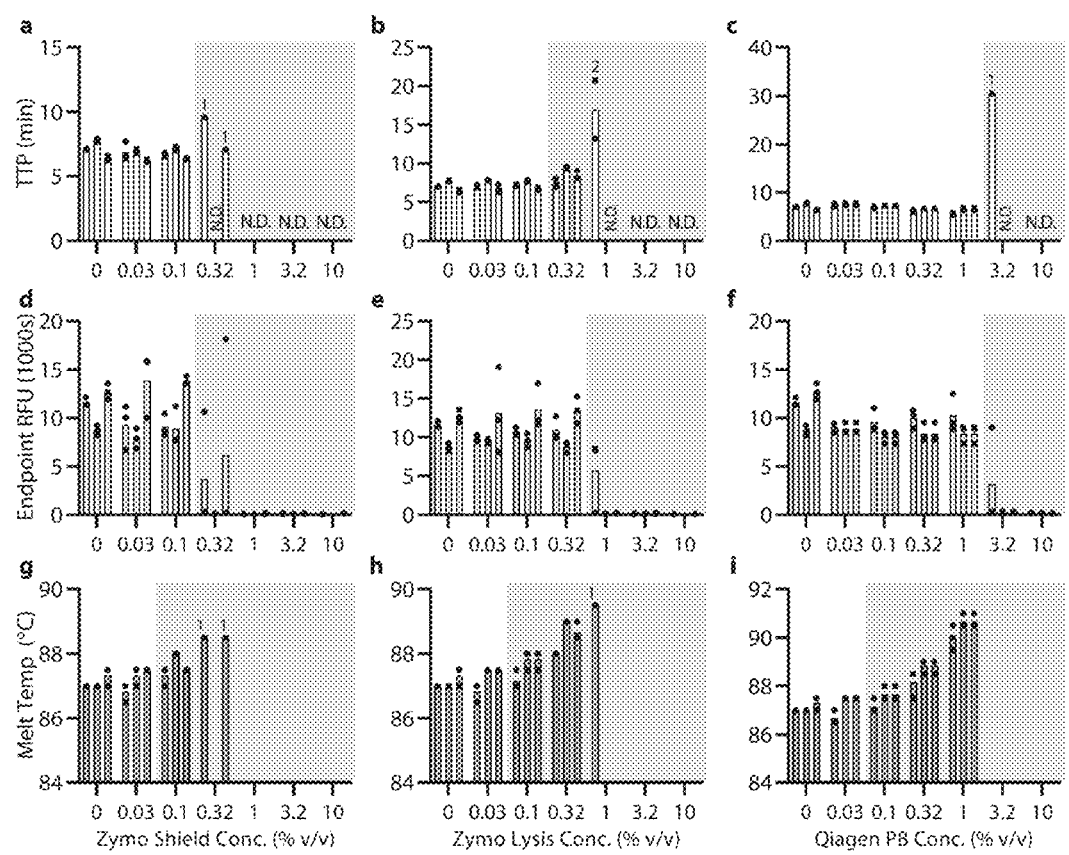
FIG. 13 shows (Panels a-c) TTP, (Panels d-f) endpoint fluorescence, and (Panels g-i) melting temperature for LAMP on 5×10$^4$λ phage DNA copies in the presence of Zymo DNA/RNA Shield, Zymo Viral DNA/RNA Buffer, or Qiagen PB Buffer. Gray background indicates an average TTP delay of at least 0.5 min, RFU decrease of at least 5000 RFU, or melting temperature change of at least 0.5° C. compared with the 0% buffer condition.

Next it was tested how extraction buffer carryover and TPW would affect RT. For applications requiring high sensitivity, the starting sample might only contain a few cells. In these scenarios, it is beneficial to detect RNA because many RNA copies can be made from a single DNA copy. To evaluate whether or not buffer carryover affects RT, an RT experiment was run using RNA from *N. gonorrhoeae*, a pathogen with clinical and diagnostic relevance (FIG. 8). First, a high concentration of RNA was extracted using a Zymo ZR Viral DNA/RNA Kit, and the extracted RNA was diluted 100-fold to reduce the concentration of inhibitors.

Separately, kit extractions was ran on pure water samples for all previously examined NA extraction kits. RNA was combined with kit extractions into RT reactions containing WarmStart Rtx, NG 16S rRNA PCR primers, and other reaction components. It was contemplated that all reactions contained equal concentrations of RNA, and could produce equal levels of DNA. In each RT reaction, either 1 µL kit extract was added to 9 µL reaction mix (10×) or 5 µL kit extract to 5 µL RT reaction mix (2×). For the "No Extract" condition, either 1 µL or 5 µL water was added. Following RT, the transcribed DNA was then diluted an additional 100× and added to dPCR mix (reaction mix, PCR primers) for quantitative analysis. By separating the RT reaction and quantification with dPCR, the effects of buffer inhibition on RT alone can be investigated (whereas with a 1-step RT-dPCR reaction it is difficult to determine whether inhibition affects RT or dPCR).

A clear trend was observed: using kit extracts while following manufacturer protocols led to a reduction in the amount of DNA that was transcribed. This trend was observed even at a 10×dilution of kit extract into the RT reaction, implying that RT is more strongly inhibited than qPCR or LAMP (FIG. 8a). However, when the TPW was added to the NA extraction kit, transcription efficiency was improved for all kits. These trends are even more pronounced when examining a 2×dilution of kit extract into the RT reaction (FIG. 8 Panel b). These results were further confirmed with greater sample size in a separate experiment for 2×dilution of kit extract into RT reaction (FIG. 8 Panel c). It was found that the TPW significantly improved the efficiency of the RT reaction.

Example 10: Kit Extractions on "Pure Water"

Typically, controls were run with nucleic acids (NAs) spiked into the sample prior to the NA extraction step. However, in "pure water" experiments as described herein, the effects of buffer carry-over independently of NA yield were to be evaluated. Subsequently NA extractions were run on "pure water" samples to obtain eluent containing buffer carry-over (kit extract). The original "pure water" sample was used as the non-inhibited control and compared to the kit extract (elution from kit extraction performed on pure water) in NA spiked downstream reactions. This approach was used to generate FIGS. 1c, 6, and 8.

Example 11: Full data set for buffer inhibitors in qPCR and LAMP

FIGS. 10-13 show the full data set for buffer dilutions in qPCR and LAMP. The A-C panels of each figure (providing Cq and TTP data) that were performed in the previous Examples Changes in the endpoint RFU were highly concordant with changes in Cq or TTP. The melting-temperature (Tm) effects showed up at low concentrations of inhibitors, demonstrating that Tm can be an effective indicator for the presence or absence of inhibitors in sample.

Endpoint fluorescence, and melting temperature are measured for qPCR on 5×10$^4$λ phage DNA copies in the presence of ethanol, Zymo Viral Wash Buffer, Zymo DNA/RNA Shield, Zymo Viral DNA/RNA Buffer or Qiagen PE Buffer, or Qiagen PB Buffer.

Example 12: TPW Validation for Different Reaction Mixes with High and Low Dilution TPW was performed in connection with different reactions mixture to verify the related effects in mixture with high and low dilutions.

NEB's SsoFast EvaGreen Supermix was compared to NEB's Luna Universal qPCR master mix and a manually prepared LAMP mix to NEB's pre-made WarmStart LAMP Kit. For the SsoFast mix, 500 nM primers (NEB recommended 300-500 nM) was used and for the Luna mix 250 nM primers (NEB recommendation) was used. The same primer concentration was used for the manually prepared LAMP mix and NEB's pre-made mix. For the LAMP comparison, the lowest possible dilution was 2.86×because NEB's pre-made LAMP mix required 65% of the reaction volume (WarmStart LAMP 2λ master mix, 50×fluorescent dye, primers).

In particular Zymo Quick—DNA/RNA Viral kit, qPCR and LAMP reactions with NEB SsoFast mix NEB Luna mix a manually prepared LAMP and a NEB pre-made LAMP mix were performed according to protocols described in the material and methods section of the present disclosure, on eluent obtained by performing a Zymo Quick-DNA/RNA Viral Kit on 2.5×10$^5$ copies λ phage DNA and eluting with 50 µL water to obtain high dilutions and low dilutions. Six silica-column extractions in total was run and the same kit extract was shared among the high and low dilutions of all assays.

The results are reported in FIG. 14 and in particular in FIG. 14 panel(a) reporting the results of the NEB SsoFast mix, in FIG. 14 panel (b) reporting the results of the NEB Luna mix, in FIG. 14 panel (c) reporting the results of the manually prepared LAMP and in in FIG. 14 panel (d) reporting the results of the NEB pre-made LAMP mix.

The results of FIG. 14, show that at a low dilution of 2.2× or 2.86×, addition of TPW improves NA amplification (see left side of each graph showing high dilution and the right side shows low dilution and samples marked N.D." which indicate not detected within either 40 cycles (qPCR) or 40 min (LAMP).

Therefore, when the TPW was added to the NA extraction kit, transcription efficiency was improved for all kits.

Example 13: Buffer Inhibitors in qPCR and LAMP

It was observed that 3.2% Qiagen PE Buffer in LAMP caused a large delay (6.0 min ΔTTP), but this difference does not measure as statistically significant by t-test. This is due to a bias introduced by a single non-detect (8 out of 9 amplified) which greatly increased the measured standard deviation. If the non-detect from the analysis (rather than assigning the non-detect to a value of 46.7 min) is excluded, the t-test measures a P-value of 0.002. Also Qiagen PB Buffer was shown to have sped up LAMP at low concentrations (0.1%-1%). This result is unexpected, it may be due to primer or reaction mix dependency.

TABLE 1

Summary of ethanol-based buffer dilutions for qPCR

| | Ethanol | | | | | VWB | | | | | PE | | | | |
|---|---|---|---|---|---|---|---|---|---|---|---|---|---|---|---|
| | Avg | Std | ΔCq | p | * | Avg | Std | ΔCq | p | * | Avg | Std | ΔCq | p | * |
| 0% | 20.1 | 0.2 | | | | 20.0 | 0.3 | | | | 20.0 | 0.3 | | | |
| 0.03% | 20.1 | 0.1 | 0.0 | 0.499 | | 20.1 | 0.1 | 0.1 | 0.171 | | 20.0 | 0.3 | 0.0 | 0.431 | |
| 0.1% | 20.2 | 0.1 | 0.1 | 0.065 | | 20.1 | 0.1 | 0.1 | 0.109 | | 20.1 | 0.1 | 0.1 | 0.141 | |
| 0.32% | 20.2 | 0.1 | 0.1 | 0.152 | | 20.0 | 0.1 | 0.0 | 0.449 | | 20.1 | 0.2 | 0.1 | 0.165 | |
| 1% | 20.1 | 0.4 | 0.0 | 0.465 | | 20.1 | 0.1 | 0.1 | 0.302 | | 20.1 | 0.1 | 0.1 | 0.081 | |
| 3.2% | 20.6 | 0.1 | 0.5 | <0.001 | | 20.3 | 0.2 | 0.3 | 0.011 | | 20.3 | 0.2 | 0.3 | 0.006 | |
| 10% | 27.5 | 5.5 | 7.4 | 0.002 | * | 23.2 | 3.8 | 3.2 | 0.019 | * | 25.5 | 8.2 | 5.5 | 0.039 | * |

The average and standard deviation were calculated from 9 replicates. The $\Delta C_q$ is calculated by subtracting the average value for a given buffer concentration from the water condition (0%). A positive value indicates a cycle delay when adding the buffer. P-values were calculated by a 1-tailed unequal variance t-test compared to the water condition (0%). A * indicates a delay of at least 0.5 cycles and P-value<0.05. Non-detects were assigned a value of 40 cycles. VWB=Zymo Viral Wash Buffer; PE=Qiagen PE Buffer.

TABLE 2

Summary of lysis buffer dilutions for qPCR

| | Shield | | | | | Lysis | | | | | PB | | | | |
|---|---|---|---|---|---|---|---|---|---|---|---|---|---|---|---|
| | Avg | Std | ΔCq | p | * | Avg | Std | ΔCq | p | * | Avg | Std | ΔCq | p | * |
| 0% | 20.0 | 0.3 | | | | 20.0 | 0.3 | | | | 20.0 | 0.3 | | | |
| 0.03% | 20.0 | 0.1 | 0.0 | 0.445 | | 20.1 | 0.3 | 0.1 | 0.184 | | 20.1 | 0.2 | 0.1 | 0.101 | |
| 0.1% | 20.1 | 0.2 | 0.1 | 0.126 | | 20.0 | 0.1 | 0.0 | 0.340 | | 20.2 | 0.1 | 0.2 | 0.023 | |
| 0.32% | 20.2 | 0.2 | 0.2 | 0.047 | | 20.5 | 0.7 | 0.5 | 0.029 | * | 20.3 | 0.1 | 0.3 | 0.004 | |
| 1% | 32.4 | 8.5 | 12.4 | 0.001 | * | 22.3 | 0.7 | 2.3 | <0.001 | * | 21.2 | 0.1 | 1.2 | 0.000 | * |
| 3.2% | 40.0 | 0.0 | 20.0 | <0.001 | * | 40.0 | 0.0 | 20.0 | <0.001 | * | 40.0 | 0.0 | 20.0 | 0.000 | * |
| 10% | 40.0 | 0.0 | 20.0 | <0.001 | * | 40.0 | 0.0 | 20.0 | <0.001 | * | 40.0 | 0.0 | 20.0 | 0.000 | * |

The average and standard deviation were calculated from 9 replicates. The $\Delta C_q$ is calculated by subtracting the average value for a given buffer concentration from the water condition (0%). A positive value indicates a cycle delay when adding the buffer. P-values were calculated by a 1-tailed unequal variance t-test compared to the water condition (0%). A * indicates a delay of at least 0.5 cycles and P-value<0.05. Non-detects were assigned a value of 40 cycles. PB=Qiagen PB Buffer.

TABLE 3

Summary of ethanol-based buffer dilutions for LAMP

| | Ethanol | | | | | VWB | | | | | PE | | | | |
|---|---|---|---|---|---|---|---|---|---|---|---|---|---|---|---|
| | Avg | Std | ΔTTP | p | * | Avg | Std | ΔTTP | p | * | Avg | Std | ΔTTP | p | * |
| 0% | 6.3 | 0.2 | | | | 7.1 | 0.6 | | | | 7.1 | 0.6 | | | |
| 0.03% | 6.4 | 0.2 | 0.1 | 0.277 | | 7.2 | 0.7 | 0.1 | 0.420 | | 7.4 | 0.8 | 0.3 | 0.185 | |
| 0.1% | 6.5 | 0.4 | 0.1 | 0.182 | | 7.2 | 0.6 | 0.1 | 0.368 | | 7.2 | 0.8 | 0.1 | 0.380 | |
| 0.32% | 6.6 | 0.2 | 0.2 | 0.022 | | 7.1 | 0.7 | 0.0 | 0.494 | | 7.3 | 0.8 | 0.2 | 0.230 | |
| 1% | 6.9 | 0.6 | 0.5 | 0.019 | * | 7.2 | 0.7 | 0.1 | 0.333 | | 7.8 | 0.8 | 0.7 | 0.021 | * |
| 3.2% | 9.7 | 1.0 | 3.3 | <0.001 | * | 8.6 | 1.2 | 1.5 | 0.003 | * | 13.1 | 12.6 | 6.0 | 0.096 | |
| 10% | 46.7 | 0.0 | 40.3 | <0.001 | * | 46.7 | 0.0 | 39.6 | <0.001 | * | 43.5 | 9.6 | 36.4 | <0.001 | * |

The average and standard deviation were calculated from 9 replicates. The ΔTTP is calculated by subtracting the average value for a given buffer concentration from the water condition (0%). A positive value indicates a cycle delay. P-values were calculated by a 1-tailed unequal variance t-test compared to the water condition (0%). A * indicates a delay of at least 0.5 min and P-value<0.05. Non-detects were assigned a value of 46.7 min. VWB=Zymo Viral Wash Buffer; PE=Qiagen PE Buffer

TABLE 4

Summary of lysis buffer dilutions for LAMP

| | Shield | | | | | Lysis | | | | | PB | | | | |
|---|---|---|---|---|---|---|---|---|---|---|---|---|---|---|---|
| | Avg | Std | ΔTTP | p | * | Avg | Std | ΔTTP | p | * | Avg | Std | ΔTTP | p | * |
| 0% | 7.1 | 0.6 | | | | 7.1 | 0.6 | | | | 7.1 | 0.6 | | | |
| 0.03% | 6.7 | 0.5 | −0.4 | 0.078 | | 7.2 | 0.5 | 0.1 | 0.401 | | 7.0 | 0.8 | −0.1 | 0.338 | |
| 0.1% | 6.8 | 0.4 | −0.3 | 0.095 | | 7.2 | 0.4 | 0.1 | 0.331 | | 6.7 | 0.5 | −0.4 | 0.083 | |
| 0.32% | 38.2 | 16.9 | 31.1 | <0.001 | * | 8.4 | 1.0 | 1.3 | 0.002 | * | 6.3 | 0.5 | −0.8 | 0.005 | |
| 1% | 46.7 | 0.0 | 39.6 | <0.001 | * | 40.1 | 13.2 | 33.0 | <0.001 | * | 6.5 | 0.9 | −0.6 | 0.053 | |
| 3.2% | 46.7 | 0.0 | 39.6 | <0.001 | * | 46.7 | 0.0 | 39.6 | <0.001 | * | 44.9 | 5.4 | 37.8 | <0.001 | * |
| 10% | 46.7 | 0.0 | 39.6 | <0.001 | * | 46.7 | 0.0 | 39.6 | <0.001 | * | 46.7 | 0.0 | 39.6 | <0.001 | * |

The average and standard deviation were calculated from 9 replicates. The ΔTTP is calculated by subtracting the average value for a given buffer concentration from the water condition (0%). A positive value indicates a cycle delay. P-values were calculated by a 1-tailed unequal variance t-test compared to the water condition (0%). A * indicates a delay of at least 0.5 min and P-value<0.05. Non-detects were assigned a value of 46.7 min. PB=Qiagen PB Buffer

Example 14: Buffer Inhibitors in qPCR and LAMP

Example 4 shows qPCR and LAMP experimental details of inhibition in samples with low NA concentrations.

It was observed that qPCR reactions with lysis buffer (FIG. 15 Panel a, dashed lines) had lower amplification efficiency with each cycle compared with reactions lacking lysis buffer (FIG. 15 Panel a, solid lines). This experiment demonstrates that the presence of lysis buffer causes a delay in the Cq and a reduction in the endpoint fluorescence intensity. Meanwhile, LAMP reactions with lysis buffer experienced an initiation delay, but the amplification rate and endpoint fluorescence intensity were not strongly affected (FIG. 15 Panel b).

Example 15: TPW Screen with qPCR and LAMP

TPW candidates are screened with qPCR and LAMP as shown in Table 5 and Table 6 respectively.

TABLE 5

| TPW screen with qPCR | | | | |
|---|---|---|---|---|
| | Avg | Std | ΔCq | N |
| No additive | 20.09 | 0.01 | | 3 |
| Water | 20.03 | 0.02 | −0.06 | 3 |
| Ethanol | 25.30 | 2.03 | 5.21 | 3 |
| Isopropanol | 24.54 | 2.66 | 4.44 | 3 |
| 1-butanol | N.D. | | | 0 |
| Isopentanol | N.D. | | | 0 |
| 1-hexanol | N.D. | | | 0 |
| 1-heptanol | N.D. | | | 0 |
| 1-octanol | 23.63 | 1.10 | 3.54 | 2 |
| 1-nonanol | 20.07 | 0.07 | −0.03 | 3 |
| 1-decanol | 19.80 | 0.10 | −0.29 | 3 |
| 1-undecanol | 19.67 | 0.13 | −0.42 | 3 |
| 2-dodecanol | 19.81 | 0.03 | −0.28 | 3 |
| silicone oil | 19.86 | 0.19 | −0.23 | 3 |
| FC-40 | 20.15 | 0.17 | 0.06 | 3 |

ΔCq calculated by subtracting the "No additive" control from each condition.

Table 5 shows results of qPCR experiment for selecting target compound removing agents. As ΔCq calculated by subtracting the "No additive" control from each condition for each agent shows, 1-decanol, 2-dodecanol, 2-dodecanol each has a ΔCq of −0.29, −0.42 and −0.28, represent the most reduction in the quantification cycles, corresponding to least inhibition by the buffer. In contrast, 1-octanol has a ΔCq of 3.54, indicating inhibition due to poor separation of the buffer.

TABLE 6

| TPW screen with LAMP | | | | |
|---|---|---|---|---|
| | Avg | Std | ΔTTP | N |
| No additive | 6.54 | 0.05 | | 3 |
| water | 7.09 | 0.05 | 0.55 | 3 |
| Ethanol | N.D. | | | 0 |
| Isopropanol | N.D. | | | 0 |
| 1-butanol | N.D. | | | 0 |
| isopentanol | N.D. | | | 0 |
| 1-hexanol | N.D. | | | 0 |
| 1-heptanol | N.D. | | | 0 |
| 1-octanol | 11.18 | 2.44 | 4.63 | 3 |
| 1-nonanol | 7.41 | 0.06 | 0.87 | 3 |
| 1-decanol | 7.06 | 0.03 | 0.51 | 3 |
| 1-undecanol | 6.70 | 0.03 | 0.16 | 3 |
| 2-dodecanol | 6.43 | 0.05 | −0.11 | 3 |
| silicone oil | 6.49 | 0.02 | −0.06 | 3 |
| FC-40 | 6.64 | 0.04 | 0.09 | 3 |

ΔTTP calculated by subtracting the "No additive" control from each condition.

Table 6 shows results of LAMP experiment for selecting target compound removing agents. Change in time to positive (TTP) ΔTTP for 1-nonanol, 1-decanol 1-undecanol, 2-dodecanol are 0.87, 0.51, 0.16, −0.11, all of which are unexpected much smaller than 4.63 for 1-octanol, demonstrating surprisingly better removal of the inhibitors.

Example 16: Solubility Table and Ethanol Phase Separation for TPW Candidates

It is contemplated that solubility of the target compound removing agent in water and the water solubility in the target compound removing agent are elements to consider in the suitability of the candidates. Subsequently, Table 7 is constructed to provide a list of organic compounds to be evaluated as initial candidates for TPW. It is unexpectedly found that a target compound having a water solubility equal to or greater than 0.05 g per 100 mL at 25° C. at 1 atm pressure with water having a solubility in the removing agent of less than 10 g per 100 mL at 25° C. at 1 atm pressure allows removing up to 99.999% of the target compound from the solid matrix while retaining up to 99.99% of the nucleic acid.

TABLE 7

Solubility table for two-phase wash (TPW) candidates

| Candidate TPW | Solubility of TPW Candidate in water | Solubility of water in TPW Candidate |
|---|---|---|
| FC-40[53] | <0.0050% | <0.0007 g/100 g |
| Silicone oil[54] | Practically insoluble | 0.01-0.02 g/100 g |
| 2-dodecanol[55] | Unknown | Unknown |
| 1-dodecanol[55] | 0.0004 g/100 g | 3.0 g/100 g |
| 1-undecanol[56] | 0.0015 g/100 mL | 3.4 g/100 g |
| 1-decanol[55] | 0.0037 g/100 g | 3.6 g/100 g |
| 1-nonanol[55] | 0.014 g/100 g | 4.0 g/100 g |
| 1-octanol[55] | 0.054 g/100 g | 4.6 g/100 g |
| 1-heptanol[55] | 0.174 g/100 g | 5.4 g/100 g |
| 1-hexanol[55] | 0.6 g/100 g | 7.0 g/100 g |
| Isopentanol[55] | 2.7 g/100 g | 9.8 g/100 g |
| 1-butanol[55] | 7.4 g/100 g | 20.3 g/100 g |
| Isopropanol | Miscible | Miscible |
| Ethanol | Miscible | Miscible |

TABLE 8

Compounds were mixed at a 1:1 volume ratio.

| | H₂O | Ethanol | VWB |
|---|---|---|---|
| FC-40 | 2 | 2 | 2 |
| Silicone oil | 2 | 2 | 2 |
| 2-dodecanol | 2 | 1 | 1 |
| 1-undecanol | 2 | 1 | 1 |
| 1-octanol | 2 | 1 | 1 |

A "2" denotes phase separation into 2 distinct phases whereas a "1" forms a single phase. VWB stands for Zymo Viral Wash Buffer, which contained 80% ethanol (v/v).

The TPW in Table 8 separates to either the top phase or the bottom phase (density dependent) while interacting minimally with the aqueous solution. As a result of reduced interactions with the aqueous solution, the TPW is less toxic to downstream reactions. In LAMP reactions with added alcohols (FIG. 4 Panel b), it was also noticed that the TTP delay decreased as the solubility decreased (from 1-octanol to 2-dodecanol). The 1-octanol had the greatest delay (without completely inhibiting the reaction). Although 1-octanol mostly occupied its own phase, some 1-octanol dissolved in the aqueous phase and may disrupt polymerase activity. Furthermore, it was also noticed that the TTP for the very low solubility TPWs matched the "No Additive" condition rather than the "Water" condition, implying the reaction mix was not diluted by the 1 μL of added TPW.

Example 17: Evaluating a 3-Step Centrifugation Extraction with TPW

To determine whether in some cases the TPW could be considered as an alternative to the ethanol wash for removing lysis buffer, evaluation of a 3-step centrifugation extraction with TPW was made. Exchanging the ethanol wash for a TPW could be useful for applications in which the starting sample is already relatively pure. For this experiment, Zymo ZR kit was used, which has three centrifugation steps: lysis (sample, shield, lysis buffer), wash (ethanol-based viral wash buffer), and elution (water). Either following the manufacturer protocol or replacing the viral wash buffer with a dry spin, ethanol, or TPW (FIG. 16) was performed. An aliquot of 5 μL of the resulting eluent was added to 5 μL of LAMP reaction mix and amplified at 68° C. Eluent from the manufacturer protocol amplified in 5.7 min. The dry spin did not amplify, which is expected because lysis buffer was not removed by any wash steps and lysis buffer is very inhibitory for LAMP. A 100% ethanol wash performed slightly better (earlier TTP) than the viral wash buffer and both 1-octanol and 2-dodecanol outperformed the wash buffer. Meanwhile, eluent from the silicone oil and FC-40 wash conditions did not amplify. A dPCR experiment on heavy dilutions of the eluent show similar recovery for all conditions, with a slight reduction for the silicone oil wash. This demonstrates that 1-octanol and 2-dodecanol remove lysis buffer from the column. The simplicity of a 3-step protocol (bind, wash, elute) is compatible with point-of-care devices (few steps), and could be useful for applications with relatively clean samples.

Also, the illustration of FIG. 4, in combination with the other data, suggest that while 1-octanol is more effective than conventional washes, it is also slightly inhibitory to PCR and LAMP, whereas dodecanol is not.

Accordingly, the results shown in FIG. 4 support the conclusions that a target compound removing agent having a water solubility equal to or less than 0.05 g per 100 mL at 25° C. at 1 atm pressure, preferably equal to or less than 0.03 g per 100 mL at 25° C. at 1 atm pressure with water having a solubility in the removing agent of less than 10 g per 100 mL at 25° C. at 1 atm pressure is particularly advantageous in removing target compounds since they are effective in removing target compounds, while minimizing the loss of nucleic acid during the target compound removal, and, in view of their solubility, such target compound removing agents have little to no inhibitory activity on biochemical reactions in particular, on qPCR, LAMP and dPCR as will be understood by a skilled person.

In particular, TPW of 2-dodecanol used in the present example allows removal of at least 80%, 90%, 95%, 97%, 99%, 99.5%, 99.99%, or 99.999% of one or more of the inhibitors in the buffer carryover from the solid matrix while retaining at least 10%, 20%, 30%, 50%, 75%, 90%, 95%, 98%, 99%, 99.5%, 99.8%, 99.9%, or 99.99% of the nucleic acid. With the effective removal of inhibitor in buffer carryover and sufficient retainment of nucleic acid, 2-dodecanol as an additional wash buffer prior to the elution step allows high sensitivity application (e.g., single-cell sequencing, cell-free circulating DNA, SNP genotyping, and diagnostics), amplification reactions to be run at or near the limit-of-detection (LOD).

Example 18: Evaluating a Low-Carryover, High-Yield MagBead Protocol

A commercially available kit was used in experiments performed to provide an improved protocol for NA separation over any presently existing methods and to achieve a low-carryover, high-yield separation using TPW incorporated into MagBead protocol.

The manufacturer protocol for the Zymo Quick-DNA/ RNA Viral MagBead Kit led to significant extraction buffer carryover (as shown in FIGS. 7-8). To improve NA yield with the added TPW, an initial TPW aspiration was performed, waited at least 1 min, and aspirated any remaining TPW. This second aspiration collected a few microliters of residual buffer that dripped down from the walls of the tube or from the magnetic beads. To reduce carryover of all buffers, this 1 min wait was applied and secondary aspiration to all steps (lysis/binding buffer, wash buffers). This modified protocol for different TPWs was evaluated and the results are shown in FIG. 17. At high dilutions of eluent, there were no visible indicators of inhibition for any of the samples. The modified protocol greatly reduced carryover overall, such that qPCR began to work even at low dilutions (whereas when run using the standard manufacturer protocol inhibition was observed). The addition of the TPW further improved LAMP at low dilutions. Finally, NA recovery improved to 75-100%, achieving an objective of the present disclosure.

Example 19: Expected Effectiveness of TPW for Mixture with Low Concentrations NA in view of the exemplary and representative target compound removing agents shown in Example 17 and in FIG. 4, target compounds removing agents according to the present disclosure are expected to be effective in separation of mixtures where nucleic acid are comprised at a low copy number In particular et compounds removing agents according to the present disclosure expected to be effective in embodiment where following contacting with a mixture, a matrix such as the silica matrix of FIG. 4 comprises between 1-1E7 (1 to 1×107) copies on the solid matrix.

In those occurrences, TPW in the sense of the disclosure is expected to outperform the traditional workflow when operating near the limit-of-detection of a biochemical reaction to be performed downstream the nucleic acid separation e.g. within 1 ×10×, 100×, 1000×, etc. of the limit-of-detection) in various scenarios.

For example in a first scenario in a sample comprising 10 copies NA an elution with 30 uL (0.3 copy/µL) and addition of 10 uL to PCR or LAMP (3 copies total) will expected to be effective. If the limit-of-detection is 1 copy/reaction this is 3× the limit-of-detection.

In a second scenario in a sample comprising 1000 copies, an elution with 50 µL (20 copy/µL) and addition of 1 µL to PCR or LAMP (20 copies total) is expected to be effective. If the limit of detection is 10 copies/reaction, this is 2× the limit-of-detection.

In a third scenario in a sample comprising 1E6 copies an elution with 100 uL (1E4 copy/uL) and addition of 1 uL to a LAMP reaction (1E4 copies total).is expected to be effective If the LAMP limit-of-detection is 1000 copies this is 10× the limit-of-detection.

Additional scenarios are identifiable by a skilled person upon reading of the present disclosure.

Example 20: Exemplary Procedure to Determine Copy Number in a Silica Matrix

The following procedure can be performed to determine the copy number of a nucleic acid in a silica matrix following contacting of the matrix with a
(1) Elute the silica matrix with 50 µL elution buffer (e.g. water, TE buffer, TE+ buffer),
(2) Add 1 µL eluent to a 10 µL qPCR or dPCR reaction,
(3) Use previously generated standard curve to calculate the concentration (copies/µL),
(4) Back-calculate to get to the copy number bound to the silica matrix.

Example 21: General Protocol of Using TPW Kits

A general TPW Kit Protocol can comprise the following steps.
(1) Start with 1 µL-100 mL of sample
(2) Dilute the sample by 1×, 10×, 100×, or more,
(3) Mix lysis buffer with sample at a ratio of 1:1-5:1
(4) Add 25 µL-1 mL lysed sample to the solid matrix, centrifuge
(5) Repeat above step until all lysed sample is used.
(6) Wash the solid matrix with 25 µL-1 L wash buffer, centrifuge
(7) Repeat step #5 between 1-2 times
(8) (If using TPW) wash the solid matrix with 25 µL-1 L two-phase wash, centrifuge,
(9) Elute the solid matrix with 1-200 µL eluent, centrifuge
(10) Dilute the eluent 1×-100×into downstream analysis (e.g. qPCR, dPCR or LAMP).

Example 22: Exemplary Standard TPW Kit Protocol

An exemplary TPW Kit standard Protocol can comprise the following steps.
(1) Start with 125 µL sample
(2) No dilution of sample (1×)
(3) Add 500 µL lysis buffer (4:1 ratio)
(4) Add 625 µL lysed sample to column, centrifuge,
(5) Repeat above step until all lysed sample is used.
(6) Add 750 µL wash buffer, centrifuge
(7) Do not repeat
(8) Add 750 µL TPW buffer, centrifuge
(9) Elute with 50 µL eluent, centrifuge
(10) Dilute the eluent 10× (1 µL in a 10 µL reaction) into qPCR, dPCR or LAMP.

Example 23: Exemplary TPW Kit Protocol for Low NA Concentration

A representative TPW Kit Protocol for low DNA concentration can comprise the following steps.
(1) Start with 5 mL sample
(2) No dilution of sample (1×)
(3) Add 5 mL lysis buffer (1:1 ratio)
(4) Add 2 mL lysed sample to column, centrifuge
(5) Repeat above step 5×
(6) Add 1 mL wash buffer, centrifuge
(7) Repeat step #6 1×
(8) Add 1 mL TPW buffer, centrifuge
(9) Elute with 10 µL eluent, centrifuge
(10) Dilute the eluent 2×(5 µL in a 10 µL reaction) into qPCR, dPCR or LAMP.

Example 24: Exemplary TPW Kit Protocol for a Small Volume Example for Use in Centrifugal Microfluidics An exemplary TPW Kit Protocol for a small volume example for use in centrifugal microfluidics can comprise the following steps.
(1) Start with 1 uL sample
(2) Dilute the sample with buffer (e.g. water or PBS) to 10 uL total volume
(3) Add 10 uL lysis buffer (1:1 ratio)
(4) Add 20 uL lysed sample to column, centrifuge
(5) No repeats
(6) Add 50 uL wash buffer, centrifuge
(7) No repeats
(8). Add 50 uL TPW buffer, centrifuge
(9). Elute with 5 uL eluent, centrifuge
(10). Resuspend eluent with dry lyophilized PCR or LAMP mix (1× or no dilution)

Example 25: Protocol of using TPW Kits by tracking the number of copies

An exemplary general TPW Kit Protocol for tracking the number of NA copies can comprise the following steps for an exemplary Starting sample containing 1-1E12 total copies, Concentration: 1 copy/µL to 1E7 copies/µL and Starting volumes: 1 µL to 1E5 µL
(1) Mix with lysis buffer at desired dilution ratio
(2) Add all lysed sample to the column. Ideally 100% binding efficiency, expect 70-90%, possibly>50%, >10%, >1%. Total copies bound to the column: 1-1E12 copies
(3) Perform elution, for example elution with 50 uL
(4) Eluent concentration is 0.02 copies/µL to 2E10 copies/uL.
(5) Add 50 uL eluent into a 100 µL reaction (2×dilution)
(6) Total copies in the reaction: 1 copy to 1E12 copies total.

In examples of the present disclosure, when inhibitors are a major concern and time is not an issue, the MagBead protocol with secondary aspirations on each step was performed, adding a 10-min dry step, and adding the TPW. For an approach balancing performance and assay time, following the manufacturer protocol, replacing the 10-min dry step with the TPW, and adding a secondary aspiration step just prior to the elution was performed.

TPW used in the present example allows removal of at least 80%, 90%, 95%, 97%, 99%, 99.5%, 99.99%, or 99.999% of one or more of the inhibitors in the buffer carryover from the solid matrix while retaining at least 10%, 20%, 30%, 50%, 75%, 90%, 95%, 98%, 99%, 99.5%, 99.8%, 99.9%, or 99.99% of the nucleic acid. With the effective removal of inhibitor in buffer carryover and sufficient retainment of nucleic acid, TPW as an additional wash buffer prior to the elution step allows high sensitivity application (e.g., single-cell sequencing, cell-free circulating DNA, SNP genotyping, and diagnostics), amplification reactions to be run at or near the limit-of-detection (LOD).

In summary, described herein are Methods and systems and related composition for separating through a solid matrix a mixture comprising a nucleic acid together with a target compounds having a water solubility equal to or greater than 0.001 g per 100 mL, which can be used for managing fluid flow, biochemical reactions and purification of nucleic acids or other target analytes.

In particular, in several embodiments, the methods include solid-phase extraction of analytes such as nucleic acids having a step of washing of a solid matrix such as silica column with a removing agent and related detection reagents, compositions, methods and systems.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified methods and systems based on the target compound removing agents, nucleic acid removing agents, solid matrices, and devices according to various embodiments and scope of the claims.

All patents and publications mentioned in the specification are indicative of the levels of skill of those skilled in the art to which the disclosure pertains.

The entire disclosure of each document cited (including webpages patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1 SR, K. PCR Technique with its Application. *Research & Reviews: Journal of Microbiology and Biotechnology* 4, 1-12 (2015).
2 Valones, M. A. et al. Principles and applications of polymerase chain reaction in medical diagnostic fields: a review. *Braz. J. Microbiol.* 40, 1-11, doi:10.1590/s1517-83822009000100001 (2009).
3 Day, E., Dear, P. H. & McCaughan, F. Digital PCR strategies in the development and analysis of molecular biomarkers for personalized medicine. *Methods* 59, 101-107 (2013).
4 Gielis, E. M. et al. Cell-Free DNA: An Upcoming Biomarker in Transplantation. *Am. J. Transplant.* 15, 2541-2551, doi:10.1111/ajt.13387 (2015).
5 Klein, D. Quantification using real-time PCR technology: applications and limitations. *Trends Mol. Med.* 8, 257-260 (2002).
6 Craw, P. & Balachandran, W. Isothermal nucleic acid amplification technologies for point-of-care diagnostics: a critical review. *Lab on a chip* 12, 2469-2486, doi:10.1039/c2lc40100b (2012).
7 Notomi, T. et al. Loop-mediated isothermal amplification of DNA. *Nucleic Acids Res.* 28, E63, doi:10.1093/nar/28.12.e63 (2000).
8 Tanner, N. A. & Evans, T. C., Jr. Loop-mediated isothermal amplification for detection of nucleic acids. *Curr. Protoc. Mol. Biol.* 105, Unit 15.14., doi:10.1002/0471142727.mb1514s105 (2014).
9 Yager, P., Domingo, G. J. & Gerdes, J. Point-of-care diagnostics for global health. *Annu. Rev. Biomed. Eng.* 10, 107-144, doi:10.1146/annurev.bioeng.10.061807.160524 (2008).
10 Boesenberg-Smith, K. A., Pessarakli, M. M. & Wolk, D. M. Assessment of DNA yield and purity: an overlooked detail of PCR troubleshooting. *Clin. Microbiol. Newsl.* 34, 1-6 (2012).
11 Huggett, J. F. et al. Differential susceptibility of PCR reactions to inhibitors: an important and unrecognised phenomenon. *BMC Res. Notes* 1, 70, doi:10.1186/1756-0500-1-70 (2008).
12 Kaneko, H., Kawana, T., Fukushima, E. & Suzutani, T. Tolerance of loop-mediated isothermal amplification to a culture medium and biological substances. *J. Biochem. Biophys. Methods* 70, 499-501, doi:10.1016/j.jbbm.2006.08.008 (2007).
13 Bustin, S. A., Benes, V., Nolan, T. & Pfaffl, M. W. Quantitative real-time RT-PCR—a perspective. *J. Mol. Endocrinol.* 34, 597-601, doi:10.1677/jme.1.01755 (2005).
14 Tebbe, C. C. & Vahjen, W. Interference of humic acids and DNA extracted directly from soil in detection and transformation of recombinant DNA from bacteria and a yeast. *Appl. Environ. Microbiol.* 59, 2657-2665 (1993).
15 Simbolo, M. et al. DNA qualification workflow for next generation sequencing of histopathological samples. *PLoS One* 8, e62692, doi:10.1371/journal.pone.0062692 (2013).
16 Rossen, L., Norskov, P., Holmstrom, K. & Rasmussen, O. F. Inhibition of PCR by components of food samples, microbial diagnostic assays and DNA-extraction solutions. *Int. J. Food Microbiol.* 17, 37-45, doi:10.1016/0168-1605(92)$_{90017}$-w (1992).
17 Wilson, I. G. Inhibition and facilitation of nucleic acid amplification. *Appl. Environ. Microbiol.* 63, 3741 (1997).
18 Nolan, T., Hands, R. E., Ogunkolade, W. & Bustin, S. A. SPUD: a quantitative PCR assay for the detection of inhibitors in nucleic acid preparations. *Anal. Biochem.* 351, 308-310, doi:10.1016/j.ab.2006.01.051 (2006).
19 Schrader, C., Schielke, A., Ellerbroek, L. & Johne, R. PCR inhibitors-occurrence, properties and removal. *J. Appl. Microbiol.* 113, 1014-1026, doi:10.1111/j.1365-2672.2012.05384.x (2012).

20 Alaeddini, R. Forensic implications of PCR inhibition—A review. *Forensic science international: Genetics* 6, 297-305, doi:10.1016/j.fsigen.2011.08.006 (2012).

21 Hu, Q., Liu, Y., Yi, S. & Huang, D. A comparison of four methods for PCR inhibitor removal. *Forensic science international: Genetics* 16, 94-97, doi:10.1016/j.fsigen.2014.12.001 (2015).

22 Radstrom, P., Lofstrom, C., Lovenklev, M., Knutsson, R. & Wolffs, P. Strategies for overcoming PCR inhibition. *CSH protocols* 2008, pdb.top20, doi:10.1101/pdb.top20 (2008).

23 Opel, K. L., Chung, D. & McCord, B. R. A study of PCR inhibition mechanisms using real time PCR. *J. Forensic Sci.* 55, 25-33, doi:10.1111/j.1556-4029.2009.01245.x (2010).

24 Mahony, J. et al. Urine specimens from pregnant and nonpregnant women inhibitory to amplification of *Chlamydia trachomatis* nucleic acid by PCR, ligase chain reaction, and transcription-mediated amplification: identification of urinary substances associated with inhibition and removal of inhibitory activity. *J. Clin. Microbiol.* 36, 3122-3126 (1998).

25 Demeke, T. & Jenkins, G. R. Influence of DNA extraction methods, PCR inhibitors and quantification methods on real-time PCR assay of biotechnology-derived traits. *Anal. Bioanal. Chem.* 396, 1977-1990, doi:10.1007/s00216-009-3150-9 (2010).

26 Chacon-Cortes, D. & Griffiths, L. R. Methods for extracting genomic DNA from whole blood samples: current perspectives. *Journal of Biorepository Science for Applied Medicine* 2014, 1-9 (2014).

27 Abd El-Aal, A. A., Abd Elghany, N. A., Mohamadin, A. M. & El-Badry, A. A. Comparative study of five methods for DNA extraction from whole blood samples. *International Journal of Health Science* 3 (2010).

28 Price, C. W., Leslie, D. C. & Landers, J. P. Nucleic acid extraction techniques and application to the microchip. *Lab on a chip* 9, 2484-2494, doi:10.1039/b907652m (2009).

29 Bergallo, M. et al. Evaluation of six methods for extraction and purification of viral DNA from urine and serum samples. *The new microbiologica* 29, 111-119 (2006).

30 Ali, N., Rampazzo, R. C. P., Costa, A. D. T. & Krieger, M. A. Current Nucleic Acid Extraction Methods and Their Implications to Point-of-Care Diagnostics. *BioMed research international* 2017, 9306564, doi:10.1155/2017/9306564 (2017).

31 Priye, A. et al. A smartphone-based diagnostic platform for rapid detection of Zika, chikungunya, and dengue viruses. *Sci. Rep.* 7, 44778, doi:10.1038/srep44778 (2017).

32 Goldberg, C. S., Sepulveda, A., Ray, A., Baumgardt, J. & Waits, L. P. Environmental DNA as a new method for early detection of New Zealand mudsnails (*Potamopyrgus antipodarum*). *Freshwater Science* 32, 792-800 (2013).

33 Rudi, K., Hagen, I., Johnsrud, B. C., Skjefstad, G. & Tryland, I. Different length (DL) qPCR for quantification of cell killing by UV-induced DNA damage. *Int. J. Env. Res. Public Health* 7, 3376-3381, doi:10.3390/ijerph7093376 (2010).

34 Qiu, J., Chen, P. & Lin, S. Development of a Real-Time Polymerase Chain Reaction Method to Measure Ligation Efficiency. *Journal of Experimental Microbiology and Immunology* (2015).

35 Mason, W. J. et al. Multiplex PCR protocol for the diagnosis of staphylococcal infection. *J. Clin. Microbiol.* 39, 3332-3338, doi:10.1128/jcm.39.9.3332-3338.2001 (2001).

36 Kamau, E., Alemayehu, S., Feghali, K. C., Saunders, D. & Ockenhouse, C. F. Multiplex qPCR for detection and absolute quantification of malaria. *PLoS One* 8, e71539, doi:10.1371/journal.pone.0071539 (2013).

37 Crotchfelt, K. A., Welsh, L. E., DeBonville, D., Rosenstraus, M. & Quinn, T. C. Detection of *Neisseria gonorrhoeae* and *Chlamydia trachomatis* in genitourinary specimens from men and women by a coamplification PCR assay. *J. Clin. Microbiol.* 35, 1536-1540 (1997).

38 Biava, M. et al. Evaluation of a rapid and sensitive RT-qPCR assay for the detection of Ebola Virus. *J. Virol. Methods* 252, 70-74, doi:10.1016/j.jviromet.2017.11.009 (2018).

39 Peist, R., Honsel, D., Twieling, G. & Löffert, D. PCR inhibitors in plant DNA preparations. *Qiagen news* 3, 7-9 (2001).

40 Nixon, G. et al. Comparative study of sensitivity, linearity, and resistance to inhibition of digital and nondigital polymerase chain reaction and loop mediated isothermal amplification assays for quantification of human cytomegalovirus. *Anal. Chem.* 86, 4387-4394, doi:10.1021/ac500208w (2014).

41 Jue, E., Witters, D. & Ismagilov, R. F. How to diagnose and solve the ubiquitous contaminant-carryover problem in commercial nucleic acid extraction kits. *PittCon* 2020, Oral Presentation.

42 Goto, M., Honda, E., Ogura, A., Nomoto, A. & Hanaki, K. Colorimetric detection of loop-mediated isothermal amplification reaction by using hydroxy naphthol blue. *BioTechniques* 46, 167-172, doi:10.2144/000113072 (2009).

43 Kuehnelt, D. M., Kukovetz, E., Hofer, H. P. & Schaur, R. J. Quantitative PCR of bacteriophage lambda DNA using a second-generation thermocycler. *PCR Methods Appl.* 3, 369-371 (1994).

44 Schoepp, N. G. et al. Rapid pathogen-specific phenotypic antibiotic susceptibility testing using digital LAMP quantification in clinical samples. *Sci. Transl. Med.* 9, eaal3693, doi:10.1126/scitranslmed.aal3693 (2017).

45 Matsuda, K., Tsuji, H., Asahara, T., Kado, Y. & Nomoto, K. Sensitive quantitative detection of commensal bacteria by rRNA-targeted reverse transcription-PCR. *Appl. Environ. Microbiol.* 73, 32-39, doi:10.1128/aem.01224-06 (2007).

46 Lee, S. R., Chung, J. M. & Kim, Y. G. Rapid one step detection of pathogenic bacteria in urine with sexually transmitted disease (STD) and prostatitis patient by multiplex PCR assay (mPCR). *J. Microbiol.* 45, 453-459 (2007).

47 Francois, P. et al. Robustness of a loop-mediated isothermal amplification reaction for diagnostic applications. *FEMS Immunol. Med. Microbiol.* 62, 41-48, doi:10.1111/j.1574-695X.2011.00785.x (2011).

48 Yamazaki, W., Ishibashi, M., Kawahara, R. & Inoue, K. Development of a loop-mediated isothermal amplification assay for sensitive and rapid detection of *Vibrio parahaemolyticus*. *BMC Microbiol.* 8, 163, doi:10.1186/1471-2180-8-163 (2008).

49 Sriworarat, C., Phumee, A., Mungthin, M., Leelayoova, S. & Siriyasatien, P. Development of loop-mediated isothermal amplification (LAMP) for simple detection of *Leishmania* infection. *Parasites & vectors* 8, 591, doi: 10.1186/s13071-015-1202-x (2015).

50 Kogovšek, P. et al. Rapid loop-mediated isothermal amplification assays for grapevine yellows phytoplasmas on crude leaf-vein homogenate has the same performance as qPCR. *Eur. J. Plant Pathol.* 148, 75-84 (2017).

51 Sur, K. et al. Immiscible phase nucleic acid purification eliminates PCR inhibitors with a single pass of paramagnetic particles through a hydrophobic liquid. *The Journal of molecular diagnostics* 12, 620-628, doi:10.2353/jmoldx.2010.090190 (2010).

52 Berry, S. M., Alarid, E. T. & Beebe, D. J. One-step purification of nucleic acid for gene expression analysis via Immiscible Filtration Assisted by Surface Tension (IFAST). *Lab on a chip* 11, 1747-1753, doi:10.1039/c11c00004 g (2011).

53. 3M Fluorinert™ FC-40 Electronic Liquid. MatWeb Material Property Data http://www.matweb.com/search/DataSheet.aspx?MatGUID=2072a809f9ca4d529b1d136660736f81

54. Silicone Fluids: Stable, Inert Media. Gelest, Inc (2004).

55. Barton, Allan F M. Alcohols with Water in Solubility Data Series Volume 15 (2013).

56. 1-Undecanol. GESTIS Substance Database http://www.dguv.de/ifa/gestis-database

The invention claimed is:

1. A method to selectively remove a target compound having a water solubility equal to or greater than 0.001 g per 100 mL at 25° C. at 1 atm pressure from a solid matrix further retaining a nucleic acid, the method comprising:
   contacting the solid matrix with a target compound removing agent having a water solubility equal to or less than 0.05 g per 100 mL at 25° C. at 1 atm pressure with water having a solubility in the removing agent of less than 10 g per 100 mL at 25° C. at 1 atm pressure, the contacting performed to remove the target compound from the solid matrix.

2. The method of claim 1, wherein the target removing agent comprises a compound further having a solubility in ethanol at 25° C. at 1 atm pressure of at least 1 wt %, at least 5 wt %, at least 10 wt %, at least 20 wt %, at least 50 wt %, or at least 90 wt %.

3. The method of claim 1, wherein the target removing agent comprises a compound further having a solubility of equal to or less than 0.05 wt % in water at 25° C. at 1 atm pressure and a solubility in ethanol at 25° C. at 1 atm pressure of at least 1 wt %, at least 5 wt %, at least 10 wt %, at least 20 wt %, at least 50 wt %, or at least 90 wt %.

4. The method of claim 1, wherein the target removing agent comprises a compound of formula (X)

$$C_mH_{(2m+2-2d-i-j-k)}Q_i^aQ_j^bQ_k^c \quad \text{Formula (X)}$$

wherein
   m is the number of carbon atoms on the main ranging from 2 to 34,
   d is the degree of unsaturation ranging from 0 to 4, wherein m is equal to or larger than 2d,
   $Q^a$, $Q^b$ and $Q^c$ are each independently a functional group selected from the group consisting of hydroxyl, thiol, fluoro, chloro, bromo, iodo, cyano (—C≡N), nitro (—NO2), nitroso (—NO), sulfinyl (R'S(O)—), sulfonyl (R'S(O2)-), carbonyl (R'—CO—), carbonyloxy (R'—CO2-), oxycarbonyl (—CO2R'), oxy (R'—O—), amido (R'—CO—NR"—), carbamoyl (—CO—NR'R"), imido (R'CO—N(R"CO)—), carbamido (NR'R-"CONR'"—), carbonato (R'OCO2-),
   wherein R', R" and R'" are each independent a hydrogen (H) or a C1-C12 alkyl, C2-C12 alkenyl, C2-C12 alkynyl, C7-C12 aralkyl, or C7-C12 alkaryl group,
   i, j, and k are the numbers of $Q^a$, $Q^b$ and $Q^0$ respectively, wherein i, j, and k are each 0, 1 or 2 and at least one of i, j and k is 1 or 2.

5. The method of claim 1, wherein the target removing agent comprises a compound of formula (XI)

$$C_{m'}H_{(2m'+2-2d-n)}(OH)_n \quad \text{(XI)}$$

wherein
   m' is the number of carbon atoms on the main ranging from 9 to 34,
   d is the degree of unsaturation ranging from 0 to 4,
   n is 1,2 or 3.

6. The method of claim 5, wherein the compound of Formula (XI) is a linear or branched C9-C12 alkyl, C9-C12 alkenyl, C9-C12 alkynyl, C9-C12 aralkyl, or C9-C12 alkaryl group substituted with OH.

7. The method of claim 1, wherein the target compound removing agent comprises 1-undecanol and/or 2-dodecanol.

8. The method of claim 1, wherein the nucleic acid comprises more than 100 bases, more than 300 bases, more than 500 bases, more than 700 bases, or more than 1000 bases.

9. The method of claim 1, wherein the solid matrix comprises a silica.

10. The method of claim 9, wherein the solid matrix further comprises magnetic material encoated by the silica.

11. The method of claim 1, further comprising
   eluting the solid matrix with a nucleic acid removing agent following the contacting the solid matrix with the target compound removing agent; and
   contacting the eluted nucleic acid with a suitable reagent to perform a target biochemical reaction.

12. The method of claim 11, wherein the eluting is performed at a low eluent dilution from 1× to 2×.

13. The method of claim 11, wherein the solution comprises a detectable concentration of the nucleic acid lower than 780 copies/rxn.

14. The method of claim 11, wherein the biochemical reaction is a one-pot RT-qPCR/RT-LAMP or other RT-NAAT combinations.

15. The method of claim 11, wherein the biochemical reaction is a two-step RT-qPCR, RT-LAMP, or other RT-NAAT combination.

* * * * *